US012616544B2

(12) United States Patent
Brubaker et al.

(10) Patent No.: US 12,616,544 B2
(45) Date of Patent: May 5, 2026

(54) ROBOTIC SURGICAL SYSTEM WITH ARTIFICIAL INTELLIGENCE

(71) Applicants: William Brubaker, Palo Alto, CA (US); Paul Davis, Los Altos, CA (US)

(72) Inventors: William Brubaker, Palo Alto, CA (US); Paul Davis, Los Altos, CA (US)

( * ) Notice: Subject to any disclaimer, the term of this patent is extended or adjusted under 35 U.S.C. 154(b) by 0 days.

(21) Appl. No.: 19/061,139

(22) Filed: Feb. 24, 2025

(65) Prior Publication Data

US 2025/0295462 A1       Sep. 25, 2025

Related U.S. Application Data

(63) Continuation-in-part of application No. 18/611,155, filed on Mar. 20, 2024, now abandoned.

(51) Int. Cl.
| | |
|---|---|
| *A61B 34/10* | (2016.01) |
| *A61B 34/20* | (2016.01) |
| *A61B 34/37* | (2016.01) |
| *G06T 7/00* | (2017.01) |
| *G16H 40/63* | (2018.01) |

(52) U.S. Cl.
CPC .............. *A61B 34/37* (2016.02); *A61B 34/10* (2016.02); *A61B 34/20* (2016.02); *G06T 7/0014* (2013.01); *G16H 40/63* (2018.01); *A61B 2034/2065* (2016.02); *G06T 2207/10004* (2013.01); *G06T 2207/20081* (2013.01); *G06T 2207/30008* (2013.01); *G06T 2207/30048* (2013.01);

(Continued)

(58) Field of Classification Search
None
See application file for complete search history.

(56) References Cited

U.S. PATENT DOCUMENTS

| | | |
|---|---|---|
| 11,272,985 B2 | 3/2022 | VanDyken |
| 11,389,248 B1 | 7/2022 | Roh et al. |

(Continued)

*Primary Examiner* — Jason Holloway
*Assistant Examiner* — Bryant Tang
(74) *Attorney, Agent, or Firm* — Paul Davis

(57) ABSTRACT

A surgical robot is coupled to the surgeon console. The surgical robot performs a robotic surgical procedure. The surgical robot includes one or more robotic surgical arms. A control system is coupled to the one or more robotic surgical arms. An artificial intelligence ("AI") system includes a plurality of machine learning algorithms. The robotic surgical arms are at least partially controlled by the AI system and the control device to process intraoperative data including images captured by cameras and sensor inputs. The machine learning algorithms analyze the intraoperative data in real time, comparing it with stored images and procedural information in image recognition and procedure databases. The one or more machine algorithms enable at least partial identification of anatomical structures. In response to detection of the anatomical structures the AI system at least partially adjusts movement of the robotic surgical arms to avoid critical anatomical structures while performing the robotic surgery procedure to ensure precise targeting at the surgical site while minimizing damage to surrounding tissue at a surgical site. The AI system provides a surgeon with improved dexterity when the surgeon uses the robotic surgical arms at the surgical site, the improved dexterity resulting from at least partially analyzing the intraoperative data in real time by the one or more machine learning algorithms, enabling precise and adaptive manipulation of the robotic surgical arms at the surgical site.

14 Claims, 36 Drawing Sheets

(52) U.S. Cl.
     CPC .............. *G06T 2207/30096* (2013.01); *G06T*
     *2207/30101* (2013.01)

(56) References Cited

U.S. PATENT DOCUMENTS

| 11,392,109 | B2 | 7/2022 | Cella et al. |
| 11,728,910 | B2 | 8/2023 | Cella et al. |
| 11,844,574 | B2 | 12/2023 | VanDyken |
| 12,089,905 | B1 | 9/2024 | Roh et al. |
| 2018/0284758 | A1 | 10/2018 | Cella et al. |
| 2019/0142520 | A1 | 5/2019 | VanDyken |
| 2021/0342836 | A1 | 11/2021 | Cella et al. |
| 2022/0151703 | A1 | 5/2022 | VanDyken |
| 2022/0172206 | A1 | 6/2022 | Cella et al. |
| 2022/0172207 | A1 | 6/2022 | Cella et al. |
| 2022/0172208 | A1 | 6/2022 | Cella et al. |

ROBOTIC SURGICAL SYSTEM WITH ARTIFICIAL INTELLIGENCE

BACKGROUND

Field of the Invention

The present disclosure relates to robotic surgery, and more specifically to surgery utilizing artificial intelligence.

Description of the Related Art

Robotic surgery, also called robot-assisted surgery, allows physicians to perform many types of complex procedures with more precision, flexibility and control than is possible with conventional techniques. Robotic surgery can be used with minimally invasive surgery and traditional open surgical procedures.

One type of robotic surgical system includes a camera arm and mechanical arms with surgical instruments attached to them. The surgeon controls the arms while seated at a computer consol near the operating table. The consol gives the surgeon a high-definition, magnified, 3D view of the surgical site. The surgeon leads other team members who assist during the operation.

Robotic surgical systems enhances precision, flexibility and control during the operation and allows surgeons to better see the site, compared with traditional techniques. Using robotic surgery, surgeons can perform delicate and complex procedures that may be difficult or impossible with other methods.

One of the most used robotic surgical systems includes a camera 46 and surgical instruments attached to robotic arms. The surgeon controls the robotic arms from a viewing screen, which is usually situated in the same room as the operating table. However, viewing screen can be located far away, allowing surgeons to perform telesurgery from remote locations. The surgeon views a magnified three-dimensional view of the patient's surgical site.

Robotic surgical system provided many benefits, including but not limited to: improved dexterity of the robotic devices (compared to a surgeon's hand) which allows for access to hard to reach places; improved visualization of the surgical site due to the magnification of the camera 46 which is displayed on the surgeon's viewing screen, less surgeon fatigue; elimination of a surgeon's hand tremors particularly during long surgical procedures; shorter hospital stays and faster recovery for the patient; reduced patient infection; lower blood loss and fewer blood transfusions; less pain and scarring; lower time after surgery for the patient to return to normal activity; faster return to normal function; and the like.

SUMMARY

An object of the present invention is to provide a robotic surgery system with enhanced imaging, including image recognition.

Another object of the present invention is to provide a robotic surgery system with an improved treatment planning.

A further object of the present invention is to provide a robotic surgery system with an improved risk assessment.

Yet another object of the present invention is to provide a robotic surgery system with improved robot-assisted navigation.

A further object of the present invention is to provide a robotic surgery system with autonomous robotics.

An object of the present invention is to provide a robotic surgery system with intraoperative decision support.

Still another object of the present invention is to provide a robotic surgery system with improved postoperative monitoring and analysis.

A further object of the present invention is to provide a robotic surgery system with continuous learning and improvement.

These and other objects of the present invention are achieved in a surgical system including: a surgeon console including a display, and a planning module that allows a surgeon to create a plan for a robotic surgery procedure. The surgeon console is coupled to a robotic surgical system that includes an image recognition database and a procedure database, a surgical computing device coupled to the robotic surgery control system. The surgical computing device includes a memory with stored surgical instructions. A surgical robot is coupled to the surgeon console. The surgical robot performs a robotic surgical procedure. The surgical robot includes one or more robotic surgical arms. A control system is coupled to the one or more robotic surgical arms. An artificial intelligence ("AI") system includes a plurality of machine learning algorithms. The robotic surgical arms are at least partially controlled by the AI system and the control device to process intraoperative data including images captured by cameras and sensor inputs. The machine learning algorithms analyze the intraoperative data in real time, comparing it with stored images and procedural information in image recognition and procedure databases. The one or more machine algorithms enable at least partial identification of anatomical structures. In response to detection of the anatomical structures the AI system at least partially adjusts movement of the robotic surgical arms to avoid critical anatomical structures while performing the robotic surgery procedure to ensure precise targeting at the surgical site while minimizing damage to surrounding tissue at a surgical site. The AI system provides a surgeon with improved dexterity when the surgeon uses the robotic surgical arms at the surgical site, the improved dexterity resulting from at least partially analyzing the intraoperative data in real time by the one or more machine learning algorithms, enabling precise and adaptive manipulation of the robotic surgical arms at the surgical site. One or more computer processors are used in the robotic surgery procedure. A non-transitory computer-readable storage medium stores computer instructions, which when executed by the one or more computer processors, cause the surgical system to monitor the robotic surgery procedure. A planned surgical step of the robotic surgery procedure is executed using the one or more machine learning algorithms. A determination is made that the robotic surgery procedure has been completed.

In another embodiment of the present invention a surgeon console includes a display, and a planning module that allows a surgeon to create a plan for a robotic surgery procedure. The surgeon console is coupled to a robotic surgical system that includes an image recognition database and a procedure database. The surgical computing device includes a memory with stored surgical instructions. A surgical robot is coupled to the surgeon console. The surgical robot performs a robotic surgical procedure. The surgical robot includes one or more robotic surgical arms. A An artificial intelligence ("AI") system includes a plurality of machine learning algorithms. The robotic surgical arms are at least partially controlled by the AI system to process intraoperative data including images captured by cameras and sensor inputs. The machine learning algorithms analyze the intraoperative data in real time, comparing it with stored images and procedural information in image recognition and procedure databases. The one or more machine algorithms enable at least partial identification of anatomical structures. In response to detection of the anatomical structures the AI system at least partially adjusts movement of the robotic surgical arms to avoid critical anatomical structures while performing the robotic surgery procedure to ensure precise targeting at the surgical site while minimizing damage to surrounding tissue at a surgical site. The AI system provides a surgeon with improved dexterity when the surgeon uses the robotic surgical arms at the surgical site, the improved dexterity resulting from at least partially analyzing the intraoperative data in real time by the one or more machine learning algorithms, enabling precise and adaptive manipulation of the robotic surgical arms at the surgical site. One or more computer processors are used in the robotic surgery procedure. A non-transitory computer-readable storage medium stores computer instructions, which when executed by the one or more computer processors, cause the surgical system to monitor the robotic surgery procedure. A planned surgical step of the robotic surgery procedure is executed using the one or more machine learning algorithms. A determination is made that the robotic surgery procedure has been completed.

DETAILED DESCRIPTION

Figure 1A:
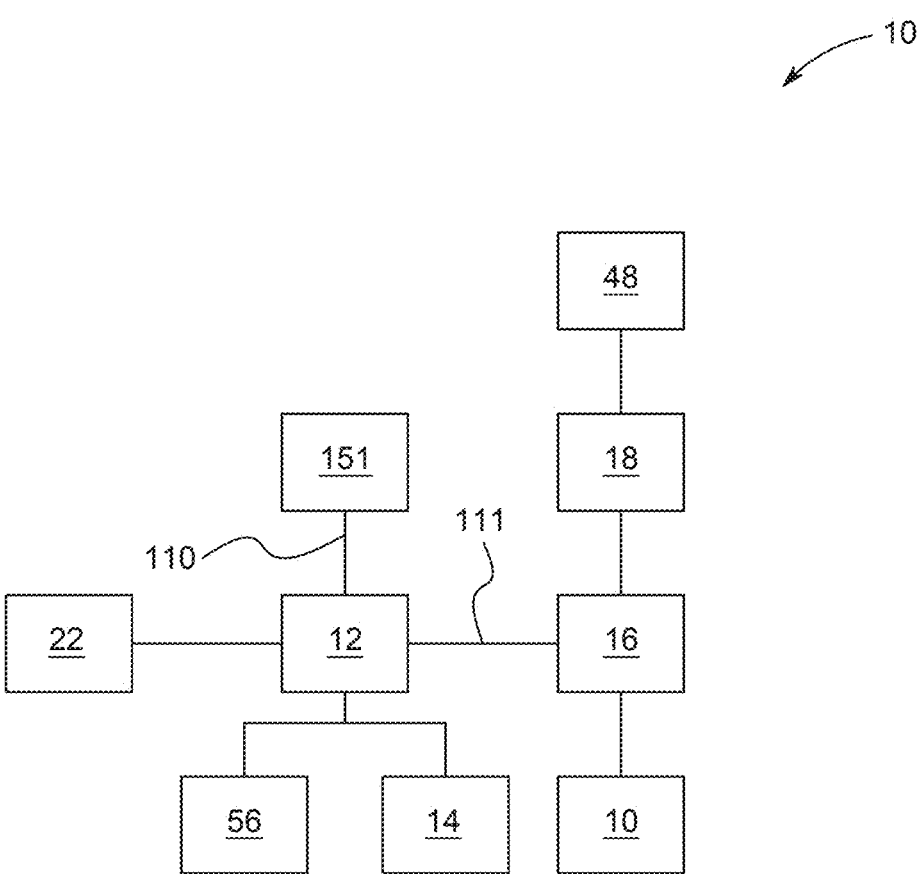
FIG. 1A illustrates one embodiment of a robotic surgical system of the present invention.

In one embodiment, illustrated in FIG. 1A, a robotic surgical system 10 includes: a surgeon consol 12, optical system 14, patient consol 16, surgical instruments 18, and the like. In one embodiment, robotic surgical system 10 includes a surgeon computer 151 (more fully disclosed hereafter), a surgical robot 20, and a robotic surgery control system 22. In one embodiment, a robotic surgical manipulator 152, hereafter the "patient consol 16" has one or more robotic surgical arms 54. As a non-limiting example, robotic surgical manipulator 152 (16) has a base from which the surgical instruments 18 is supported. In one embodiment, surgical instruments 18 are each supported by the positioning linkage and the actuating portion 158 of the arms 54, as more fully discussed hereafter.

In one embodiment, only a surgeon counsel 12 is provided, with all or some of the elements found in the optical system 14 and patient consol 16. In one embodiment, robotic surgical system 10, surgeon consol 12 and patient consol 16 are provided. The other elements can be at either one. An assistant can work with the surgeon.

As a non-limiting example, robotic surgery surgical system 10 is not limited to robots actually performing your surgery. As a non-limiting example, surgeon consol 12 connects a surgeon to robotic system 20 and to the patient. In one embodiment, surgeon consol 12 includes a set of finely tuned hand controls and a high-definition screen. As a non-limiting example, the surgeon controls robotic arms 54 and surgical instruments 18 using the surgeon's bands.

As non-limiting examples, robotic surgical system 10 can be used in one or more of the following areas: ophthalmology, cardiology, thoracic, ENT, gastrointestinal, bone, spine, transplants, general surgery, urology, pediatrics, and the like.

As a non-limiting example, robotic surgical system 10 includes surgeon consol 12. Patient consol 16, with arms 54 configured to be coupled to surgical instruments 18. A robotic surgery control system 22 is coupled to the surgical robot 20 A surgical computing device 151 is coupled to the robotic surgery control system 22. The surgical computing device 151 includes a memory 63 with programmed instructions 67 of surgical computing device 151 from a database 61 one or more processors 62 are coupled to the memory 63 and configured to execute stored, Database 61 uses one or more algorithms relative to search engine 65 for selection, full creation, partial creation, and the like, of programmed instructions 67. The one or more algorithms 65 selected from at least one of: supervised learning; classification and regression; decision tree; random forest; support vector machines; Naïve Bayes; linear regression; logistic regression; enhanced imaging; image recognition; treatment planning; risk assessment; robot-assisted navigation; path planning; collision avoidance; autonomous robotics; steady hand assistance; intraoperative decision support; real-time feedback; alert and warning; postoperative monitoring and analysis; prediction; patient outcomes: continuous learning and improvement; ad data analysis. The programmed instructions 67 of surgical computing device 151 being used by a surgeon and the robotically assisted surgical system to preform one or more of: train at least one machine learning model; improve at least one machine learning models and apply the machine learning model to generate one or more parameters used for a surgical procedure, a pre-operative plan or procedure, or a postoperative surgery plan or procedure that can be used by the surgeon.

In one embodiment, the # programmed instructions 67 of surgical computing device 151 are directed to improved patient image and video analysis. As non-limiting examples, # the programmed instructions 67 of surgical computing device 151 are directed to and execute enhanced imaging AI algorithms to improve the quality and interpretation of medical imaging. In one embodiment, the AI algorithms are used for one or more of: real-time identification of anatomical structures, tumors, and critical tissues; surgical planning; treatment planning to create personalized surgical plans; risk assessment to predict potential complications; surgical robot navigation; plan optimal paths for at least one of the arms and the surgical instruments 18; provide collision avoidance to detect and prevent collisions between the surgical instruments 18 and anatomical structures in real-time; autonomous robotics; steady hand assistance for improved stability and precision to surgical instruments 18; intraoperative decision support; real-time feedback that analyzes real-time data from a surgery; postoperative monitoring and analysis; analyze postoperative data to predict current patient outcomes and identify factors that contribute to successful surgeries or reduced complications; continuous learning and improvement; data analysis for datasets of surgical procedures to identify one or more of: patterns, trends, and best practices; development of robotic surgical systems 22 that continuously learn and adapt based on the experiences and feedback from various surgical procedures.

In various embodiments, the programmed instructions 67 of surgical computing device 151 use historical procedure data selected from one or more of: historical patient data; historical data; and historical healthcare professional data associated with a plurality of Instances of the surgical procedure; execute stored programmed instructions 67 of surgical computing device 151 to update the machine learning model based on a patient data and patient outcome data generated following execution of the surgical procedure according to a surgical plan; use one or more of direct Monte Carlo sampling; stochastic tunneling; and parallel tempering to optimize a predictor equation, generate anatomy data pre-operatively from medical image data of the anatomy of a patient; generate an intra-operative with a plurality of recommended actions associated with a surgical plan; evaluate a result of an execution of a recommended actions; update one or more inputs based on the evaluation to alter another one of the recommended actions to be executed subsequent to the one of the recommended actions; and update one or more inputs based on one or more deviations to recommended actions.

In one embodiment, a non-transitory computer readable includes programmed instructions 67 of surgical computing device 151 for improved surgical planning using machine learning. This can include executable code that, when executed by one or more processors 62, causes the one or more processors 62 to: train a machine learning model based on an artificial neural network and historical case log data sets including historical outcome data correlated with one or more of historical patient data, or historical healthcare professional data associated with a plurality of instances of a surgical procedure; where the artificial neural network includes a plurality of input nodes and downstream nodes coupled by connections having associated weighting values; applies a machine learning model to current patient data for a current patient to generate a predictor equation for a surgical result or outcome; instructs robotic surgical system 10 to implement one or more portions of a surgical procedure according to a surgical plan; and updates the machine learning model based on current patient data and current outcome data generated for the current patient following execution of the surgical procedure, In one embodiment, the non-transitory computer readable medium uses weighting values and includes a predictor equation coefficient, wherein the executable code, when executed by the one or more processors 62, further causes the one or more processors 62 to use one or more of: Monte Carlo sampling; stochastic tunneling; and parallel tempering to optimize a predictor equation.

In one embodiment, the executable code, when executed by the one or more processors 62, further causes the one or more processors 62 to: provide input data comprising signals that correspond with the input nodes to the artificial neural network as seeding data, wherein the input data is extracted from the historical case log data sets; and alters the weighting values until the artificial neural network is configured to provide a result that corresponds with the historical outcome data.

In one embodiment, the executable code, when executed by the one or more processors 62, further causes the one or more processors 62 to provide one or more of: obtain a sensitivity threshold value; and apply a sensitivity threshold value to disregard one or more of the input nodes. In one embodiment, the executable code, when executed by the one or more processors 62, further causes the one or more processors 62 to generate anatomy data pre-operatively from medical image data of an anatomy of the current patient.

In one embodiment, the executable code, when executed by the one or more processors 62, further causes the one or more processors 62 to provide one or more of: generation of an intra-operative algorithm with a plurality of recommended actions associated with the surgical plan; evaluate a result of an execution of one of the recommended actions; and update one or more inputs to the intra-operative algorithm based on the evaluation to alter another one of the recommended actions to be executed subsequent to the one of the recommended actions, wherein the one or more inputs are updated based on one or more deviations to the one of the recommended actions In one embodiment, a method for improved surgical planning is provided that trains at least one machine learning model based on one or more of: historical case log data sets including historical outcome data correlated with one or more of historical patient data; historical surgical data; historical healthcare professional data associated with a plurality of instances of a surgical procedure; applies machine learning to current patient data; and updates the machine learning model based on the current patient data and current outcome data generated for the current patient following execution of the surgical procedure according to the surgical plan. In one embodiment, the machine learning model includes an artificial neural network, wherein the artificial neural network has a plurality of input nodes and downstream nodes coupled by connections having associated weighting values.

In one embodiment, each of the weighting values has a predictor equation coefficient. In one embodiment, a sensitivity threshold value is obtained; and a sensitivity threshold value is applied to disregard one or more of the input nodes. As a non-limiting example, input data includes signals that correspond with the input nodes to the artificial neural network as seeding data, wherein the input data is extracted from the historical case log data sets. As a non-limiting example, weighting values are altered until the artificial neural network is configured to provide a result that corresponds with the historical outcome data.

In one embodiment, a method, executed by robotic surgical system 10, intraoperatively monitors a surgical procedure being performed on a patient by surgical robot. One or more processors 62 executes intraoperative data that describes the surgical procedure based on the monitoring. The one or more processors 62 extract one or more features from the intraoperative data. The intraoperative data is at least one physiological condition of the patient during the surgical procedure, One or more surgical tools are positioned and used during the surgical procedure. A planned surgical step is planned using a machine learning model of robotic surgical system 10. The planned surgical step is based on the features and a machine learning model trained based database 61 of historical data describing previous surgical procedures, and is responsive to the confidence score being less than a threshold. The one or more processors 62 generate a prompt for a surgeon to intervene, when required, in the surgical procedure. Robot 20 control is given to the surgeon for manually . . . controlled operation of the surgical robot 20 for completion of the planned surgical step. In response to completion of the planned surgical step, one or more subsequent surgical steps are autonomously performed on the patient using the surgical robot. In responsive to the confidence score being greater than the threshold, the surgical robot 20 performs the surgical step. The one or more processors 62 determines if the surgical procedure is complete. In one embodiment live surgical procedures are monitored by robotic surgical system 10. The machine learning mode can be trained, by the one or more processors 62, while the live surgical procedures are being performed.

In one embodiment, training the machine learning model includes: generating, by the one or more processors 62, a prediction for a next surgical step performed by a previous surgeon in a previous surgical procedure based on the historical data describing previous surgical procedures; and comparing, by the one or more processors 62, the prediction to an actual next surgical step performed by the previous surgeon in the previous surgical procedure. As a non-limiting example, the comparing for training is by a regression model of robotic surgical system 10. In one embodiment, virtual robotic surgical procedures are based on the historical data describing previous surgical procedures for training the machine learning model to direct the surgical robot.

In one embodiment, the one or more processors 62 receive an indication from the surgeon for the surgical robot 20 to continue with the surgical step. The one or more processors 62 determine whether the surgical procedure is complete. Live surgical procedures can be monitored. # The one or more processors 62 train by the machine learning model based on the live surgical procedures while the live surgical procedures are being performed. In one embodiment, the machine learning model is trained by generating, by the one or more processors 62, a prediction for a next surgical step performed by a previous surgeon in a previous surgical procedure based on the historical data describing previous surgical procedures.

The prediction is compared, by the one or more processors 62, to an actual next surgical step performed by the previous surgeon in the previous surgical procedure. The comparison uses a regression model of robotic surgical system 10. In one embodiment, in responsive to receiving the indication that overrides by the confidence score, the surgical step is performed.

In one embodiment, the surgical procedure being performed can be halted on the patient in responsive to the confidence score being less than the threshold. In one embodiment, the surgical robot 20 monitors activity of the surgeon during the surgical procedure. A notification can be provided indicating tremors of the surgeon associated with the activity. The notification can include a request for the surgeon to hand off control of the surgical procedure to surgical robot.

In one embodiment, robotic surgery system 10 includes a non-transitory computer-readable storage medium storing computer programmed instructions 67 of surgical computing device 151. The medium storing computer programmed instructions 67 of surgical computing device 151 cause the robotic surgical system 10 to: monitor, by robotic surgical system 10, a robotic-assisted surgical procedure being performed on a patient by surgical robot 20 generates intraoperative data that describes the surgical procedure. One or more features are extracted from the intraoperative data. A confidence score is determined, and a planned surgical step uses a machine learning model of the robotic surgical system 10. # The planned surgical step to be performed by the surgical robot 20 is based on the features. The machine learning model can be based on historical data describing previous surgical procedures. In responsive to the confidence score being less than a threshold, a prompt can be generated for a surgeon to intervene in the surgical procedure. The one or more computer processors 62 determine whether the robotic-assisted surgical procedure is completed, based on at least a portion of the intraoperative data of the patient indicating a condition of the patient. In responsive to determining the robotic-assisted surgical procedure has been completed, the robotic-assisted surgical procedure is determined.

When the confidence score is greater than the threshold, the surgical step can be performed. The computer programmed instructions 67 of surgical computing device 151 can cause robotic surgical system 10 to; monitor live surgical procedures; and train the machine learning model based on the live surgical procedures while the live surgical procedures are being performed. In one embodiment, the computer programmed instructions 67 of surgical computing device 151 trains the machine learning model cause to: generate a prediction for a next surgical step performed by a previous surgeon in a previous surgical procedure based on the historical data describing previous surgical procedures; and compare the prediction to an actual next surgical step performed by the previous surgeon in the previous surgical procedure, resulting in training a regression model of robotic surgical system 10. In one embodiment, the computer programmed instructions 67 of surgical computing device 151 causes robotic surgical system 10 to perform virtual robotic surgical procedures based on historical data describing previous surgical procedures for training the machine learning model to direct the surgical robot.

As a non-limiting example, the computer programmed instructions 67 of surgical computing device 151 can cause robotic surgical system 10 to: receive an indication from the surgeon for the surgical robot 20 to continue with the surgical step; responsive to receiving the indication, override the confidence score, and perform, by surgical robot, the surgical step.

In one embodiment, the computer programmed instructions 67 of surgical computing device 151 further cause robotic surgical system 10 to: monitor, by the surgical robot, activity of the surgeon during the surgical procedure; generate, by the one or more processors 62, a notification indicating tremors of the surgeon associated with the activity, the notification including a request for the surgeon to hand off control of the surgical procedure to the surgical robot.

In one embodiment, a computer-implemented method extracts features from intraoperative data describing a surgical procedure being performed on a patient by a surgical robot; determining a confidence score and a planned surgical step using a machine learning model based on the features, the planned surgical step to be performed by a surgical robot, the machine learning model trained based on historical data describing previous surgical procedures; and responsive to the confidence score being less than a threshold, generating a prompt for a surgeon to intervene in the surgical procedure; after generating the prompt for the surgeon, receiving input from the surgeon for the planned surgical step; determining whether to override the confidence score based on the input from the surgeon; and in responsive to determining to override the confidence score, autonomously performing, by the surgical robot 20 the planned surgical step; and responsive to determining not to override the confidence score, transferring surgical robot 20 control to the surgeon for manual operation of the surgical robot 20 to robotically perform the planned surgical step.

In one embodiment, the computer-implemented method, in responsive to the confidence score being greater than the threshold, performs, by the surgical robot, the surgical step. As a non-limiting example, the computer-implemented method: monitored live surgical procedures; and trains the machine learning model based on the live surgical procedures while the live surgical procedures are being performed. In one embodiment, the machine learning model is trained to: generates a prediction for a next surgical step performed by a previous surgeon in a previous surgical procedure based on the historical data describing previous surgical procedures; and compares the prediction to an actual next surgical step performed by the previous surgeon in the previous surgical procedure, the comparing for training a regression model. In one embodiment, the computer-implemented performs virtual robotic surgical procedures are performed based on the historical data describing previous surgical procedures for training the machine learning model to direct the surgical robot. As a non-limiting example, AI execution, output, results, information, mathematical equations, and the like are seen at display 628, In one embodiment, a control cable 110 couples the computer 151 of surgeon consol 12 with patient consol 16, to control the surgical system 12, including the remote controllable equipment arms 54 and surgical instruments. A control cable 111 is coupled computer 151 and patient consol 16 and surgeon's consol 12, providing control of arms 54 and surgical instruments 18 through patient consol 16.

Figure 1B:
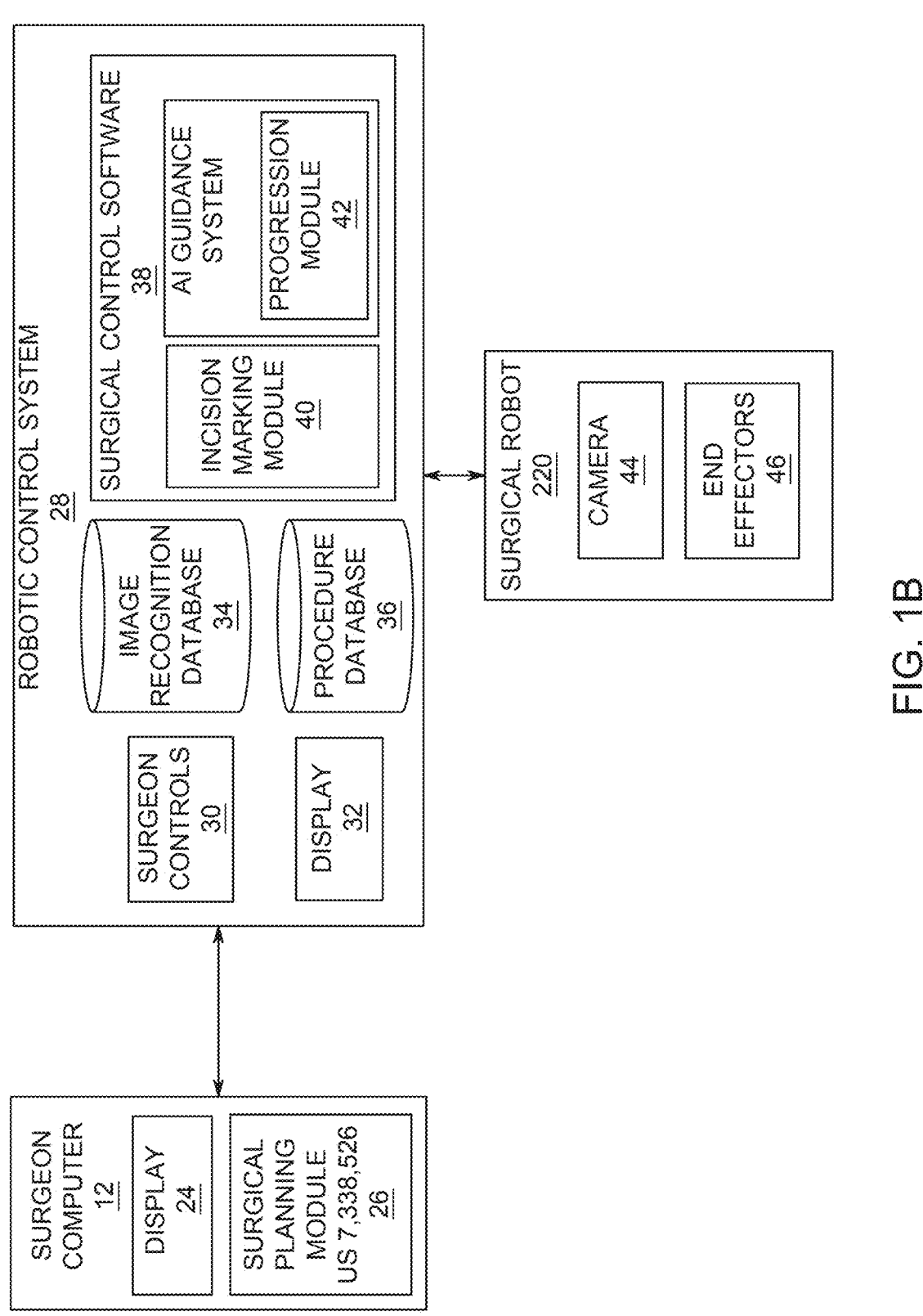
FIG. 1B illustrates one embodiment of a robotic surgery system with artificial intelligence of the present invention.
Figure 1C:
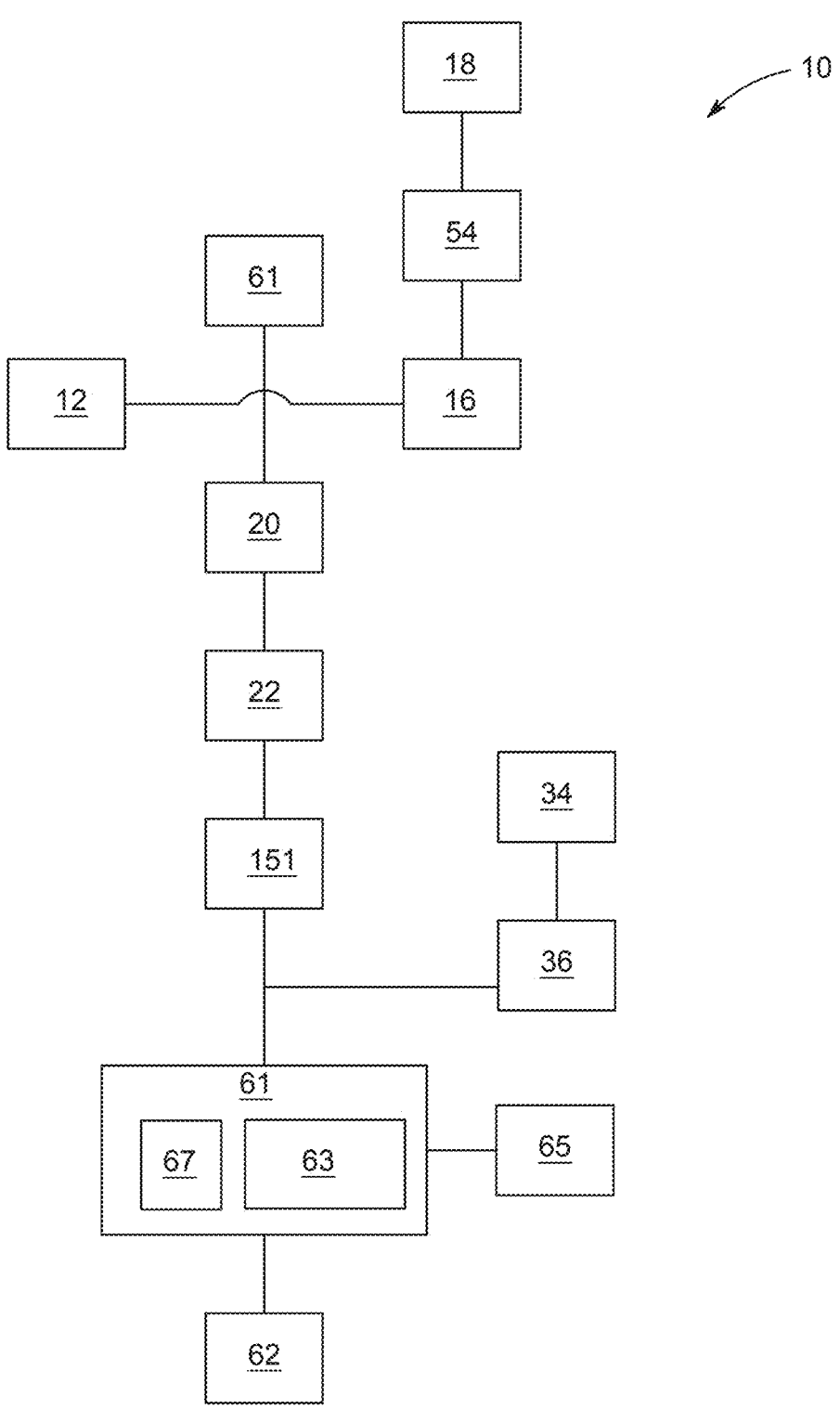
FIG. 1C illustrates another embodiment of a robotic surgical system of the present invention.

In various embodiments, robotic surgery control system 22 can use images obtained prior to and/or during surgery to guide a surgical instruments 18, end effector 48, and the like. In one embodiment, an endoscope can be used. Endoscope 58 (hereafter "Visualization Device") can constantly interact with an anterior-posterior (AP) view, allowing a surgeon to be constantly looking at Visualization Device 58. This system can be expanded to cover the entirety of the surgical procedure. Using Visualization Device 58 allows for locating Visualization Device 58 inside of the patient as an additional reference point for the surgical navigation program. The configuration of Visualization Device 58 can be selected based on the instrument to move delivered over FIG. 1B illustrates one embodiment of a robotic surgical system 10. In one embodiment, surgeon consol 12 includes a display 24, a planning module 26. Planning module 26 allows the surgeon to create a plan for a robotic surgery procedure. The plan can be created by a various of different of different methods In one embodiment, surgeon consol 12 is coupled to a robotic surgical system 10. Robotic surgery control system 22 can include one or more of: surgeon controls 30, a display 32 (24), an image recognition database 34, a procedure database 36, surgical control software 38, an incision module 40, an artificial intelligence ("AI") system 42 with a progression module 44. # Surgical robot 20 can include a camera 46 and end effectors 48. As a non-limiting example, a variety of algorithms can be used with AI system 42 including but not limited to: supervised learning; classification and regression; decision tree; random forest; support vector machines; Naïve Bayes; linear regression; logistic regression; enhanced imaging; image recognition; treatment planning; risk assessment; robot-assisted navigation; path planning; collision avoidance; autonomous robotics; steady hand assistance; intraoperative decision support; real-time feedback; alert and warning; postoperative monitoring and analysis; prediction; patient outcomes: continuous learning and improvement; data analysis; and the like, as more fully set forth below.

It will be appreciated that one or more databases, such as database 61, can be included, as set forth herein.

As a non-limiting example, procedure database 36 can include medical records data, images (e.g., pre- and post-surgical images), physician input, sensor data, and the like. The images can include MRI or CAT scans, fluoroscopic images, or other types of images. The sensor data can be collected during procedures, and the like, related to all procedures of this type. Databases 34 and 36 can be queried by surgical control 30 or all medical imaging from the current patient and by progression module 36 for data for all similar patients who had the same procedure.

Image recognition database 34 can include images taken by surgical robot cameras 46 that are defined by the surgeons and updated with each use of robotic surgical system 10 for greater accuracy. As a non-limiting example, surgeon controls 30 can be used manual manipulation of surgical robot 20, cither to take over when the AI cannot proceed or to navigate the end effector 48.

As a non-limiting example, robotic surgical system 10 utilizes incision marking module 40 for determining patient position. Optionally, an incision site can be marked AI system 42 is then initiated.

As a non-limiting example, AI system 42 can use 644 to take an image of the point of interest and progression module 42 compares the image received from camera 46 to image to the image recognition database 34 to determine if the tissue present is the desired tissue type that will allow surgical robot 20 to proceed. In one embodiment, progress through a tissue type is displayed based on the number of layers of the current tissue removed as compared to the average number of layers removed in other patients who had the same procedure with a same amount of anatomical volume at the same or surgical point of interest.

In one embodiment, an imaging system and progression module 36 are initially trained using a neural network/machine learning. Using machine learning systems which construct algorithms that can learn from and then make predictions on the image data. Image data-driven predictions can be made by building a mathematical model from image input data. The image data can be used for the final model which usually comes from multiple datasets, including but not limited to datasets

A trained dataset is built; real-time images are used with robotic surgical system 10. As tissues are identified, the tissue types can be annotated virtually over the real time images, with a % probability of identification.

In one embodiment, robotic surgical system 10 allows the surgeon to stop the process. Stopping the process may include a teaching step in which the surgeon defines the tissue type visible, to improve the functionality of the image recognition database 34 software.

Historical data of many surgeries can include information relative to the amount of time (video) and the virtual identified images on a tissue. In one embodiment, a sequence of image-recognized tissue (and the timing of getting to and through these recognized tissues) is compared to the historical database. When the real-time recognized tissues are correlated with the same sequence of tissues in the historical database, robotic surgical system 10 then can proceed. When a recognized tissue does not appear in the sequence history, or if the recognized tissue appears earlier than expected, an alert is provided As non-limiting examples, end effectors 48 can include retractor tubes and surgical hardware, in addition to the incision markers, removal os 18, skin/muscle fascia incision instruments 18. If a new end effector 48 is needed, the surgeon or support staff makes the hardware adjustment before robotic surgical system 10 proceeds to the next step in the pre-operative plan. Robotic surgical system 10 returns to AI system 42 until the next surgical step is completed. This process continues to loop until the procedure is complete.

Figure 2:
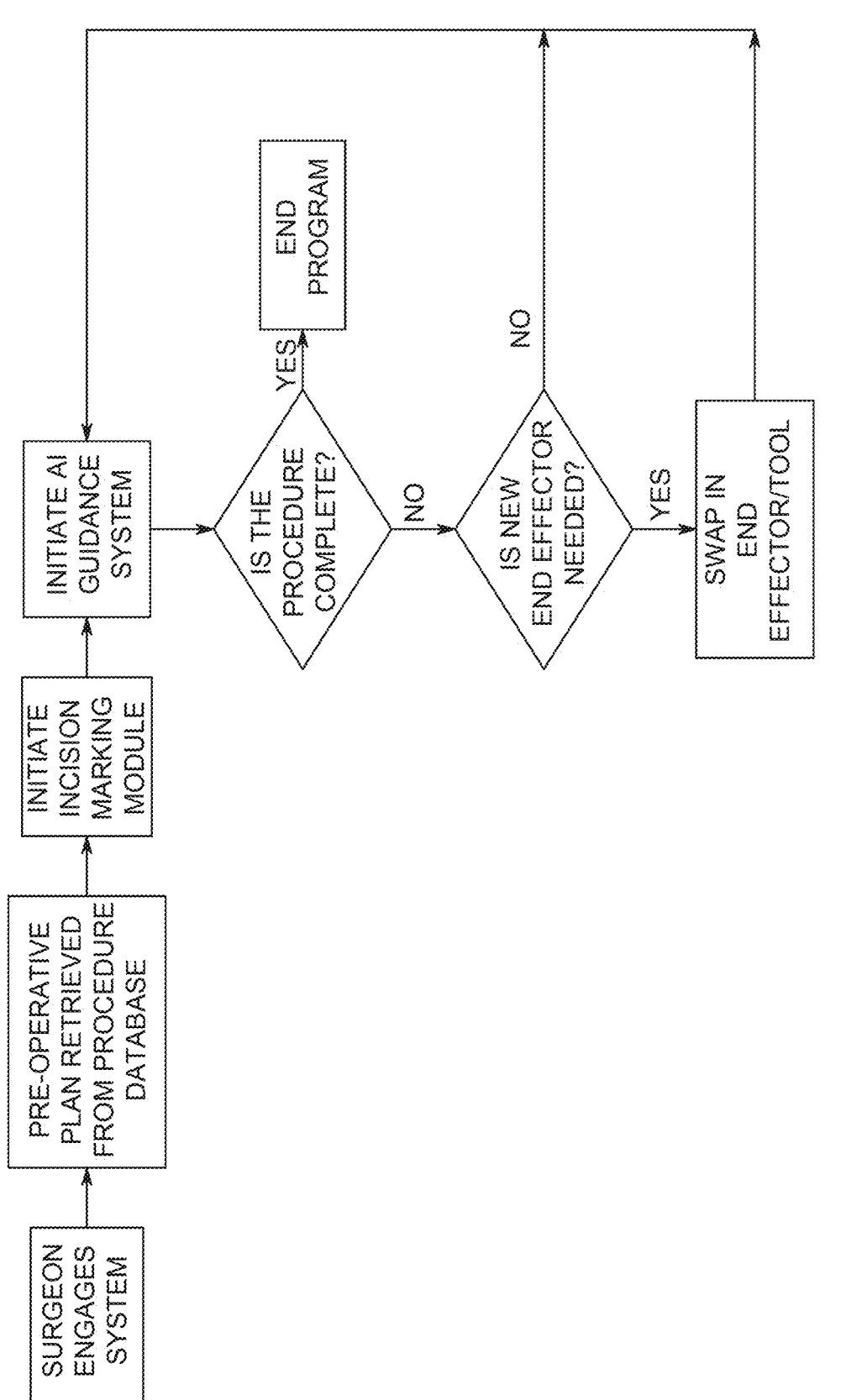
FIG. 2 illustrates one embodiment of a surgical control software module of the present invention.

FIG. 2 is a flow chart illustrating one embodiment of surgical control software 38. In one embodiment, the pre-operative plan, can be retrieved from the procedure database 36. In one embodiment, robotic surgical system 10 uses a series of prompts in preparation for surgery. As a non-limiting example, robotic surgical system 10 provide a guidance setup with visual and auditory feedback to the surgeon and assistants at a tele-operational assembly touchpad interface, as well as feedback on a consol touchscreen interface, described hereafter, providing access of guidance information from a variety of locations within the operating room.

Figure 3:
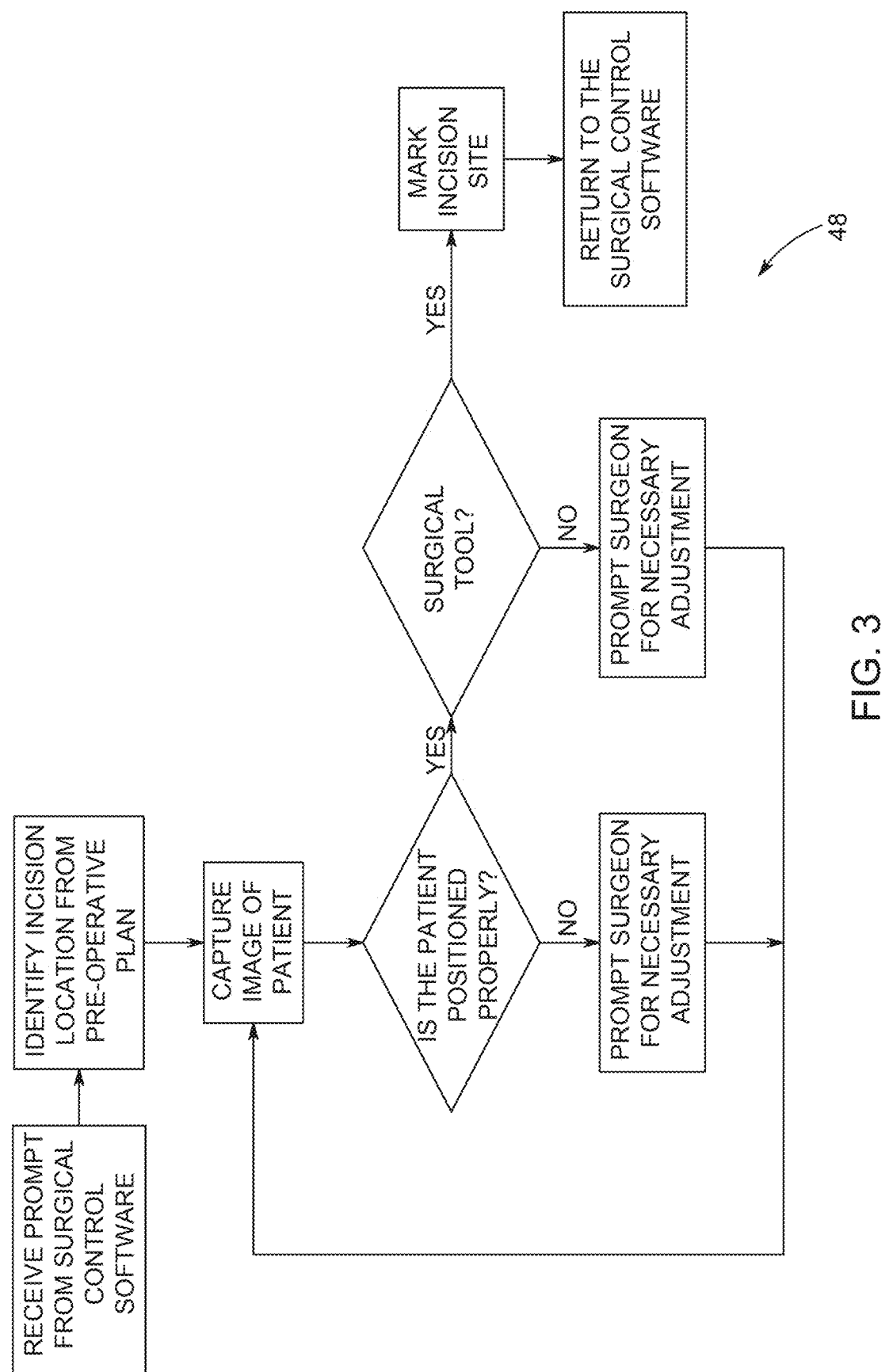
FIG. 3 illustrates one embodiment of an incision marking module of the present invention.

In one embodiment, shown in FIG. 3, an embodiment of an incision marking module 40 that is part of the surgical control software 38. Module begins 40 when it receives a prompt from surgical control software 38. As a non-limiting example, module 40 can capture an image of the patient to determine if they are properly positioned on the operating table. If not, the surgeon or support staff are prompted for the necessary adjustment and a new image is captured. This loop continues until robotic surgical system 10 is satisfied that the patient is properly positioned. Placement of a surgical instrument 18 is checked by imaging system. This process loops in the same way as the patient positioning is looped. The surgeon and/or assistants are prompted for the necessary adjustment to the guide the surgical tube and another image is taken until the robotic surgical system 10 is satisfied that the surgical instrument 18 is properly placed.

Figure 4:
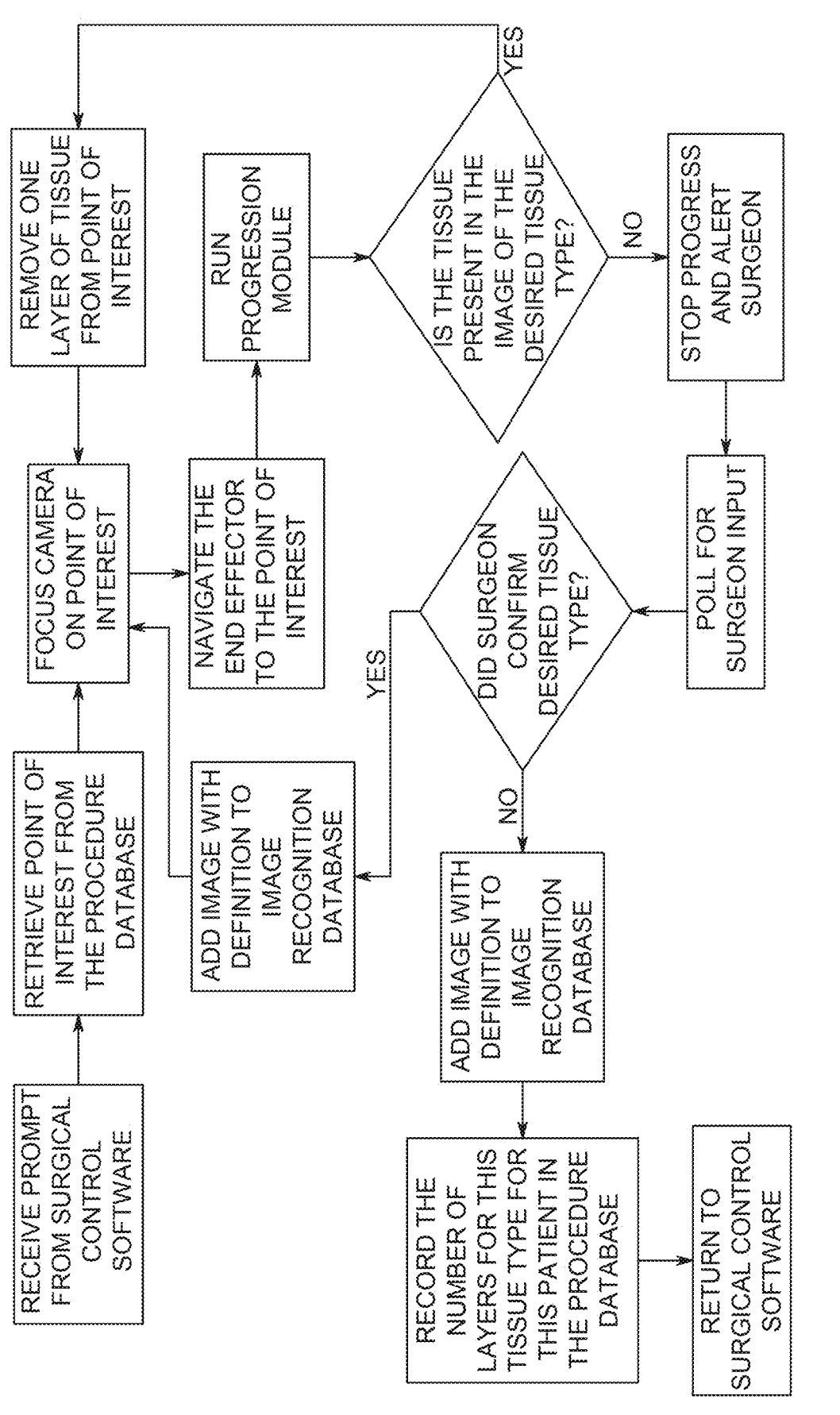
FIG. 4 illustrates one embodiment of an artificial guidance system of the present invention

As a non-limiting example AI system 42 is shown in FIG. 4. More details are provided hereafter.

As a non-limiting example, as shown in, AI system 42 is illustrated. In one embodiment, AI system 42 triggers progression module 36 when imaging robotic surgical system 10 and the end effectors 48 are at the point of interest on the current patient AI system 42 includes AI engine 65, as more fully set forth below.

In one embodiment, AI engine 65 takes in a description of a problem and how one would go about teaching concepts covering aspects of the problem to be solved, and AI engine 65 compiles the coded description into lower-level structured data objects that a machine can more readily understand, builds a network topology of the main problem concept and sub-concepts covering aspects of the problem to be solved, trains codified instantiations of the sub-concepts and main concept, and executes a trained AI model 706 containing one, two, or more neural networks.

In one embodiment, AI engine 65 can abstract away and automate the low-level mechanics of AI. AI engine 65 can manage and automate much of the lower level complexities of working with AI. Each program developed in the pedagogical programming language can be fed into AI engine 65 in order to generate and train appropriate intelligence models.

AI engine 65 can abstract generation of a neural network topology for an optimal solution and faster training time with a curriculum and lessons to teach the neural network via recursive simulations and training sessions on each node making up the neural network.

In one embodiment, AI engine 65 can contain a vast array of machine learning algorithms, has logic for picking learning algorithms and guiding training, manages data streaming and data storage, and provides the efficient allocation of hardware resources. AI engine 65 can be built with an infrastructure that supports streaming data efficiently through the system. AI engine 65 can use a set of heuristics to make choices. The set of heuristics also make it possible for AI engine 65 to choose from any number of possible algorithms, topologies, and the like.

An image of the point of interest is taken and an image recognition with database 34 identifies the tissue type present in the image taken of the point of interest on the current patient. As a non-limiting example, image recognition database 34 identifies the tissue type and to store the definitions of tissue types found in images as they are defined by surgeons using robotic surgical system 10.

Figure 6:
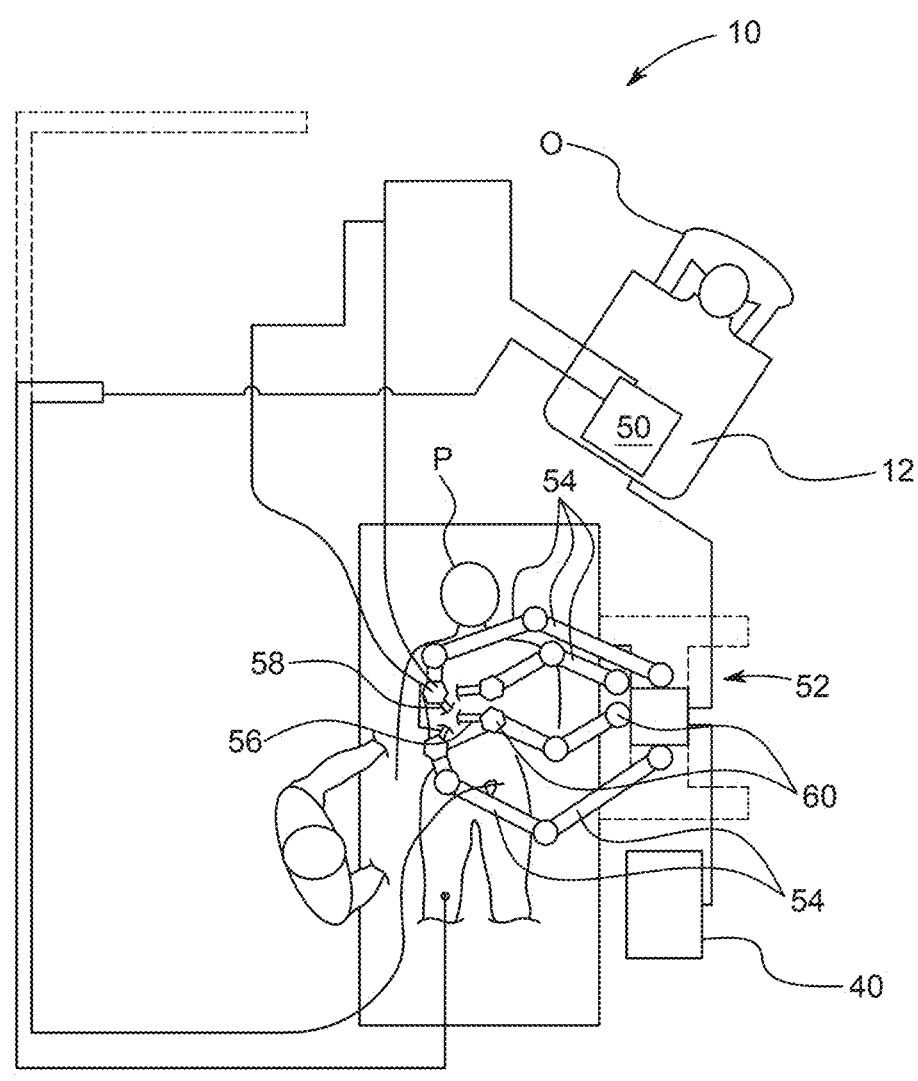
FIG. 6 illustrates one embodiment of a block diagram of a first robotic surgery system to perform robotic surgical procedures of the present invention.
Figure 7:
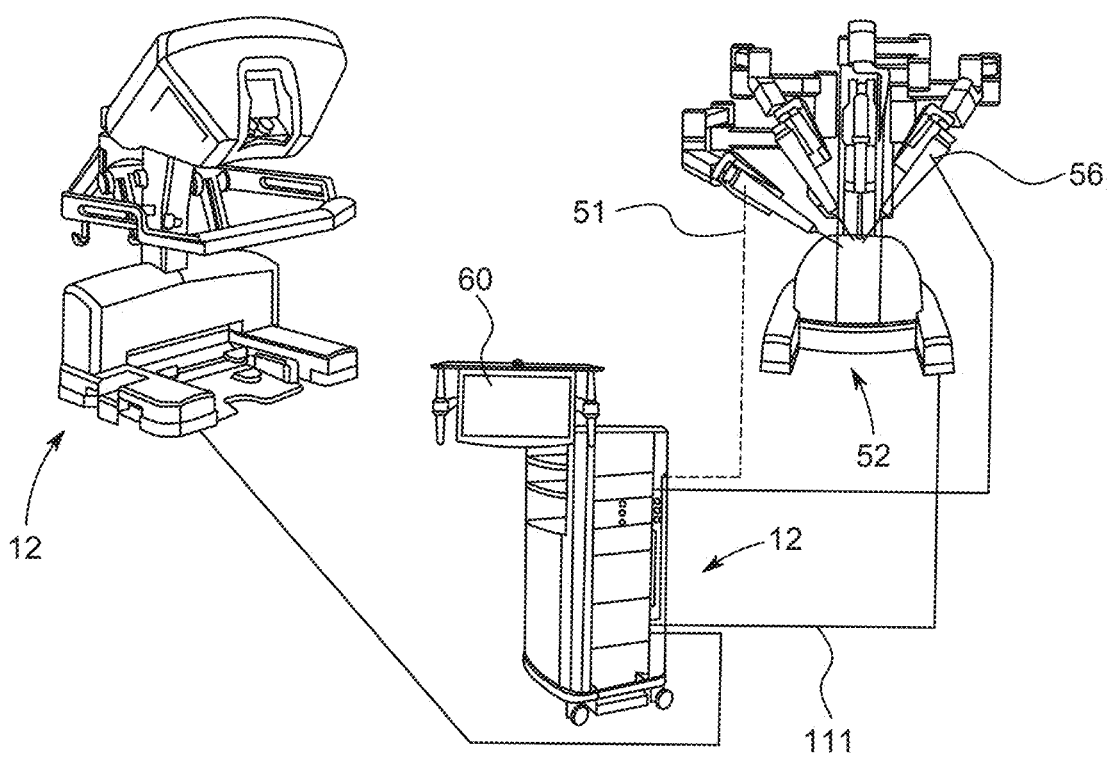
FIG. 7 illustrates one embodiment of a block diagram of a second robotic surgery system to perform robotic surgical procedures of the present invention.
Figure 8:
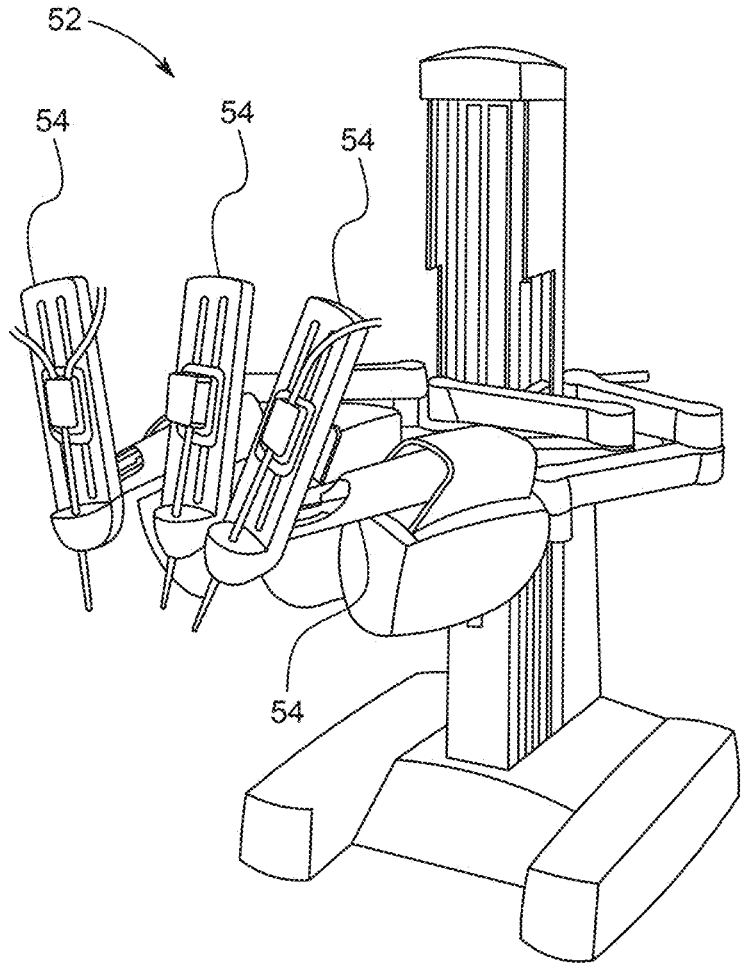
FIG. 8 illustrates one embodiment of a robotic surgical manipulator with a plurality of robotic surgical arms of the present invention.

As a non-limiting example, illustrated in FIGS. 6 through 8, a surgeon, designated as O) performs surgical procedures on patient P by manipulating input devices at the surgeon consol 12, In one embodiment, a computer 151, described hereafter, of consol 12 directs movement of robotically controlled endoscopic surgical instruments 18, causing movement of instruments 18 using the robotic surgical manipulator, e.g., the patient consol 16.

In one embodiment, computer 151 includes one or more processors 62 that interpret movements and actuation of master controllers, (and other inputs the surgeon and assistant, to generate control signals that can control surgical instruments 18 at the surgical site. As a non-limiting example, computer 151 and vision consol 240 map the surgical site into the controller so it feels and appears to the surgeon operator that the master controllers are working over the surgical site.

As a non-limiting example, viewer vision consol 240 has one or more displays where images of a surgical site are viewed. In one embodiment, a viewer is provided that includes left and right display devices. In one embodiment, a three-dimensional perspective is provided, with the viewer including stereo images for each eye including a left image and a right image of the surgical site including any robotic surgical in a left viewfinder and a right viewfinder. The display devices 24 can be pairs of cathode ray tube (CRT) monitors, liquid crystal displays (LCDs), or other type of image display devices 24 (e.g., plasma, digital light projection, etc.). In one embodiment, the images are provided in color by a pair of color devices 452 L, 452 R (24); such as color CRTs or color LCDs.

In one embodiment, patient consol 16 has one or more robotic arms 54, including three or more that can be supported by linkages, with a central arm supporting an endoscopic camera 56 (46) and the robotic surgical arms 54 to left and right of center supporting tissue manipulation surgical instruments 18.

As a non-limiting example, patient consol 16 includes robotic arms 54 and instruments, and is positioned alongside patient table. In one embodiment, the has four arms, and robotic instruments 18 with articulating joints near the tip that allow for wristed movement. As a non-limiting example, this can provide a number of degrees of freedom of movement for surgical tasks, including but not limited to suturing, dissection. A variety of different robotic instruments 18.

In one embodiment, robotic surgical system 10 includes a plurality of robotic arms 54, such as four robotic arms 54 coupled to a mount of the patient consol 16. In one embodiment, a Visualization Device 58, described in greater detail hereafter, is coupled to any of the robotic arms 54 through a robotic trocar, providing optimized visualization of the surgical site. In one embodiment, the mount is used to provide laser targeting and improved anatomical access from almost any position In one embodiment, an assistant provides pre-positioning of patient consol 16 relative to patient P as well as swapping surgical instruments 18 for alternative surgical instruments 18 while viewing the internal surgical site via an assistant's display 60. The image of the internal surgical site shown to A by the assistant's display 60 and surgeon O by surgeon's consol 12 is provided by one of the surgical instruments supported by patient consol 16. In one embodiment, robotic arms 54 include a positioning portion and a driven portion.

In one embodiment, the surgeon receives an image of an internal surgical site at display 24, and/or and assistant O by surgeon's consol 12 is provided by one of the surgical instruments 18 supported by patient consol 16. Real time image recognitive can be used with end effectors 48 including, without limitation, robotic grippers 68 also known as (550), cutting instruments, (scalpels), cannulas, reamers, rongeurs, scissors, drills, bits, or the like. The degrees of freedom, sizes, and functionalities of end effectors 48 can be selected based on the procedure to be performed. For example, one end effector 48 can be used to cut and remove bone and another end effector 48 can be used to remove cartilage, discs, or the like. A variety of end effectors 48 can be used to perform a surgical procedure according to the surgical plan.

In one embodiment, robotic surgical system 10 takes an image of an area to be worked on in this step in the surgery, and sends that image through an image recognition system with image recognition database 34. If the desired tissue type is identified by robotic surgical system 10, the progress through the surgical step may be calculated by comparing the number of layers of tissue affected by surgical robot 20 in the current procedure to the average number of layers effected to complete this surgical step in statistically similar patients who had the same procedure. That progress is displayed for the surgeon, the tissue is affected as prescribed in the surgical plan and the process repeats until the desired tissue type is not identified by the image recognition system with image recognition database 34. When the desired tissue type is not identified, surgical robot 20 stops its progress and the image is presented to the surgeon to define. If the surgeon defines the tissue as the desired type, the identified image library in the image recognition database 34 is updated and surgical robot 20 proceeds.

In some embodiments, system 10 obtains view, images of a selected site, which can be one or more images of a region of interest, and the images can be sent to image recognition system with image recognition database 34. The images can be still images or video. If a targeted tissue is identified by robotic surgical system 10, a surgical plan can be generated.

The targeted tissue can be identified using a comparison images to reference images. The comparison can be used to identify tissue to be removed, determine when a procedure is completed, and the like.

In some embodiments, the targeted tissue can be identified by comparing the number of layers of tissue affected by surgical robot 20 in the current procedure to reference data (e.g., the average number of layers effected to complete this surgical step in statistically similar patients who had the same or similar procedure), That progress is displayed for the surgeon, the tissue is affected as prescribed in the surgical plan and the process repeats until the targeted tissue has been removed. The progress can stop the image is presented to the surgeon to define. If the surgeon defines the tissue as targeted tissue, the identified image recognition library in the image with image recognition database 34 is updated and the surgical robot 20 proceeds. This process can be applied to each individual step in the spinal surgery process as detailed herein.

As a non-limiting example, surgeon consol 12 can include a viewer, including but not limited to Visualization Device 58, that can be a stereo viewer, with one or more sensors, as set forth below. In one embodiment, when the head is not positioned in the surgeon consol 12, robotic surgical system 10 is deactivated and robotic arms 54 are locked in place. As a non-limiting example, the use of two master controllers provides that a surgeon's hand movements are processed by a computer 151 and sent to patient consol 16. In one embodiment, patient consol 16 controls the robotic instruments 18 inside the patient's body in real time. Motion scaling can be performed to filter out physiologic tremor, allowing for finer movements.

In one embodiment, processing by a computer 151 allows for intuitive motion. A movement of the surgeon's hands is translated to the movement of the instruments 18.

As a non-limiting example, adjustments to robotic surgical system. 10, including but not limited to camera 46 control, scope setup, audio volume, consol ergonomics, and the like, are made while the surgeon is seated at surgeon consol 12. Surgeon consol 12 can also toggle between robotic arms 54. In one embodiment, this is achieved with the use of surgeon consol hand and foot pedal 68 controls, as more fully set forth below. As a non-limiting example, surgeon consol 12 is connected to the vision consol 240 and patient consol components via cables.

In some embodiments, robotic surgical system 10 includes a computer 151, computing system, for at least partially controlling robotic surgical apparatus 20 to perform surgical actions by obtaining a first image of a region of interest associated with a subject. A type of tissue shown in the first image can be identified based, at least in part, on a neural network model trained on an image training set. In response to determining that the identified type of tissue belongs to a set of targeted types, causing the robotic surgical apparatus 20 to perform a first surgical action with respect to the region of interest in accordance with a surgical plan. A second image of the region of interest can be obtained after completion of the first surgical action. Additionally surgical steps can be performed.

A computer-readable storage medium storing content that, when executed by one or more processors 62, causes the one or more processors 62 to perform actions including obtaining first image of a region of interest associated with a surgery subject, and identifying a type of tissue shown in the first image based, at least in part, on a neural network model. In response to determining that the identified type of tissue belongs to a set of targeted types, robotic surgical apparatus

20 performs a first surgical action with respect to the region of interest in accordance with a surgical plan. A second image of the region of interest is obtained after completion of the first surgical action. The actions can include displaying types of tissue comprises displaying one or more boundary indicators for indicating at least one of targeted tissue to be removed, protected tissue, delivery instrument 18 placement, or an end effector 48 working space within the subject.

In one embodiment, robotic surgical system 10 provides three-dimensional magnified with vision consol 240. As a non-limiting example, a binocular telescopic camera 46 lens system is coupled to a high-resolution 3DHD camera 46, which can be Visualization Device 58 camera 46. As a non-limiting example, the two are held on the main robotic manipulator arm 54. In one embodiment, system 10 includes a Visualization Device 58 camera 46 with one or more digital image sensors positioned at a distal end of Visualization Device 58 camera 46. In one embodiment, digital image information is transmitted to one or more image processors. The binocular images are translated by computer 151 into a magnified 3D image when viewed at the surgeon consol As a non-limiting example, the scope, Visualization Device camera 46 (58), can be 12 mm (Si) or 8 mm in diameter.

FIG. 7 illustrates robotic surgical system 10 and a method of utilizing AI to complete specific steps in a minimally invasive surgery, according to an embodiment.

Figure 9:
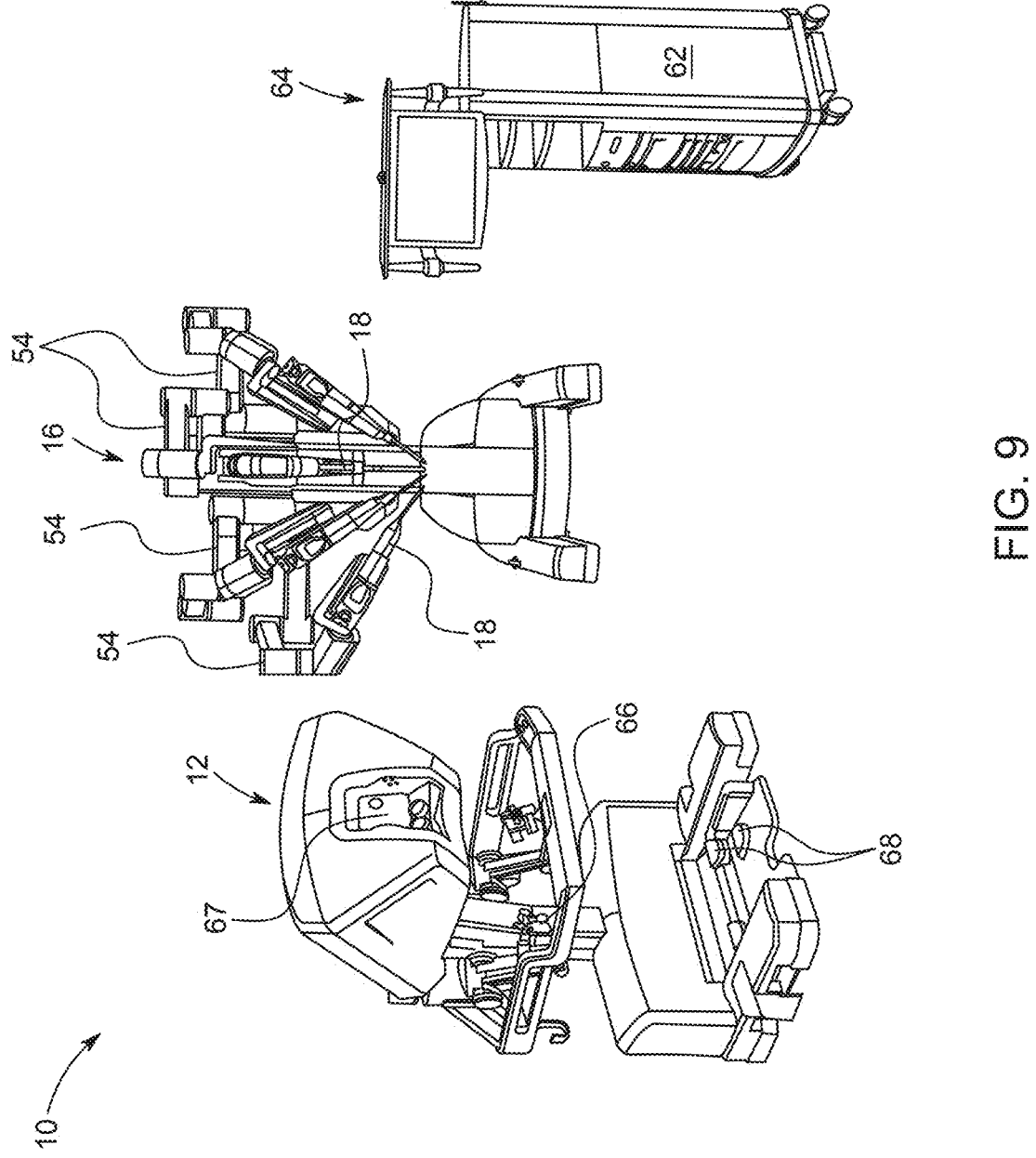
FIG. 9 illustrates one embodiment of a teleoperated surgical system of the present invention.

As a non-limiting example, illustrated in FIG. 9, signal(s) or input(s) are transmitted from surgeon consol 12 as well as to one or more processors 62 at a surgeon consol 12 and/or at control cart 64, which may interpret the input(s) and generate command(s) or output(s) to be transmitted to the patient consol 16 to cause manipulation of one or more of surgical instruments 102 and/or patient side manipulators (arms) 54 which the surgical instruments 18 are coupled at the patient consol 16, robotic surgical system 10 components in FIG. 9 are not shown in any particular positioning and can be arranged as desired, with the patient consol 16 being disposed relative to the patient so as to affect surgery on the patient, In one embodiment, surgeon consol 12 receives inputs from a user, including but not limited to a surgeon or associate, by various input devices, including but not limited to, grippers 66 (550), such as gripping mechanisms 66 (550) and foot pedals 68, and serves as a master controller by which surgical instruments 18 mounted at the patient consol 16 act as slaves to implement the desired motions of the surgical instrument(s) 18, and accordingly perform the desired surgical procedure. In one embodiment, grippers 66 (550) may act as master devices that may control the surgical instruments 18, which may act as the corresponding "slave" devices at the manipulator arms 54, and in particular control an end effector 48 and/or wrist of the instrument. In one embodiment, foot pedals 68 may be depressed to provide a variety of different actions, including but not limited to, suction, irrigation, etc.) at the instruments 18.

As a non-limiting example, output units may include a viewer or display, described in greater detail hereafter that allows the surgeon to view a three-dimensional image of the surgical site, including but not limited to during the surgical procedure, with Visualization Device 58 at patient consol 16.

In one embodiment, surgeon consol 12 includes input devices that a surgeon can manipulate to transmit signals to actuate surgical instruments 18 that can be mounted at arms 54 at the patient consol 16. The surgeon consol 12 can have output devices providing feedback to the surgeon. Surgeon consol 12 can include a unit that integrates the various input and output devices, with, for example, a display, but also can include separate input and/or output devices that are in signal communication with the controllers, such as controllers provided at the surgeon consol and accessible by a surgeon, although not necessarily integrated within a unit with various other input devices. As an example, input units may be provided directly at the surgeon consol 12 and may provide input signals to a processor at the control cart. As a non-limiting example, surgeon consol 12 does not necessarily require all of the input and output devices to be integrated into a single unit and can include one or more separate input and/or output devices.

Figure 10:
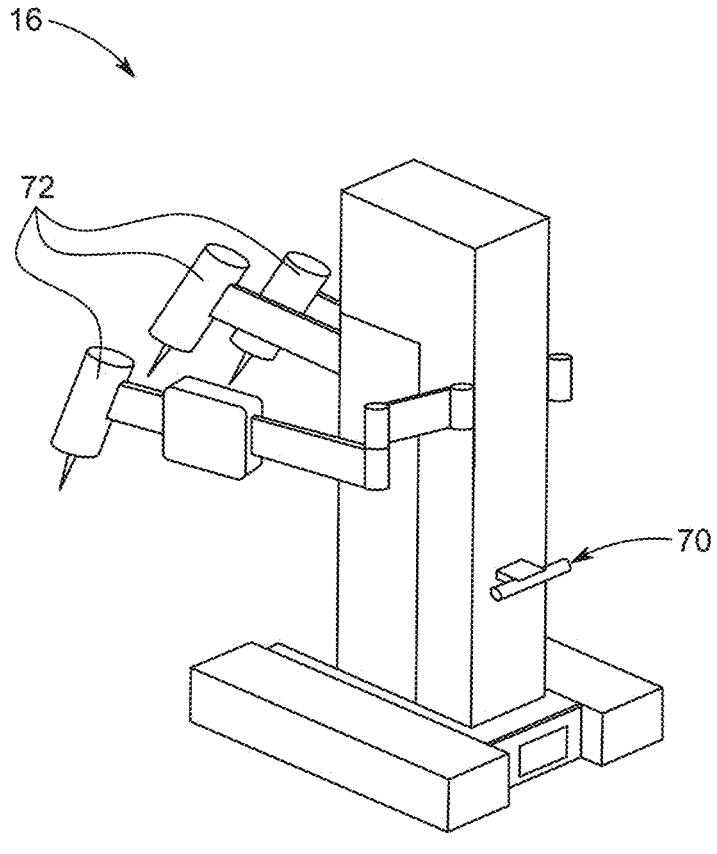
FIG. 10 illustrates one embodiment of a patient side cart that includes a steering interface of the present.

In one embodiment, patient consol 16 can have a teleoperated surgical steering interface 70, FIG. 10. In one embodiment, steering interface 70 detects forces applied by surgeon or assistant to steering interface 70 that provides a signal to a controller of a drive system 80 of patient consol 16, causing it to be driven and steered.

Steering interface 70 can be coupled to a rear of a patient consol 16 with one or more manipulator arms 72. Information received at steering interface 70 can be by drive system 80 to provide motive force to one or more transportation mechanisms of patient consol 16.

Figure 11:
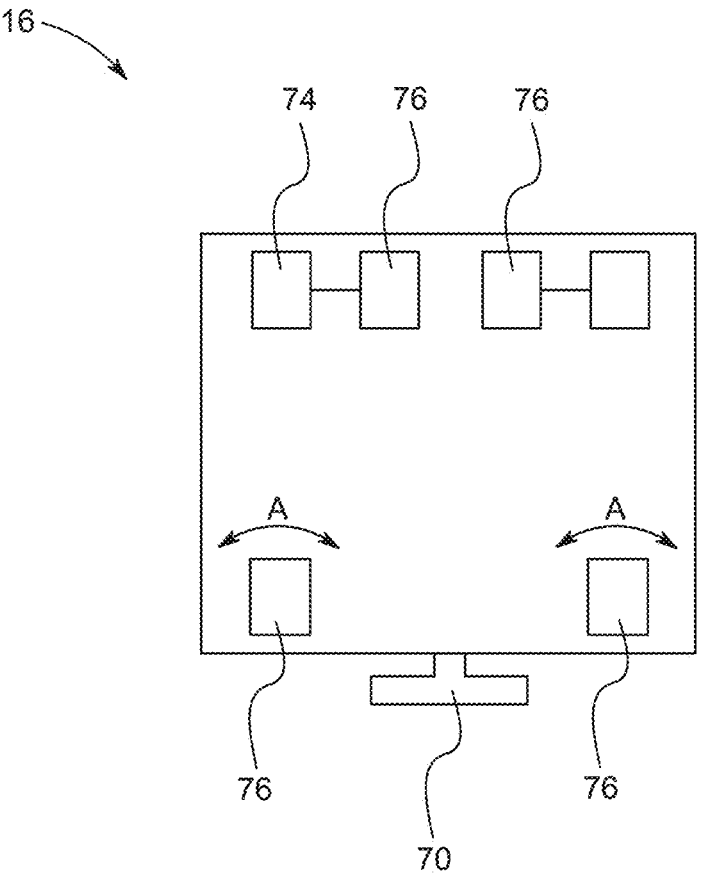
FIG. 11 illustrates one embodiment of a wheel arrangement of a patient side cart with a steering interface of the present invention.

Referring to FIG. 11, one or more wheels of a patient side cart 16 may be driven. In one exemplary embodiment, the front wheels 74, of a patient consol 16 may be driven while rear wheels 76 are not driven. In one embodiment, driven wheels are individually driven by separate motors.

Figure 12:
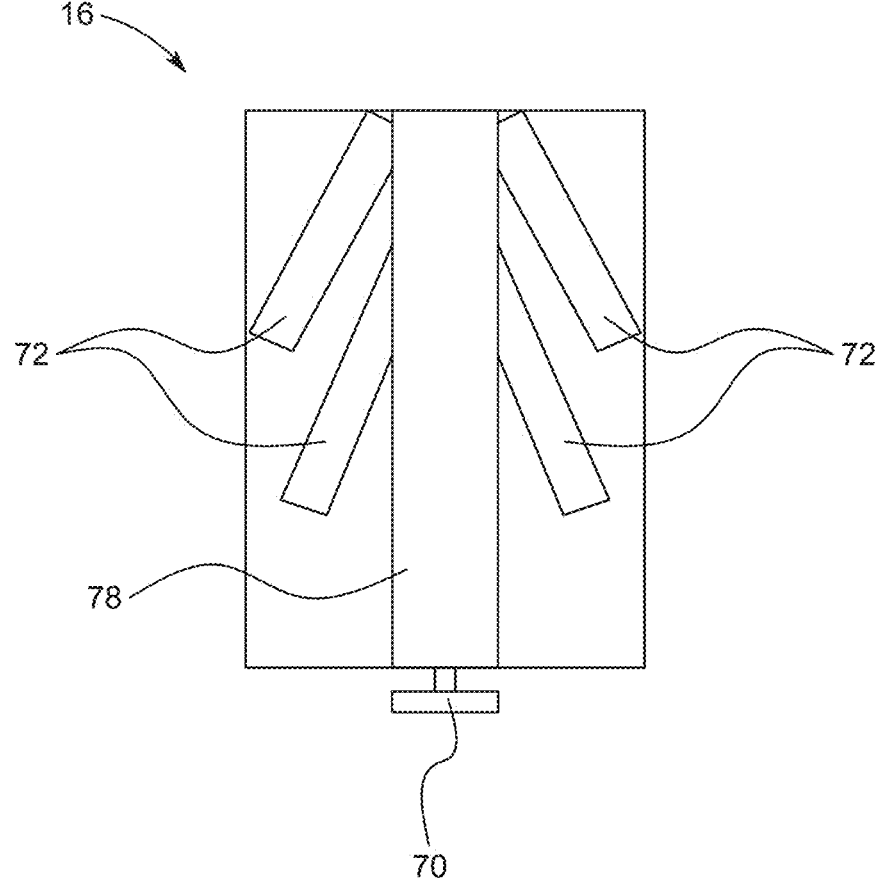
FIG. 12 illustrates one embodiment of a patient side cart in a stowed configuration of the present invention.

As illustrated in FIG. 12, patient control 16 includes steering interface 70 and a plurality of manipulator arms 72 that are configured to hold surgical instruments 18, tools, and the like, the manipulator arms 72 can be folded into a relatively compact arrangement toward a center of the patient consol 15. As a non-limiting example, a post 78 where manipulator arms 72 can be positioned in a non-extended, compact configuration, As a non-limiting example, patient consol 16 includes a drive system 80 configured to receive signal(s) from steering interface 70. In one embodiment, steering interface 70 includes one or more sensors. Patient consol 16 can include a control system or controller, which is part of the drive system 80 or a separate device or system in communication with the drive system. Robotic surgery control system 22 can be configured to receive signal(s) or input(s) from steering interface 70 of patient consol 16. In response to received input(s), steering interface 70 can issue one or more command outputs or outputs to control the driven wheel(s) 76.

Figure 13:
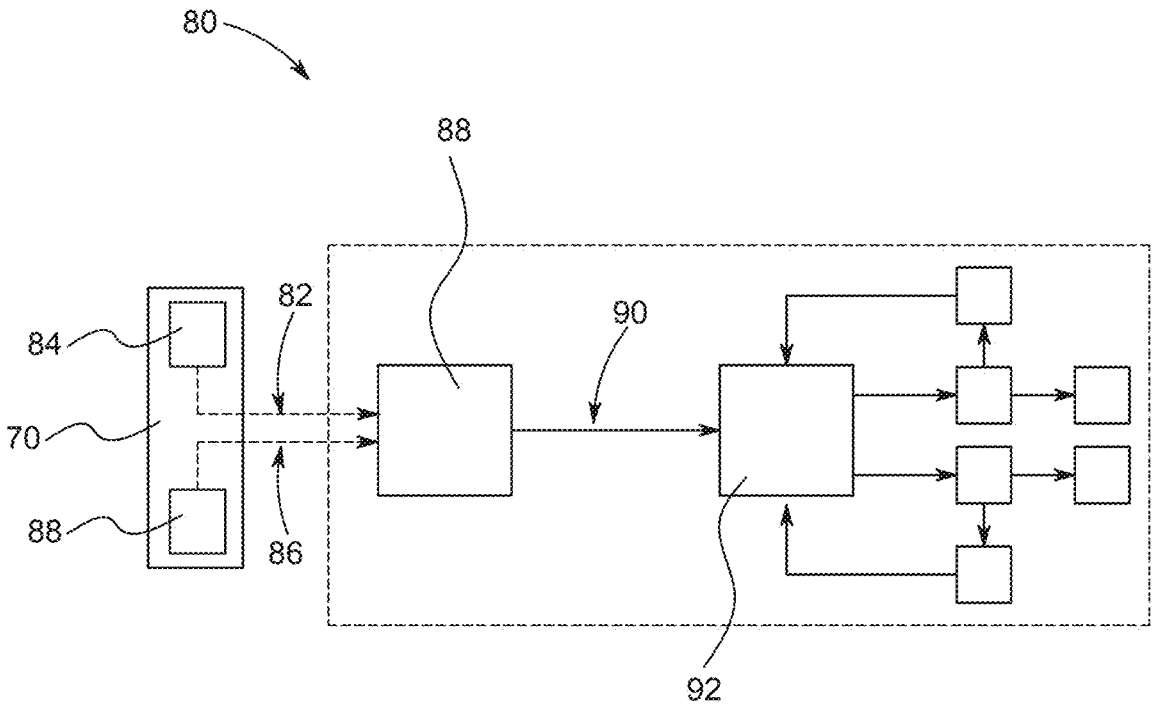
FIG. 13 illustrates one embodiment of a drive system for a patient side cart of the present invention.

Referring to FIG. 13, a drive system 80 for patient consol 16 is shown in communication with a steering interface 70. Steering interface 70 transmits a first input or signal 82 from the first sensor 84 and a second input or signal 86 from a second sensor 88, which are received by the drive system 80.

Drive system 80 can include a signal conditioner 88 and one or more devices. As a non-limiting example, signal conditioner 88 includes an amplifier to increase the power of signals 82 and 86. Signal conditioner 88 can include an analog-to-digital converter to convert analog signals 82 and 86 to a digital form for further processing. As a non-limiting example, signal conditioner 88 includes these devices in combination with one another. Once signals 82 and 86 have been conditioned by signal conditioner 88, the signals are sent via a high speed communication connection 90 to other components of the drive system 80, Drive system 80 can include a control system 94 or controller 92.

Figure 14:
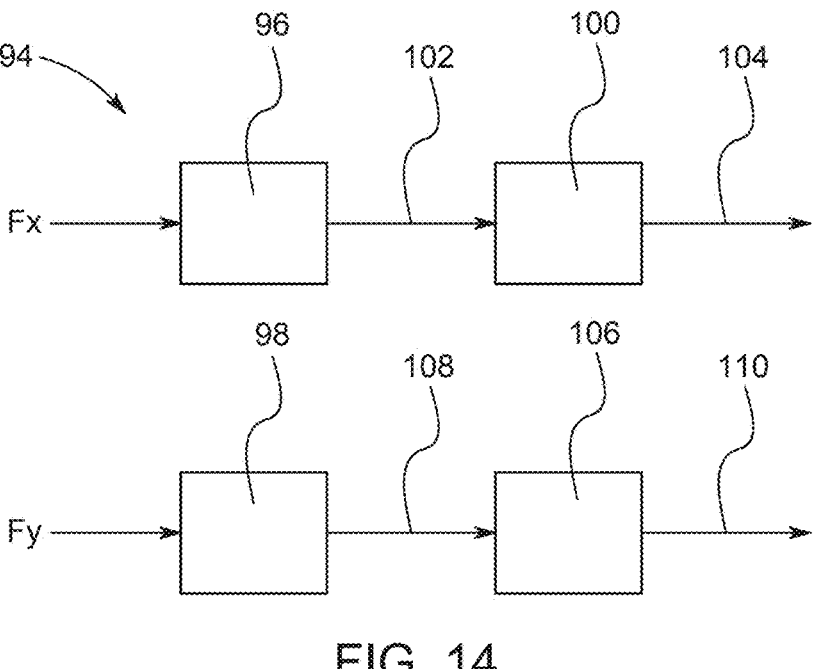
FIG. 14 illustrates one embodiment of a control system of a drive system for a patient side cart of the present invention.

In FIG. 14 illustrates a schematic block diagram of a control system 94 for drive system 80. As a non-limiting example, control system 94 receives one or more inputs or signals from steering interface 70. Control system 94 may include a first control module 96 and a second control module 98.

Control system 94 may include a fore/aft model section or module 100 configured to receive a desired raw fore/aft movement signal or input 102, analyze the signal, and issue or transmit a fore/aft command output 104 corresponding to the desired movement. Fore/aft command output 102 that is a command output to a motor to drive a driven wheel and produces a desired fore/aft movement. For instance, fore/aft command output 104 is in the form of a force or a torque command for a motor that drives a driven wheel. Control system 94 can include a yaw model section or module 106 to receive a desired raw yaw signal or input 108, analyze the signal, and issue or transmit a yaw rate command output 110 corresponding to the desired yaw rate for turning a patient side cart In one embodiment, a feedback portion of control system 94 measures output 108 of the driven component 98, such as a velocity, acceleration, and/or yaw rate. For example, a sensor may be configured to detect the velocity, acceleration, and/or yaw rate of one or more driven wheels or of patient consol 16.

Figure 15:
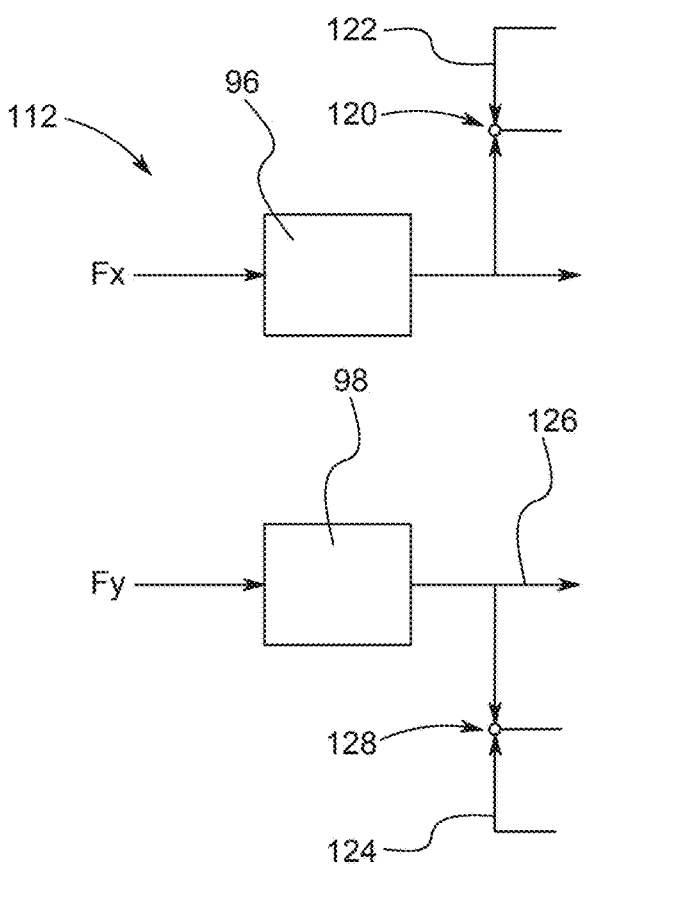
FIG. 15 illustrates one embodiment of another embodiment of a control system for a patient side cart that includes feedback control of the present invention.

FIG. 15 illustrates feedback control. Control system 112 can be used as control system 94 of FIG. 14. Feedback control output signals can be provided from patient consol 16 to control System 94. As a non-limiting example, patient consol dynamics section 114 can provide a fore/aft output signal 116 and a yaw rate output signal 118. Output signal 116 is compared with the desired fore/aft movement signal 120, such as at error detector 122, and yaw rate output signal 124 is compared with yaw rate signal 126, such as at error detector 128. Any differences resulting from the comparison at error detectors 122, 128 are sent to feedback control modules 130 and 132. Fore/aft feedback control module 130 produces a fore/aft feedback command output 134, which is combined with the fore/aft command output 136, such as at adder 138, to provide a corrected fore/aft command output 140, which is in turn sent to patient consol section 114. Yaw feedback control module 132 produces a yaw rate feedback command output 142, which is combined with the yaw rate command output 144, such as at adder 146, to provide a corrected yaw rate command output 148 that is sent to cart dynamics section 114.

Figure 17:
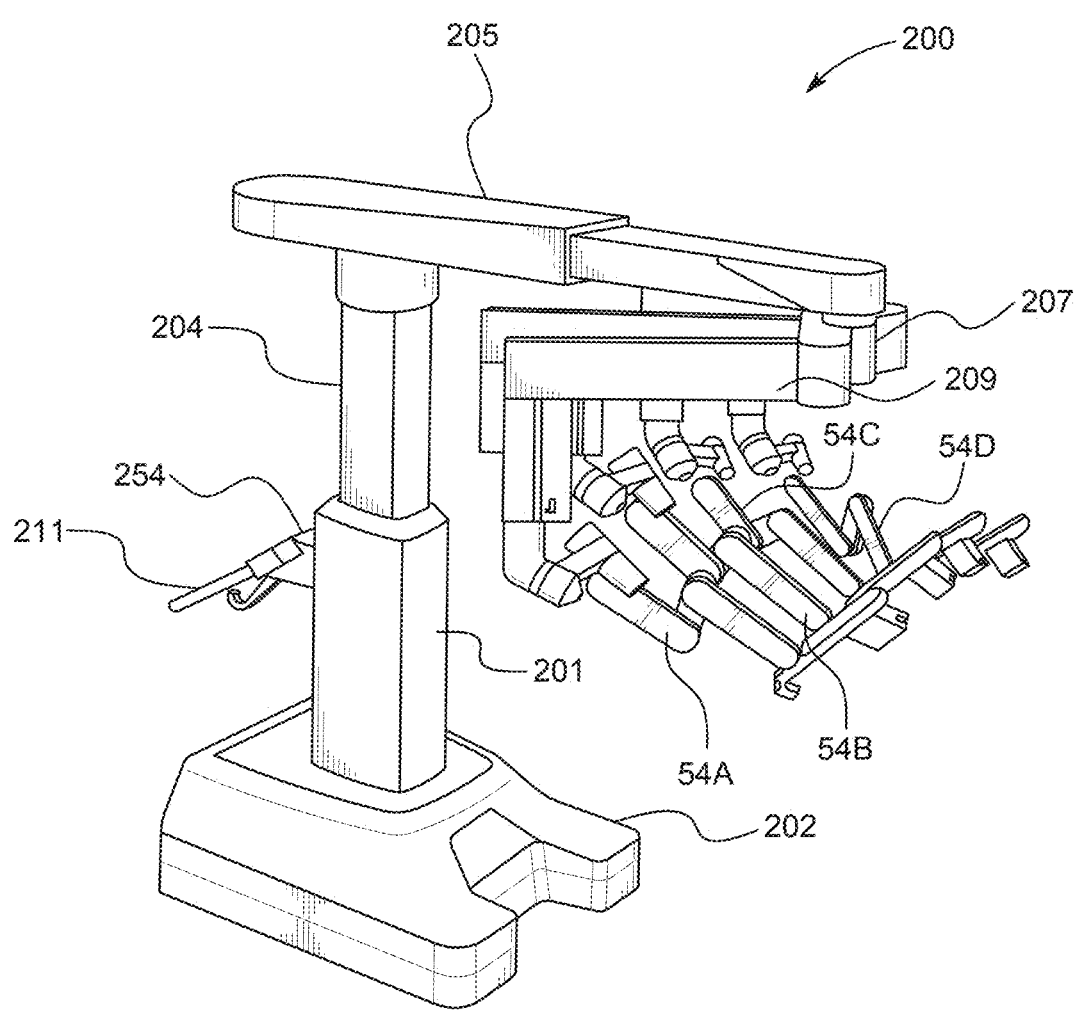
FIGS. 17, 18, 19 illustrate one embodiment of components that can be used with the FIG. 16 robotic surgical system of the present invention.
Figure 20:
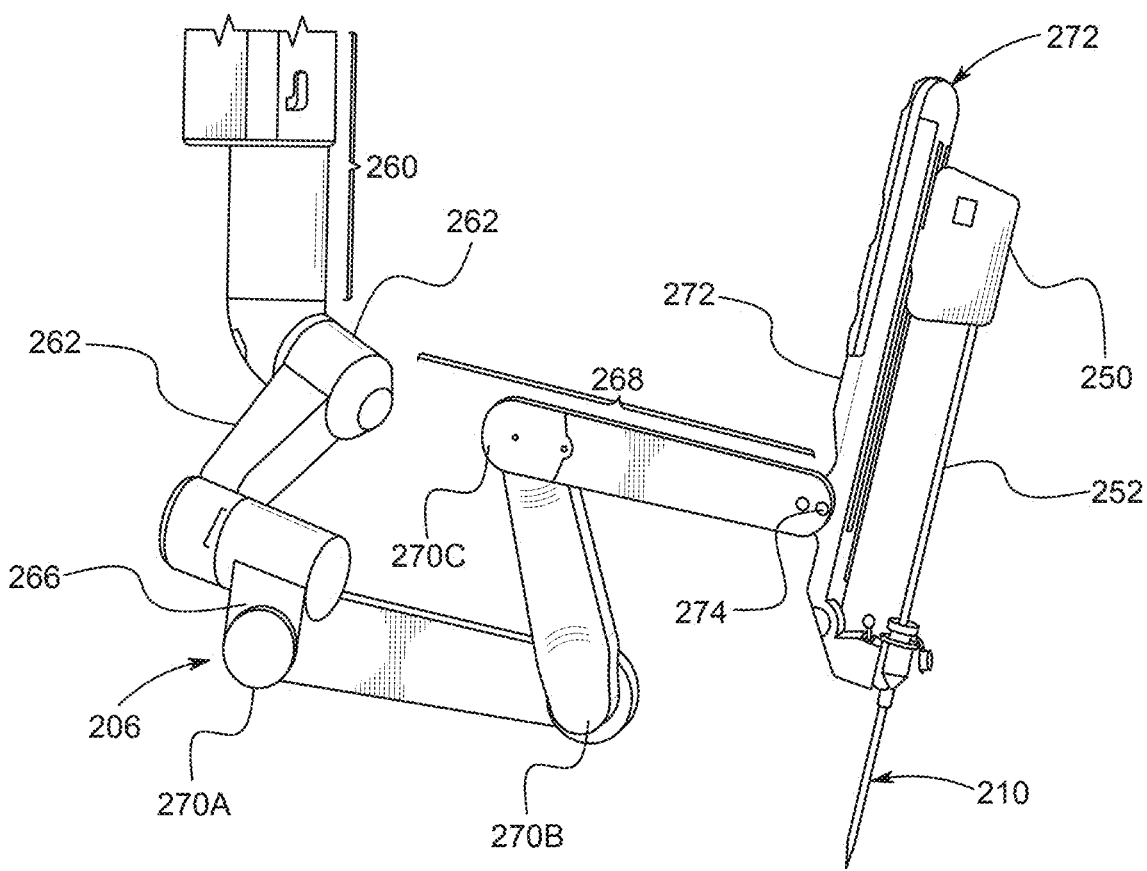
FIG. 20 illustrates one embodiment of an arm of a robotic surgical system of the present invention.

FIG. 20 illustrates an arm of the robotic surgery robotic surgical system of FIG. 17 in one embodiment of the present invention.

Figure 19:
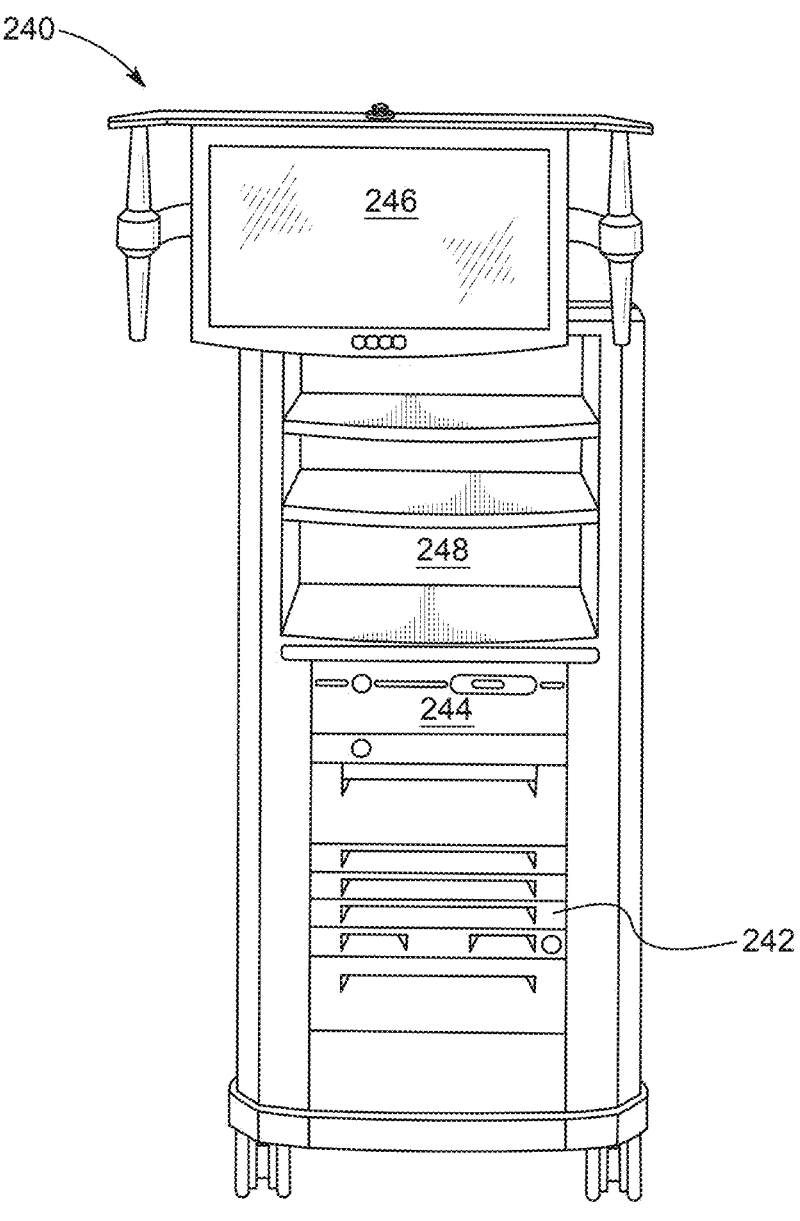

In one embodiment, as illustrated in FIG. 19, vision consol 240 is part of robotic surgical system 10. The vision consol 240 can house robotic surgical system's 10 central electronic data processing unit 242, which can be all or a portion of control system 250 (94), and vision equipment 244. In one embodiment, a central electronic data processing unit 222 includes much of the data processing used to operate robotic surgical system 10. In one embodiment, electronic data processing can be provided through surgeon consol 12 and tele-operational assembly 200. As a non-limiting example, vision equipment 244 can include camera 46 control units for the left and right image capture functions of Visualization Device 58. The vision equipment 244 may also include illumination equipment that provides illumination for imaging the surgical site. In one embodiment, vision consol 240 includes an optional touchscreen monitor 246, which may be mounted elsewhere, such as on the assembly 200 or at patient consol 16. In one embodiment, vision consol 240 includes space 248 for auxiliary surgical equipment. As a non-limiting example, a teleoperated robotic surgical system 10 can include an intuitive telepresence for the surgeon.

In one embodiment, a control system 150 (94) is operatively linked to s touchpad, sensors, motors, actuators, encoders, hydraulic flow systems, and other components of the robotic surgical system 12. In one embodiment, robotic surgical system includes one or more teleoperational systems 200.

Figure 16:
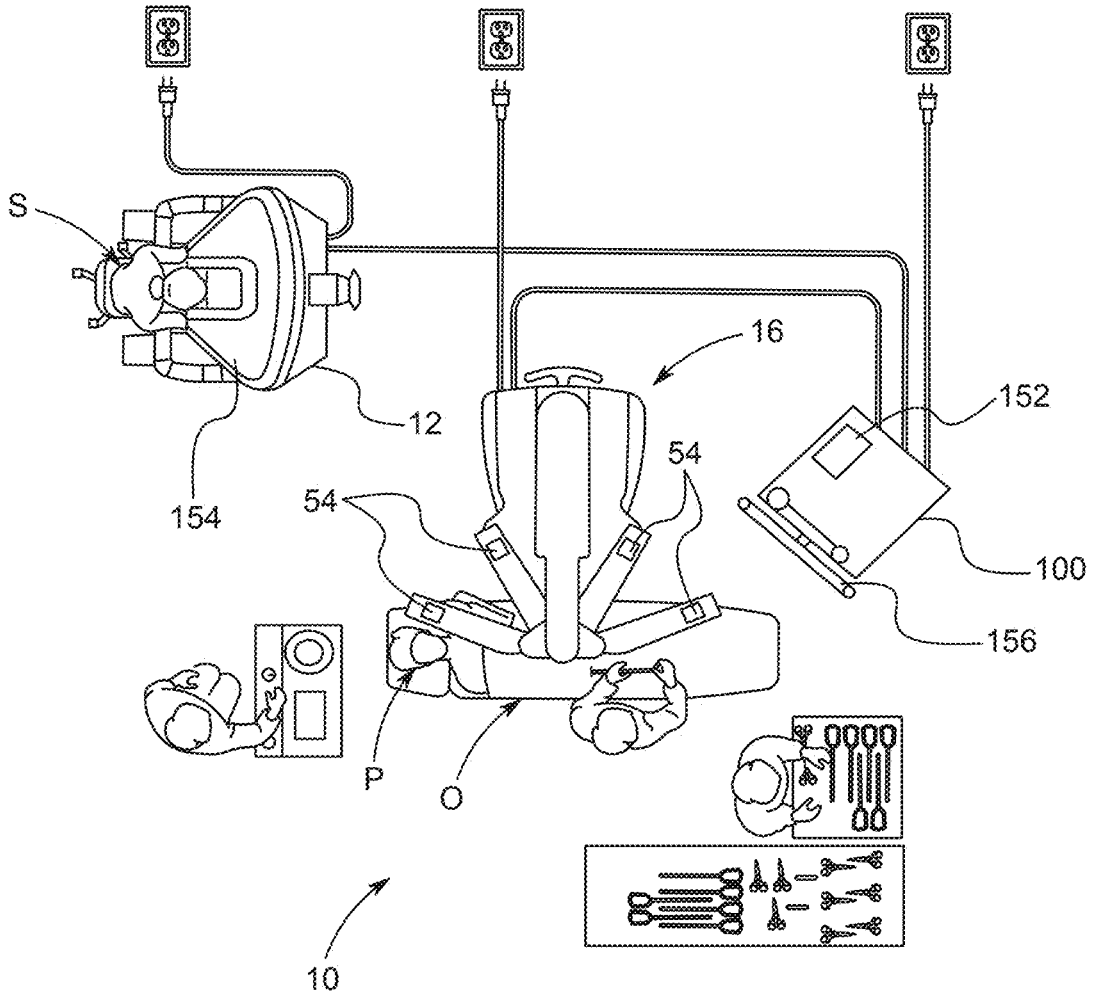
FIG. 16 illustrates one embodiment of a robotic surgical system of the present invention.

Referring to FIG. 16, control system 150, such as control system 94 of FIG. 14, includes one or more memories and processors 62, providing control between system 10, which can be tele-operational robotic surgical system 10, surgeon consol 12, patient consol 16 which provides surgeon input, image capture system 152 and a display system 154 (24). All are coupled together, which be by tele-operationally. As a non-limiting example, control system 150 can include programmed instruction, such as a computer-readable medium storing the instructions). While control system 150 is shown as a single contained element, robotic surgical system 10 can include two or more data processing circuits with one portion of the processing optionally being performed on or adjacent the teleoperational assembly 200. In one embodiment, centralized or distributed data processing architectures are used. As a non-limiting example, programmed instructions of surgical computing device 151 are provided as a number of separate programs or subroutines, or they may be integrated into a number of other aspects of the teleoperational systems 200. As a non-limiting example, control system 150 supports wireless communication protocols such as Bluetooth, IrDA, Home RF, IEEE 802.11, DECT, and Wireless Telemetry.

In one embodiment, robotic surgical system 10 includes a vision system 156 coupled with optical fiber communication links to surgeon counsel 12.

As a non-limiting example, control system 150 includes at least one memory and at least one processor (not shown) for effecting control between systems and elements of robotic surgical system 10. As a non-limiting example, control system 150 includes programmed instructions of surgical computing device 151 (e.g., a computer-readable medium storing the instructions) to implement some or all of the robotic surgical system procedures and implementations. Programmed instructions of surgical computing device 151 can be provided with a number of separate programs or subroutines, or they may be integrated into a number of other aspects of robotic surgical system 10. As non-limiting examples, control system 150 supports wireless communication protocols such as Bluetooth, IrDA, HomeRF, IEEE 802.11, DECT, and Wireless Telemetry.

In one embodiment, control system 150 includes a surgeon or assistant interface configured to receive information from and convey information to a surgeon and assistants. As a non-limiting example, the surgeon or assistant interface can be a touchscreen monitor that may present prompts, suggestions, and status updates. In one embodiment, the touchscreen monitor is in a position in the operating room where it can be easily seen as the surgeon and assistants. In various embodiments, other interfaces can be used, including but not limited to: one or monitors or display screens 24, a keyboard, a computer mouse, rollers, buttons, knobs, and other user interfaces.

In some embodiments, control system 150 may include one or more servo controllers that receive force and/or torque feedback from the robotic surgical system 10.

In response to feedback, servo controllers transmit signals to surgeon and patient's consols 12 and 16, respectively. The servo-controller(s) can transmit signals instructing robotic surgical system 10 to move instruments 18. As a non-limiting example, any suitable conventional or specialized servo controller is used. The servo controller can be separate from, or integrated with, robotic surgical system 10.

In one embodiment, robotic surgical system 10 includes optional operation and support systems (not shown) such as illumination systems, steering control systems, eye tracking systems, fluid management systems such as irrigation systems and/or suction systems. In alternative embodiments, robotic surgical system 10 has more than one teleoperational assembly and/or more than one operator input system. The exact number of manipulator assemblies will depend on the surgical procedure and the space constraints within the operating room, among other factors. The operator input systems may be collocated or they may be positioned, in separate locations. Multiple operator input systems allow more than one operator to control one or more manipulator assemblies in various combinations, FIG. 17 illustrates one embodiment of a teleoperational assembly 200 (e.g., the teleoperational assembly 200 shown in FIG. 16. The assembly 200 includes an automated and motorized setup structure that supports projecting arms, and may include a base 202 that rests on the floor, a telescoping support column 204 that is mounted on the base 202, a telescoping boom 205 that extends from the support column 204, and a platform portion as an orienting platform 207, The assembly 200 also includes support beams 209, and several arms 54 that support surgical (including portions of the image capture system 152). As shown in FIG. 17, arms 54(a), 54(b), 54(c), 54(d), such as arms 54, are instrument arms that support and move the surgical instruments used to manipulate tissue. One of these arms 54 may be designated as a camera 46 arm that supports and moves Visualization Device 58, shows one of the arms 54 with an interchangeable surgical instrument 210 mounted thereon. The surgical instrument may be Visualization Device 58 mounted on the arm 54 designated as the camera 46 arm. Visualization Device 58 may be a stereo Visualization Device 58 for capturing stereo images of the surgical site and providing the separate stereo images to the display system 24. In one embodiment, arms 54 that support surgical instruments 18 and the camera 46 may also be supported by a base platform (fixed or moveable) mounted to a ceiling or wall, or in some instances to another piece of equipment in the operating room (e.g., the operating table), two or more separate bases may be used (e.g., one base supporting each arm 54).

Figure 18:
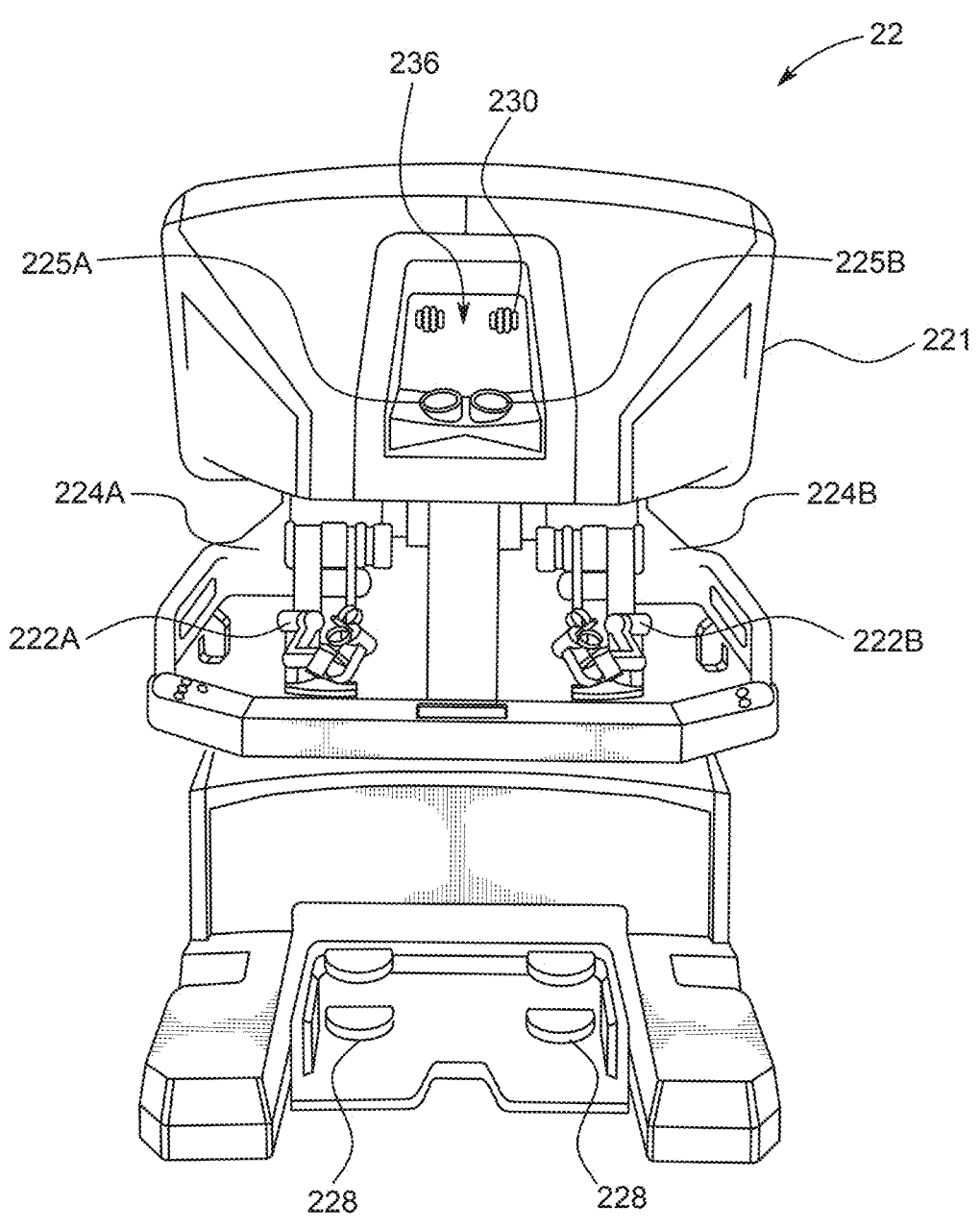

As is further illustrated in FIG. 20, instrument 200 includes an instrument interface 250 and an instrument shaft 252. In some embodiments, the teleoperational assembly 200 may include supports for cannulas that fix the instrument 210 with respect to the cannulas. In some embodiments, portions of each of the instrument arms 54 may be adjustable by personnel in the operating room in order to position the instrument with respect to a patient. Other portions of the arms 54 may be actuated and controlled by the operator at an operator input system 220 (as shown in FIG. 18. The surgical instrument 210 associated with each arm 54 may also be controlled by the operator at the operator input system 220.

In more detail, the arm 54 includes a vertical setup 260 connected via a setup joint 262 to a distal-most setup link 264. A yaw joint 266 connects the distal-most setup link 262 to a parallelogram pitch mechanism 268. The parallelogram pitch mechanism 264 includes a plurality of pitch joints

270(*a*), 270(*b*), 270(*c*) enabling it move. A spar 272 connects to the parallelogram pitch mechanism 264 at a spar joint 274. Each of the setup joint 262, the yaw joint 266, the pitch joints 270(*a*), 270(*b*), 270(*c*), and the spar joint 274 are controlled by motors, referenced herein as a setup joint motor, a yaw joint motor, pitch joint motors, and a spar joint motor. Accordingly, the arm 54 is configured to move in a completely motorized fashion. In this embodiment, the motors are under the control of the control system 22 (94 and 150) and may be operated with motors of the other arms to take desired poses that may assist with draping, advancing over a patient, docking to surgical instruments, or storage, among others. In addition, encoders and sensors associated with each motor provide feedback to the control system 22 so that the control system senses or detects the position, status, and setup of the arm 54. In some embodiments, the spars 272 include sensors to detect the presence of surgical drapes on the arms 54.

The teleoperational assembly 200 also includes a helm 211 fixed relative to the base 202 on the support, column 204 with a user interface for controlling the setup and operation. In some embodiments, the user interface is a touchpad 254 capable of accepting user inputs and providing graphical, textual, auditory, or other feedback. The touchpad 254 provides features for teleoperational assembly 200 activities such as preparation for draping, docking, or stowing to help the user minimize the space it takes up in the OR. The touchpad 254 also provides a means for system fault notification and recovery. In some embodiments, the touchpad 254 is disposed along the support column 204 and is configured to be viewed by a user in the operating room, in other embodiments, the touchpad or other user interface is disposed elsewhere. It may be wired or wireless and may be disposed within bag or elsewhere for sterile use. The touchpad 254 in this embodiment is configured to display informational data relating to status of the teleoperational assembly 200, information relating to particular surgical procedures, and information relating to the overall teleoperational robotic surgical system 10. In some embodiments, the touchpad 254 is a touchpad display interface that presents information and accepts user inputs. As such, a user may input control instructions, including setup instructions, at the touchpad.

FIG. 18 is a front elevation view of an operator input system 220 (e.g., the operator input system 220 shown of FIG. 16. The operator input 220 includes a console 221 equipped with left and right multiple degree-of-freedom (DOE) control interfaces 222 *a* and 222 *b*, which are kinematic chains that are used to control the surgical instruments 210 including Visualization Device 58. The surgeon grasps a pincher assembly 224(*a*), 224(*b*) on each of control interfaces 222, typically with the thumb and forefinger, and can move the pincher assembly to various positions and orientations. When a surgical instrument control mode is selected, each of control interfaces 222 is configured to control a corresponding surgical instrument and instrument arm 54. For example, a left control interface 222 *a* may be coupled to control the instrument arm 54 *a* and its associated surgical instrument 210, and a right control interface 222 *b* may be coupled to the control instrument arm 54 *b* and its associated surgical instrument 210. If the third instrument arm 54 *c* is used during a surgical procedure and is positioned on the left side, then left control interface 222 *a* can be switched from controlling the arm 54 *a* and its associated surgical instrument 210 to controlling the arm 54(*c*) and its associated surgical instrument 210, Likewise, if the third instrument arm 54(*c*) is used during a surgical procedure and is positioned on the right side, then the right control interface 222(*a*) can be switched from controlling arm 54(*b*) and its associated surgical instrument 210 to controlling the arm 54(*c*) and its associated surgical instrument 210. In some instances, control assignments between the control interfaces 222(*a*), 222(*b*) and combination of arm 54 surgical instrument 18, and combination of arm 54 and surgical instrument 18 may also be exchanged. This may be done, for example, if Visualization Device 58 is rolled 280 degrees, so that the instrument moving in the Visualization Device's 58 field of view appears to be on the same side as the control interface the surgeon is moving. The pincher assembly is typically used to operate a jawed surgical end effector 48 (e.g., scissors, grasping retractor, and the like) at the distal end of a surgical instrument 210.

Additional controls are provided with foot pedals 228 (68). Each foot pedal 228 (68) can activate certain functionality on the selected one of instruments 210 (18), For example, foot pedals 228 (68) can activate a drill or a cautery surgical instrument 18 or may operate irrigation, suction, or other functions. Multiple instruments can be activated by depressing multiple ones of pedals 228 (68). Certain functionality of instruments 210 (18) may be activated by other controls.

As a non-limiting example, surgeon's console 12 also includes a stereo image viewer system 226 (e.g., the display system 24. Stereo image viewer system 226 includes a left eyepiece 225(*a*) and a right eyepiece 225(*b*), so that the surgeon may view left and right stereo images using the surgeon's left and right eyes respectively inside the stereo image viewer system 226. Left side and right side images captured by Visualization Device 58 (212) are outputted on corresponding left and right image displays, which the surgeon perceives as a three-dimensional image on a display system (e.g., the display system 24 shown in FIGS. 16 and (24). In an advantageous configuration, the control interfaces 222 are positioned below stereo image viewer system 226 so that the images of the surgical shown in display 24 appear to be located near the surgeon's hands below the display. This feature allows the surgeon to intuitively control the various surgical instruments in the three-dimensional display 24 as if watching the hands directly. In one embodiment, the servo control of the associated instrument arm 54 and instrument is based on the endoscopic image reference frame, The endoscopic image reference frame is also used if the control interfaces 222 are switched to a camera 46 control mode, in some cases, if the camera 46 control mode is selected, the surgeon may move the distal end of Visualization Device 58 (212) by moving one or both of the control interfaces 222 together. The surgeon may then intuitively move (e.g., pan, tilt, zoom) the displayed stereoscopic image by moving the control interfaces 222 as if holding the image in his or her hands, In one embroilment, illustrated in FIG. 18, a headrest 230 is positioned above stereo image viewer system 226. As the surgeon is looking through stereo image viewer system 226, the surgeon's forehead is positioned against headrest 230. In some embodiments of the present disclosure, manipulation of Visualization Device 58 (212) or other surgical instruments can be achieved through manipulation of headrest 230 instead of utilization of the control interfaces 222.

FIG. 19 is a front view of a vision cart component 240 of a surgical system. For example, in one embodiment, the vision cart component 240 is part of robotic surgical system 10 shown in FIG. 16. The vision cart 240 can house robotic surgical system's 10 central electronic data processing unit 242 (e.g., all or portions of control system 22 shown in FIG. 16 and vision equipment 244 (e.g., portions of the image capture system 152 shown in FIG. 16. The central electronic data processing unit 242 includes much of the data processing used to operate the robotic surgical system 10. In various implementations, however, the electronic data processing may be distributed in the surgeon console 12 and teleoperational assembly 200. The vision equipment 244 may include camera 46 control units for the left and right image capture functions of Visualization Device 58 (212). The vision equipment 244 may also include illumination equipment (e.g., a Xenon lamp) that provides illumination for imaging the surgical site. As shown in FIG. 19, vision cart 240 includes an optional touchscreen monitor 246 (for example a 24-inch monitor), which may be mounted elsewhere, such as on the assembly 200 or on a patient side cart. The vision cart 240 further includes space 248 for optional auxiliary surgical equipment, such as electrosurgical units, insufflators, suction irrigation instruments, or third-party cautery equipment. The teleoperational assembly 200 and the surgeon's console 120 are coupled, for example, via optical fiber communications links to the vision cart 240 so that the three components together act as a single teleoperated minimally invasive robotic surgical system 10 that provides an intuitive telepresence for the surgeon.

The touchscreen monitor 246 can form a user interface that provides status and prompts during the guided setup process described herein. While a touchscreen monitor is shown, it is worth noting that other types of user interfaces may be used, including those, described above with reference to the touchpad 254. It is worth noting that some guided setup processes receive no user inputs at the user interface because the robotic surgical system is arranged to sense or otherwise recognize when a setup step is complete. Accordingly, in some embodiments the user interface is merely a display 24 that does not receive user inputs.

As non-limiting examples, some of all of the assembly 200 can be implemented in a virtual (simulated) environment, wherein some or all of the image seen by the surgeon at the surgeon's console 220 can be synthetic images of instruments and/or anatomy, in sonic embodiments, such synthetic imagery can be provided by the vision cart component 240 and/or directly generated at the surgeon's console 220 (e.g., via a simulation module).

In one embodiment, servo control is provided for transferring mechanical motion of masters to manipulator assemblies 220 to 223. As a non-limiting example, servo control provides force feedback and, in some aspects, torque feedback from surgical instruments to the hand-operated masters. Servo control can include safety monitoring controller (not shown) to safely halt robotic surgical system operation, or at least inhibit all surgical robot 20 motion, in response to recognized undesirable conditions, e.g., exertion of excessive force on the patient, mismatched encoder readings, and the like.

A variety of different surgical instruments 18 can be used with robotic surgical system 10. These include but are not limited to: graspers, dissection instruments, scissors, coagulators, clip applicators, needle holders, electric scalpels, suction/irrigation instruments 18, laparoscopic tools, articulated instruments, instruments with actuating rods, and the like.

In certain embodiments, robotic surgical systems 10 can include the measuring of various parameters associated with an end effector 48 before, during, and/or after a surgical action or procedure. The monitored parameters can include rpms, angle, direction, sound, or the like. The monitored parameters can be combined with location data, tissue type data, and/or metadata to train an AI system 42 for guiding surgical instrument 18 to automatically perform a surgical action, procedure, or an entire surgery.

Figures 21A, 21B, 21C:
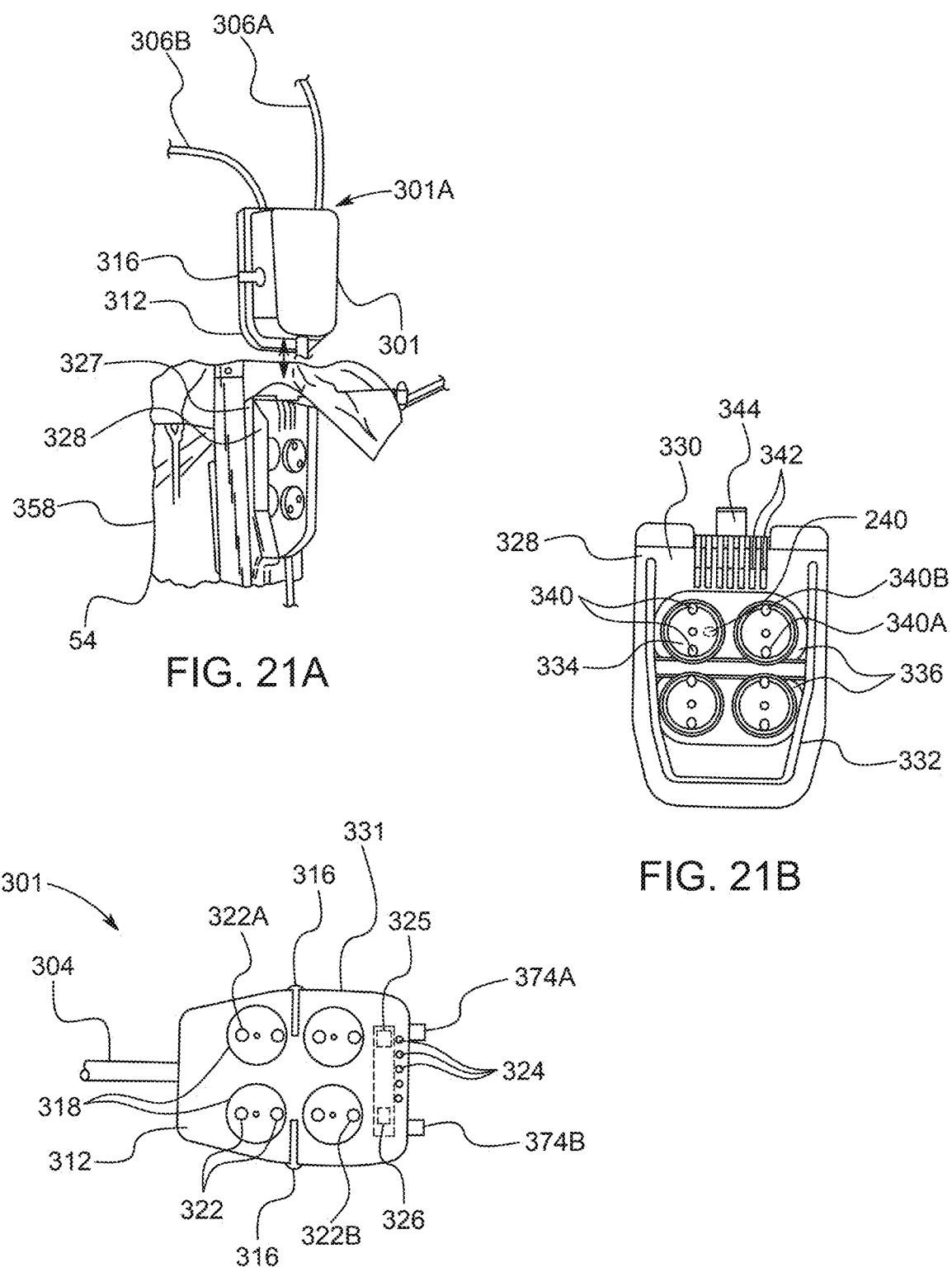
FIG. 21A illustrates one embodiment of mounting of a surgical tool to an adapter of a robotic surgical arm of the present invention.
FIG. 21B illustrates one embodiment of an adapter of a robotic surgical arm for mounting a surgical instrument of the present invention.
FIG. 21C illustrates one embodiment of a surgical instrument that interfaces to a robotic surgical arm of the present invention.

Referring to FIGS. 21A-21C each robotic arm 54 can include a linkage that constrains the movement of the surgical instrument 18. In one embodiment, linkage includes rigid links coupled together by rotational joints in a parallelogram arrangement so that the robotic surgical instruments rotate around a point in space. At the point in space, robotic arm 54 can pivot the surgical instrument 18 about a pitch axis and a yaw axis. The pitch and yaw axes intersect at the point, which is aligned along a shaft of a robotic surgical instrument 18. The shaft is a rotatable hollow tube that may have a number of cables of a cable drive system to control the movement of the end effectors 48 (312).

In one embodiment, robotic arm 54 provides further degrees of freedom of movement to the robotic surgical instrument 18. Along an insertion axis, parallel to the central axis of the shaft of the surgical instrument, the robotic surgical instrument 18 can be configured to slide into and out from a surgical site. Surgical instrument 18 can also rotate about the insertion axis. As surgical instrument 18 slides along or rotates about the insertion axis, the center point is relatively fixed with respect to the patient consol 16. That is, the entire robotic arm is generally moved in order to maintain or re-position back to the center point.

In one embodiment, linkage of the robotic arm 54 is driven by a series of motors therein in response to commands from one or more processors 62 or computer 151. The motors in the robotic arm 54 are also used to rotate and/or pivot surgical instrument 18 at the center point around the axes. If a surgical instrument 18 further has end effectors 48 to be articulated or actuated, still other motors in the robotic arm 54 may be used to control the end effectors 48. Additionally, the motion provided by the motors may be mechanically transferred to a different location such as by using pulleys, cables, gears, links, cams, cam followers, and the like or other known means of transfer, such as pneumatics, hydraulics, or electronics.

In one embodiment, surgical arm 54 can include an adapter 328 or other surgical instruments 18 may be mounted. The front side of adaptor 328 is generally referred to as an instrument side 330 and the opposite side is generally referred to as a holder side (not shown).

As illustrated in FIG. 21b surgical instrument 18 includes a mountable housing 301 including an interface base 312 that can be coupled to adapter 328 to mount surgical instrument 400. The interface base 312 and the adapter 328 may be electrically and mechanically coupled together to actuate the surgical instrument 18. Rotatably coupled to the interface base 312 are one or more rotatable receiving members 318, also referred to as input disks. Each of the one or more rotatable receiving members 318 includes a pair of pins 322a and 322b generally referred to as pins 322. Pin 322(a) is located closer to the center of each rotatable receive member 318 than pin 322(b). The one or more rotatable receiving members 318 can mechanically couple respectively to one or more rotatable drivers 334 of the adapter 328. The surgical instrument 18 may further include release levers 316 to release it from the adapter 328 and the robotic arm.

In one embodiment, interface base 312 can have one or more electrical contacts or pins 324 to electrically couple to terminals of an electrical connector 342 of the adapter 328. The interface base 312 can have a printed circuit board 325 and one or more integrated circuits 326 coupled thereto and to the one or more pins 324. The one or more integrated circuits 326 store surgical instrument information that may be used to identify the type of surgical instrument 18 coupled to the robotic arm, so that it may be properly controlled by the surgeon control console 12.

Referring to FIGS. 21A-21C-, interface or surgical instrument base 312 of the surgical instrument 400 can couple to an adapter 328 so that it is removably connectable to the robotic surgical system 10. Other surgical instruments 18 with the same type of surgical instrument base may also couple to the adapter and then the robotic arm. During surgery, the adapter 328 is coupled to the moveable carriage 337. A surgical instrument 12 can translate with the carriage 337 along an insertion axis of the robotic surgical arm 353.

In one embodiment, surgical instrument base 312 includes receiving elements or input disks 318 that releasably couple through an adapter to a rotatable driving element 334 that is mounted on the carriage 337 of robotic arm assembly 54. The rotatable driving elements 334 of the carriage 337 are generally coupled to actuators (not shown), such as electric motors or the like, to cause selective angular displacement of each in the carriage 337.

In one embodiment, when mounted to a surgical arm 54, end effectors 48 may have a plurality of degrees of freedom of movement relative to arm 54, in addition to actuation movement of the end effectors 48. The end effectors 48 of the surgical instruments 18 are used in performing a surgical operation such as cutting, shearing, grasping, gripping 66 (550), clamping, engaging, or contacting tissue adjacent a surgical site.

As illustrated in FIG. 21C, surgical instrument base 312 may be enclosed by a cover 372 to which one or more electrical connectors 374(a)-374(b) may be mounted. In one embodiment, adapter 328 includes one or more rotatable drivers 334 rotatably coupled to a floating plate 336. The rotatable drivers 334 are resiliently mounted to the floating plate 336 by resilient radial members which extend into a circumferential indentation about the rotatable drivers. The rotatable drivers 334 can move axially relative to floating plate 336 by deflection of these resilient structures.

In one embodiment, floating plate 336 has a limited range of movement relative to the surrounding adaptor structure normal to the major surfaces of the adaptor. Axial movement of the floating plate helps decouple the rotatable drivers 334 from a surgical instrument 18 when its release levers 316 are actuated.

In one embodiment, one or more rotatable drivers 334 of the adapter 328 may mechanically couple to a part of the surgical instruments 18. Each of the rotatable drivers 34 may include one or more openings 340 to receive protrusions or pins 322 of rotatable receiving members 318 of the surgical instruments 18. The openings 340 in the rotatable drivers 334 are configured to accurately align with the rotatable receiving elements 318 of surgical instruments 18.

In one embodiment, inner pins 322(a) and the outer pins 322(b) of the rotatable receiving elements 318 respectively align with the opening 340(a) and the opening 340(b) in each rotatable driver, Pins 322(a) and openings 340(a) are at differing distances from the axis of rotation than the pins 322(b) and openings 340(b) so as to ensure that rotatable drivers 334 and the rotatable receiving elements 318 are not aligned 180 degrees out of phase from their intended position. Additionally, each of the openings 340 in the rotatable drivers may be slightly radially elongated so as to fittingly receive the pins in the circumferential orientation. This allows the pins 322 to slide radially within the openings 340 and accommodate some axial misalignment between the surgical instrument and the adapter 328, while minimizing any angular misalignment and backlash between the rotatable drivers 334 and the rotatable receiving elements 318. Additionally, the interaction between pins 322 and openings 340 helps restrain the surgical instrument 18 in the engaged position with the adapter 328 until the release levers 316 along the sides of the housing 301 push on the floating plate 236 axially from the interface so as to release the surgical instrument 18.

When disposed in a first axial position (away from the surgical instrument side 330) the rotatable drivers are free to rotate without angular limitation. The one or more rotatable drivers 334 may rotate clockwise or counter-clockwise to further actuate the systems and instruments of the robotic surgical system 10. However, as the rotatable drivers move axially toward the surgical instrument side 330, tabs (extending radially from the rotatable drivers) may laterally engage detents on the floating plates so as to limit the angular rotation of the rotatable drivers about their axes. This limited rotation can be used to help engage the rotatable drivers the rotating members of the surgical instrument as the pins 322 may push the rotatable bodies into the limited rotation position until the pins are aligned with (and slide into) the openings 340 in the rotatable drivers.

In one embodiment, mounting of surgical instrument 18 to the adapter 328 can utilize an insertion of tip or distal end of the shaft or hollow tube of the surgical instrument 18 through a cannula (not shown) and sliding the interface base 312 into engagement with the adapter 328. A lip 332 on the surgical instrument side 330 of the adaptor 328 slidably receives the laterally extending portions of the interface base 312 of the robotic surgical instrument 18. A catch 344 of adapter 328 may latch onto the back end of the interface base 312 to hold the surgical instrument 18 in position. The protrusions or pins 322 extending from the one or more rotatable members 318 of the surgical instrument 18 couple into the holes 340a-340b (generally referred to as holes or openings 340) in the rotatable drivers 334 of the adapter 328.

In one embodiment, arrange of motion of the rotatable receiving elements 318 in the surgical instrument 18 may be limited. To complete the mechanical coupling between the rotatable drivers of the adapter and the rotatable receiving elements 318, the operator O at the surgeon console 12 may turn the rotatable drivers in one direction from center, turn the rotatable drivers in a second direction opposite the first, and then return the rotatable drivers to center. Further, to ensure that the pins 322 enter openings 340 of rotatable driver adapter 328, the adapter 328 and surgical instrument 18 mounted thereto may be moved together.

As discussed above, surgical instrument 18 can include one or more integrated circuits 326 to identify the type of surgical instrument 18 coupled to the robotic arm, in order to properly controlled by surgeon consol 12. Robotic surgical system 10 can determine whether or not the surgical instrument 18 is compatible or not, prior to its use.

As a non-limiting example, robotic surgical system 10 verifies that the surgical instrument 18 is of the type which may be used with the robotic surgical system 10. The one or more integrated circuits 326 may signal to the computer 151 in the surgeon consol 12 data regarding compatibility and instrument-type to determine compatibility as well as control information. One of the integrated circuits 326 may include a non-volatile memory to store and read out data regarding robotic surgical system compatibility, the instrument-type and the control information. In an exemplary embodiment, the data read from the memory includes a character string indicating surgical instrument compatibility with the robotic surgical system 10. Additionally, the data from the surgical instrument memory will often include an instrument-type to signal to the surgeon control consol how it is to be controlled. In some cases, the data will also include surgical instrument calibration information. The data may be provided in response to a request signal from the computer 151.

In one embodiment, instrument-type data indicates the kind of surgical instrument 18 has been attached in a surgical instrument change operation. As a non-limiting example, instrument-type data can include information on wrist axis geometries, surgical instrument strengths, gripper 550 force, the range of motion of each joint, singularities in the joint motion space, the maximum force to be applied via the rotatable receiving elements, the surgical instrument trans- mission system characteristics including information regard- ing the coupling of rotatable receiving elements to actuation or articulation of a system within the robotic surgical instru- ment, and the like.

In one embodiment, instrument-type data is not stored in integrated circuits 326 but is stored in memory or a hard drive of the computer 151. In one embodiment, an identifier is stored in integrated circuits 326 to signal the computer 151 to read the relevant portions of data in a look up table store in the memory or the hard drive of computer 151. The instrument-type data in the look-up table may be loaded into a memory of computer 151 by the manufacturer of the robotic surgical system 10. As a non-limiting example, look-up table can be stored in a flash memory, EEPROM, or other type of non-volatile memory. As a new instrument- type is provided, the manufacturer can revise the look-up table to accommodate the new instrument-specific informa- tion. It should be recognized that the use of surgical instru- ments 18, which are not compatible with the robotic surgery system 10, for example, which do not have the appropriate instrument-type data in an information table, could result in inadequate robotic control over the surgical instrument 18 by the computer 151 and the operator O.

In one embodiment, surgical instrument specific informa- tion is stored in integrated circuits 326, such as for recon- figuring the programming of computer 151 to control sur- gical instrument 18. In one embodiment, this includes calibration information, such an offset, to correct a misalign- ment in the surgical instrument 18. The calibration infor- mation can be factored into the overall control of the surgical instrument 18. The storing of such calibration information can be used to overcome minor mechanical inconsistencies between surgical instruments 18 of a single type.

As a non-limiting example, information about a surgical instrument 18 life span, surgical instrument life, and cumu- lative surgical instrument 18 use can be stored on the surgical instrument memory and used by computer 151 to determine if the surgical instrument is still safe for use, In one embodiment, surgeon consol 12 generates the control signals to control surgical instruments 18 in a surgical site and medical equipment that supports surgical instruments 18, As a non-limiting example, surgeon consol 12 can include a binocular or stereo viewer, an arm-rest, a microphone, a pair of master controllers for end effector 48 input control, wrist input control, and arm input control within a workspace, one or more speakers, foot pedals 68, viewing sensor, and the like.

Figure 22:
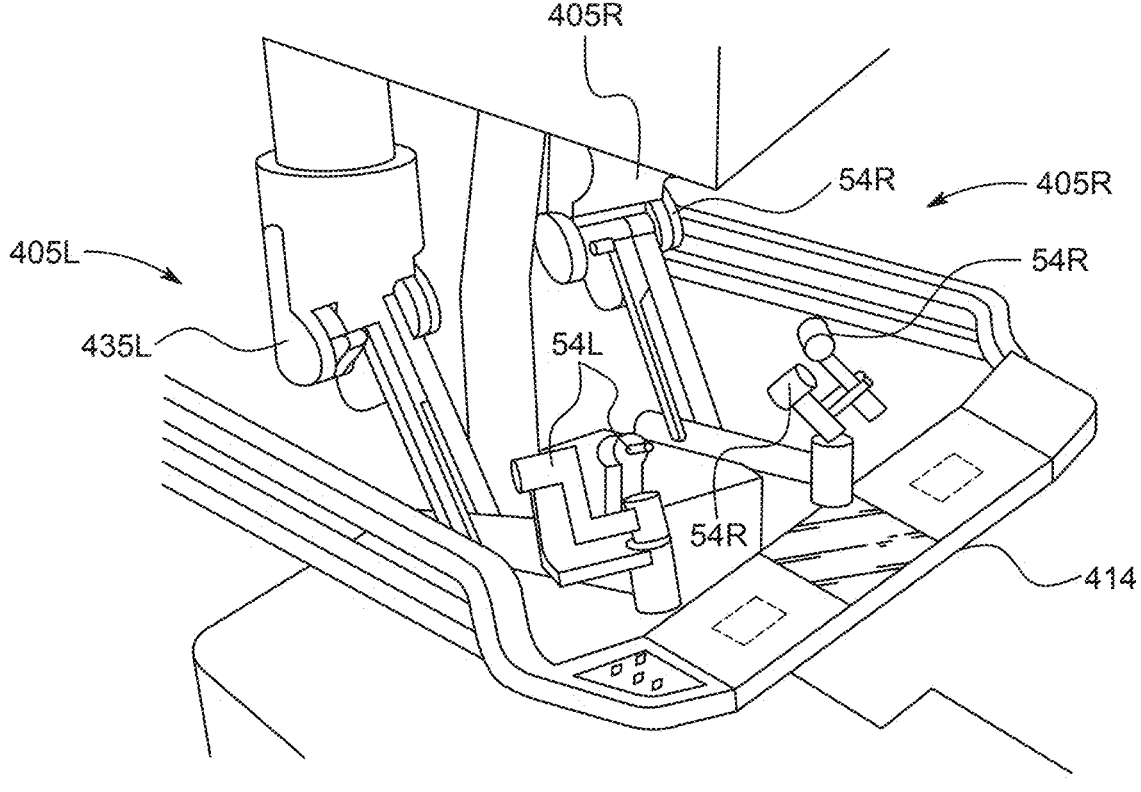
FIG. 22 illustrates one embodiment of a workspace in a surgeon's console showing a left master controller and a right master controller of the present invention.
Figure 23:
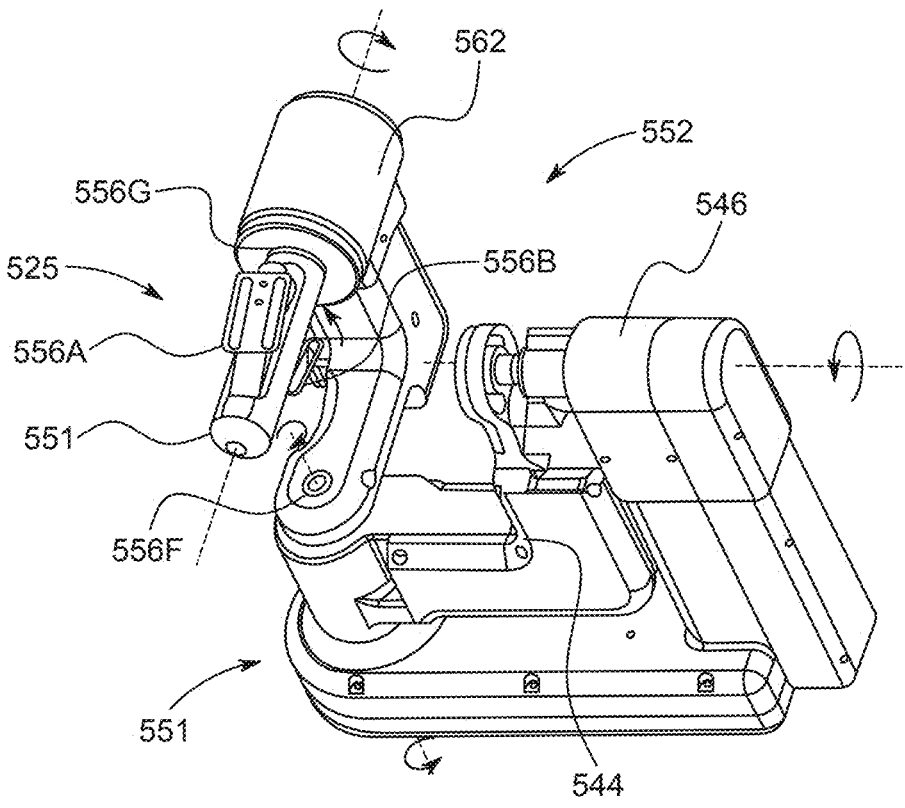
FIG. 23 illustrates one embodiment of a gimbaled control input wrist pivotally supporting a master grip control handle for a robotic surgical master control console of the present invention.
Figure 24:
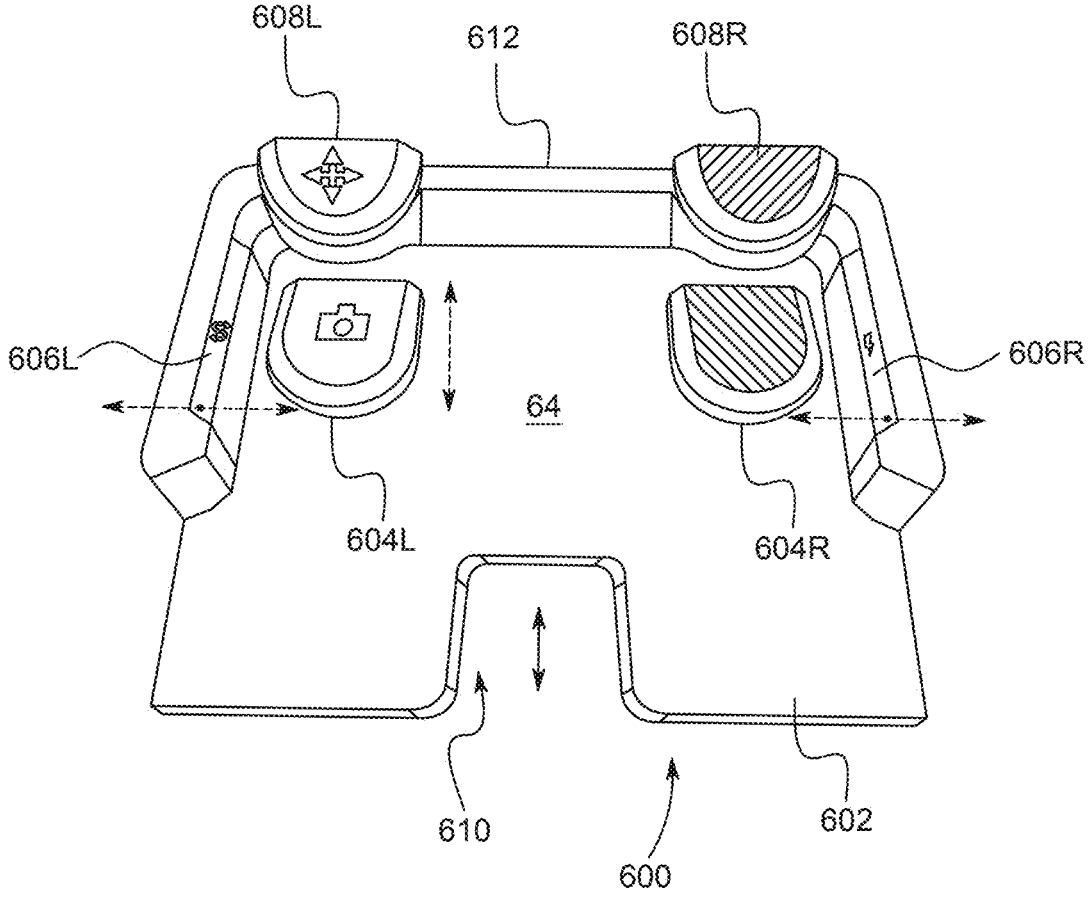
FIG. 24 illustrates one embodiment of an integrated pedal system of the surgeon's control console of the present invention.

As a non-limiting example, illustrated in FIG. 22, master controllers 405(L), and 405(R), at surgeon consol 12 include a control input grip or master gripper 525 and a control input wrist 414 coupled together to control input arms 54(L), and 54(R). In one embodiment, control input wrist 414 is a gimbaled device that pivotally supports a master gripper 525 of surgeon consol 12 to generate control signals that are used to control patient consol 16 and surgical instruments 18, In one embodiment, control input wrists 414 for the left and right master controllers are supported by a pair of control input arms 54, Control input wrist 414 includes first, second, and third gimbal members. The surgeon console 12 has a left master controller 405(L) and a right master controller 405 (R). The left master controller 405(L) includes a left control input arm 54(L), a left control input wrist 54(L) and a left control input grip 54(L). The right master controller 405R, includes a right control input arm 54(R), a right control input wrist 54(R) and a right control input grip, FIG. 23 is a perspective view of a control input wrist 552 representative of the left control input wrist and the right control input wrist is illustrated. The master controllers at the surgeon's console include a control input grip or master gripper 525 and a control input wrist 552 coupled together to a control arm (see control input arms 935(L), in FIG. 22). The control input wrist 552 is a gimbaled device that pivotally supports the master gripper 525 of the master control console 150 to generate control signals that are used to control patient consol 16 surgical instruments 18, includ- ing electrosurgical robotic instruments 18(*a*) and 18(*b*). A pair of control input wrists 552 for the left and right master controllers are supported by a pair of control input arms in the work site 516 of the master control console. The control input wrist 552 includes first, second, and third gimbal members 562, 564, and 566. The third gimbal member 566 is rotationally coupled to a control input arm (not shown) of the master control console 150, 150(*a*).

Master gripper 525 includes a tubular support structure 551, a first gripper 550(*a*), and a second gripper 550(*b*). The first and second grippers 550(*a*) and 550(*b*) are supported at one end by the structure 551. The master gripper 525 can be rotated. Grippers 550(*a*), 550(*b*) can be squeezed or pinched together about the tubular structure 551.

Master gripper 525 is rotatably supported by the first gimbal member 562 by means of a rotational joint 556(*g*). The first gimbal member 562 is in turn, rotatably supported by the second gimbal member 564 by means of the rotational joint 556(*f*). Similarly, the second gimbal member 564 is rotatably supported by the third gimbal member 566 using a rotational joint 556 *d*. In this manner, the control wrist allows the master gripper 525 to be moved and oriented in the workspace 516 using three degrees of freedom. The movements in the gimbals of the control wrist 552 to reorient the master gripper 525 in space can be translated into control signals to control patient consol 16 and surgical instruments 18.

Movements in grippers 550(*a*), and 550(*b*) of master gripper 525 can also be translated into control signals to control patient consol 16 and surgical instruments 18. In particular, the squeezing motion of grippers 550(*a*), and 550(*b*) over their freedom of movement, and be used to control the end effectors 48 of the robotic surgical instru- ments 18.

To sense the movements in master gripper 525 and generate controls signals, sensors can be mounted in the handle of master gripper 525 as well as the gimbal member 562 of the control input wrist 552. Exemplary sensors may be a Hall effect transducer, a potentiometer, an encoder, or the like.

As a non-limiting example, robotic surgical system 10 includes one or more of; one or more cameras 46 and multiple end effectors 48, surgical control software 38; surgeon controls; image recognition database 34; procedure database 36; a medical image database; and the like. As a non-limiting example, procedure database 36 can include medical records data, images (e.g., pre- and post-surgical images), physician input, sensor data, and the like. In one embodiment, image recognition database 34 is populated by images taken by the cameras 46 that defined by surgeons and can be updated with each use of robotic surgical system 10 for greater accuracy. In one embodiment, surgeon controls are used for manual manipulation of the surgical robot. Surgical control software 38 may include an incision marking module, and AI system 42 include a progression module. In one embodiment, the # surgical control software 38 begins when initiated by the surgeon.

In one embodiment, robotic surgical system 10 initiates an incision marking module which ensure the patient is properly positioned and the incision site is marked. When the incision marking module is complete. AI system 42 may be initiated. In one embodiment, the incision marking module may be designed to cover the steps in the spinal surgery between when the patient is placed on the table and when AI system 42 system makes the first incision. In one embodiment, the module begins when it receives a prompt from the surgical control software 38. In one embodiment, the incision location, in this example just above the L4 vertebrae, is identified from the pre-operative plan. In one embodiment, system 10 captures an image of the patient to determine if they are properly positioned on the operating table. If they are not, the surgeon or assistant are prompted for the necessary adjustment and a new image may be captured. This loop continues until robotic surgical system 10 is satisfied that the patient is properly positioned.

In one embodiment, AI system 42 system uses the camera 46 to take an image of the point of interest and the progression module may compare that image to the image recognition database 34 to determine if the tissue present is the desired tissue type that will allow the surgical robot 20 to proceed. In one embodiment, the progress through the tissue type is displayed based on the number of layers of the current tissue removed as compared to the average number of layers removed in other patients who had the same procedure and had a similar anatomical volume of their surgical point of interest.

As a non-limiting example, imaging system coupled to the image software 38 is in the same location. It can be co-located on the same robot arm as the bone removal end effector 48 or on another mount that allows it a view of the point of interest. In one embodiment, the imaging system 10 may take an image of the point of interest, and the progression module will run. When the tissue type is confirmed, the bone removal end effector 48 removes a small layer of tissue. In one embodiment, the imaging system repeats the process of tissue type confirmation, followed by the end effector 48 removing another layer of tissue. This loop continues until the imaging system identifies a different tissue type.

In one embodiment, the imaging system and progression module are initially trained using a neural network/machine learning. Using machine learning systems which construct algorithms that can learn from and then make predictions on the image data, which is a common task in machine learning. Such algorithms work by making image data-driven predictions through building a mathematical model from image input data. In one embodiment, the image data is used to build the final model which usually comes from multiple datasets (in this case, dataset of previous operations visual data with metadata associated with the images from doctor articulated tissue types). In particular, three data sets (images, metadata of tissue type and metadata of bone portions unfolding in the images over time) may be used in different stages of the creation of the model. A third party, associate or surgeon can input or change metadata. For example, the metadata can include surgeon defined metadata. In some embodiments, the metadata can be defined by AI system 42. In some embodiments, the metadata can include both surgeon and assistants, prior surgeons and assistants, third parties, and AI defined data.

In one embodiment, the model is initially fit on a training dataset, which is a set of examples used to fit the parameters (e.g., weights of connections between "neurons" in artificial neural networks) of the model. In one embodiment, the model (e.g., a neural net or a naive Bayes classifier) may be trained on the training dataset using a supervised learning method (e.g., gradient descent or stochastic gradient descent). In practice, the training dataset often includes pairs of generated "input vectors" with the associated corresponding "answer vector" (commonly denoted as the target). In one embodiment, the current model is run with the training dataset and produces a result, which is then compared with the target, for each input vector in the training dataset. Based on the result of the comparison and the specific learning algorithm being used, the parameters of the model are adjusted. In one embodiment, the model fitting can include both variable selection and parameter estimation.

One or more models predict the responses for the observations in a second dataset called the validation dataset. In one embodiment, the validation dataset provides an unbiased evaluation of a model fit on the training dataset while tuning the model's parameters. Validation datasets can be used for regularization by early stopping: stop training when the error on the validation dataset increases, as this may be a sign of overfitting to the training dataset. This simple procedure is complicated in practice by the fact that the validation dataset's error may fluctuate during training, which would require added ad-hoc rules for deciding when overfitting has truly begun. Finally, the test dataset is a dataset used to provide an unbiased evaluation of a final model fit on the training data.

Once this trained dataset is built, the # s may be fed into robotic surgical system 10 and as tissues are identified, the tissue types are annotated virtually over the real time images, with a percent probability of identification. This allows the surgeon to have an AI image recognition assistant.

In one embodiment, robotic surgical system 10 includes a failsafe that allows the surgeon on hand to stop the process. Stopping the process may include a teaching step in which the surgeon defines the tissue type visible, # to improve the functionality of the image recognition software of image recognition database 34.

In one embodiment, the failsafe robotic surgical system 10 provides historical data of many operations that stores the amount of time (video) and the Virtual identified images on the tissue. In one embodiment, the tissues identified may be in a time sequence as the operation proceeds. In a real-time operation, the sequence of image-recognized tissue (and the timing of getting to and through these recognized tissues) is compared to the historical database. If the real-time recognized tissues are correlated with the same sequence of tissues in the historical database, robotic surgical system 10 proceeds. However, if a recognized tissue does not appear in the sequence history, or if the recognized tissue appears earlier than expected, robotic surgical system 10 is alerted, which causes an alarm, with a virtual message over the non-normal images.

In one embodiment, there could be other fail-safe triggers including but not limited to: the length of time between recognized tissues that are normal; the probability of the recognition trending down; and the image quality starting to degrade, etc. In this way the failsafe system could have multiple processes running simultaneously.

When AI system 42 system completes a step in its entirety, it may return to the surgical control software 38, which determines based on the pre-operative plan, if the procedure is complete. If the procedure is complete, the program ends.

If the program is not complete, the pre-operative plan is consulted to determine if the next surgical step requires a different end effector 48. End effectors 48 can include surgical instruments 18 such as retractor tubes and surgical hardware, in addition to the incision markers, bone removal tools, skin/muscle fascia incision tools, etc. If a new end effector 48 is needed, the surgeon or support staff makes the hardware adjustment before robotic surgical system 10 proceeds to the next step in the pre-operative plan. After the needed end effector 48/tool is put into place, or if the same end effector 48/tool from the previous step is appropriate, robotic surgical system 10 may go back to AI system 42 system until the next surgical step is completed. This process continues to loop until the procedure is complete. To perform multiple procedures on a patient, the end effector 48 can be replaced to begin another procedure.

In one embodiment, robotic surgical system 10 may then initiate the incision marking module which will ensure the patient is properly positioned and the incision site is marked. When the incision marking module is complete, AI system 42 system is initiated.

In one embodiment, AI system 42 system works through each step in the surgical process, # When AI system 42 system completes a step in its entirety, it returns to the surgical control software 38, which determines based on the pre-operative plan, if the procedure is complete. If the procedure is complete, the program ends.

If the program is not complete, the pre-operative plan is consulted to determine if the next surgical step requires a different end effector 48. End effectors 48 in this scenario also include surgical instruments 10 such as retractor tubes and surgical hardware, in addition to the incision markers, bone removal tools, incision tools (e.g., skin/muscle fascia incision tools), etc. If a new end effector 48 is needed, the surgeon or support staff can make the hardware adjustment before robotic surgical system 10 proceeds to the next step in the pre-operative plan. After the needed end effector 48/tool is put into place, or if the same end effector 48/tool from the previous step is appropriate, robotic surgical system 10 may go back to the AI system 42 system until the next surgical step is completed. This process continues to loop until the procedure is complete.

In one embodiment, an incision marking module is provided that is part of the surgical control software 51, according to an embodiment. In one embodiment, the incision marking module is designed to cover the steps in the spinal surgery between when the patient is placed on the table and when AI system 42 system the first incision.

In one embodiment, the module begins when it receives a prompt from the surgical control software. In one embodiment, the incision location, in this example just above the L4 vertebrae, is identified from the pre-operative plan.

In one embodiment, the module may then capture an image of the patient to determine if they are properly positioned on the operating table. If they are not, the surgeon or support staff are prompted for the necessary adjustment and a new image is captured. This loop continues until robotic surgical system 10 is satisfied that the patient is properly positioned.

In one embodiment, the end effector 48 is navigated to the point of interest.

In one embodiment, then the progression module is run, which may update the progress on the robotic surgery system 10 display 24 and return if the tissue at the point of interest is the desired tissue type. So, if the tissue type identified is not bone, robotic surgical system 10 stops, alerts the surgeon and polls for their input.

In one embodiment, the surgeon will need to define the tissue type currently at the point of interest. If the surgeon defines the current tissue type as the desired tissue type, this updates the image recognition database 34 and robotic surgical system 10 returns to the progression module with the updated image recognition definitions. If the surgeon defines the tissue as any other type of tissue than the desired tissue type, the image definition is added to the database 34 and the number of layers removed of the desired tissue type for the current patient is recorded in the 36.

Figure 5:
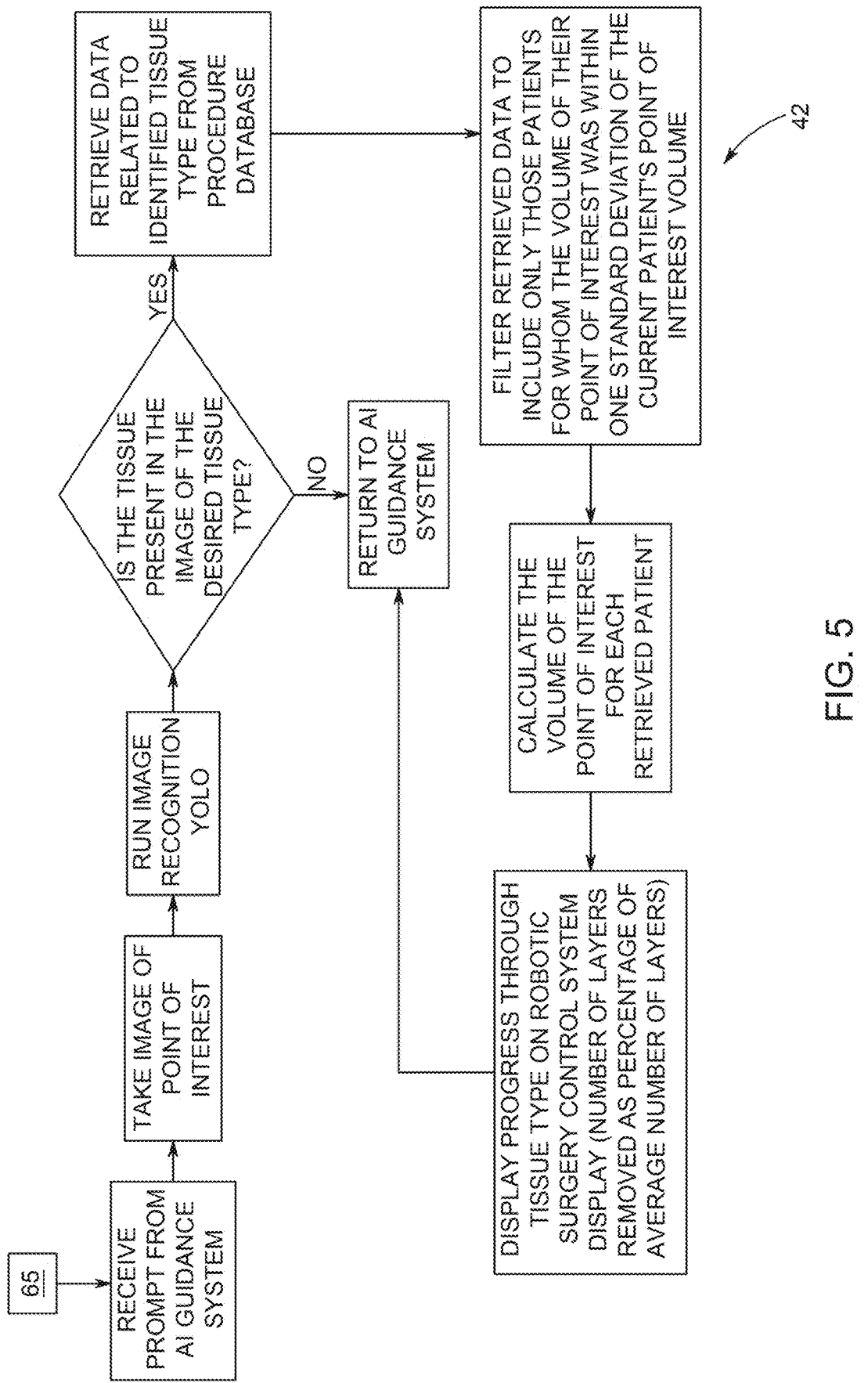
FIG. 5 illustrates one embodiment of a progression module of the present invention.

FIG. 5 represents the progression module, according to an embodiment. In one embodiment, the progression module is triggered by AI system 42 system when the imaging system and the end effector 48 are at the point of interest on the current patient, An image of the point of interest is taken and an image recognition system associated with image recognition 34 is used to identify the tissue type present in the image taken of the point of interest on the current patient. In one embodiment, the image recognition system utilizes the database 34 to identify the tissue type and to store the definitions of tissue types found in images as they are defined by surgeons using the robotic surgical system 10.

In one embodiment, the real-time images may be fed into a "trained neutral network image system" as described above, which uses this historical data to inform a YOLO ("you only look once") system. # In one embodiment, the real-time images may be used to identify the tissue type present in the image taken of the point of interest on the current patient. Unlike simply identifying the tissues types, which we have discussed above by adding a Virtual tissue tag on the images, this YOLO system goes further, in that it can detect distances and positions between the boundary boxes. In this way, tissue type will not only be defined virtually over the real-time images, # but virtual distances are overlaid and can be highlighted when they are outside norms (again these distances of boundary boxes are pre-trained). In one embodiment, the image recognition system utilizes the historical image database and YOLO to identify the tissue type and their positions to provide real-time augmentation data to the surgeons using the robotic surgical system.

If the tissue type identified is not the desired tissue type for the surgical robot 20 to proceed with tissue removal, the module ends and returns to AI system 42 system. If the tissue type identified is the desired tissue type to proceed with tissue removal, data related to the identified tissue type is retrieved from the 36

In one embodiment, pre-operative images are used. A surgeon, assistant or third party can input information for performing procedures. In one embodiment, the information can include, without limitation, targeted tissue, non-targeted tissue, critical tissue (e.g., tissue to be protected or avoided), access paths, cutting/drilling paths, instrument orientations (e.g., delivery instruments, surgical instruments 18, and the like), working spaces, safety barriers, hold spots, or the like.

In one embodiment, the information can be used to determine or modify a surgical plan and can be inputted via a touch screen, keyboard, or the like. A method of using an image in which a sketch on the image indicates parts of the anatomical structure to be removed. This is a freehand adjustment by the surgeon to the preoperative plan, layered on top of medical imaging (MRI, CT, etc.). This adjustment to the surgical plan is transmitted to surgical robot 20 and it only removes the desired area, the surgeon supervises the surgical robot 20 during the procedure to take over/resume the operation if necessary, In one embodiment, pre-operative image uses an interactive user interface. In one embodiment, the image received from the surgical robot 20 is displayed on a touch screen/ user interface inside the operating room and the surgeon sketches on the image which of the corresponding area of tissue is supposed to be removed. Other important areas can be identified (such as nerves) to warn the surgical robot 20 to stay away from sensitive areas. This is applicable to all steps past this one in this process but is documented here as this is the first step in which the surgeon would mark out areas during the procedure as opposed to during pre-operative planning.

In one embodiment, incision localization/markings are made as pre-operative images on an actual image using interactive user interface, robotic surgical system 10 can deploy graphical surgical instruments 18, similar to power point, that allows the surgeon to draw shapes of different colors over the image. The shapes can be auto filled with the suggested colors and meta-tags (e.g., distance depth, speed of drill, amount of dither, etc.). For instance, robotic surgical system 10 could allow the surgeon in drawing mode to define the draw pen or mouse to be defined as "red, 1 mm deep, 100 rpm, +/−5 rpm", where red would correspond to drill, 1 mm deep at 100+/−5 rpm. In another area for instance, the surgeon could have defined a yellow +0.5 mm which is a region that the surgical robot 20 is barred from running. One could image many other user interface controls, such as (1) cutting or drilling paths, (2) degrees of safety barriers along the cutting, (3) hold spots, (4) jump to another spots, etc. The surgeon would stand by during the procedure and can turn off the machine at any time. The drill also has built-in safeguards. For example, it can detect if it is too close to a nerve (e.g., a facial nerve) and will automatically shut off, As a non-limiting example, incision localization/marking" are made using interactive user interface to resolve latency issues.

As a non-limiting example, incision localization/marking are made such as multiple imaging systems for problem space identification in spinal surgery. A method that combines multiple imaging systems to identify a problem space in a patient's spine. An algorithm is applied to the images to calculate the best incision location based on where the problem space is located. This algorithm accounts for the surgical procedure being used when identifying the incision site.

As a non-limiting example, methods are provided that allows surgeons to annotate where a surgical robot 20 should move or adjust to in order to place the guide wire while locating an incision site. The surgical robot 20 can learn where it is commanded to move and store the information in a database. The surgical robot 20 can access this database to use for references during future procedures. This increases efficiency, accuracy, and repeatability for locating incision sites.

As a nonlimiting example, robotic surgical system 10 allow the surgeon to pick the most applicable shape to use for different procedures or at a specific point in a procedure. The shapes can also be produced through the combining of different guide wires. Guidewire shape would be determined by AI using correlations between patient attributes, procedure type, wire shape, and postoperative outcomes.

As a non-limiting example, robotic surgical system 10 projects an imaging system output onto the patient to show where different tissue types are located underneath the skin. The projection would also include a projection of the guide wire to help the surgeon visualize the best point of incision. This increases the accuracy of the incision point. This can be done with high-speed projectors, or with an augmented reality 20 for the surgeon. Alternate embodiments can include virtual reality headsets for incision placement.

In one embodiment, robotic surgical system 10 uses surgical control software 38 that utilizes AI to determine the optimal trajectory and incision placement for any type of spinal surgery (e.g., spinal fusion, decompression procedures, screw placement, cage insertion, etc.). This method uses information about the surgery to decide the trajectory and incision site, such as screw size, the angle the screw will be inserted at, and other information. A virtual line is then drawn out from where the drill will be placed during surgery.

In one embodiment, robotic surgical system 10 marks the incision site for a spinal surgical procedure that includes information that cites where the screw needs to be placed, which was determined from a mathematical calculation. This information includes an image, which shows the projected incision site from an algorithm. This makes the incision site more accurate and the process for finding this site more repeatable, regardless of the patient's anatomy.

In one embodiment, robotic surgical system algorithms are to determine where the best incision site is on the patient based on the procedure and where the surgeon's point of interest is. This process will make the incision site more accurate and the process for finding this site more repeatable, regardless of the patient's anatomy. The amount of soft tissue damage that occurs in surgery will also decrease because the algorithm accounts for minimizing tissue damage.

In one embodiment, robotic surgical system 10 uses AI to map where an imaging port should be located on the patient to map the patient's body most effectively. This robotic surgical system considers where the surgeon is planning to make the initial incision on the patient's body to help determine where the imaging port should be located, robotic surgical system 10 re-evaluates where the imaging port should be placed during different steps throughout the procedure.

In one embodiment, robotic surgical system 10 virtualization is provided with a third person perspective of Visualization Device progress through augmented reality or virtual reality means. The third person perspective of the effort head would be mapped to other medical images used during surgery. This allows the camera 46 point of view to be virtualized, eliminating the need to have a second entry port. # This method comprising of a camera 46 that is placed on the end effector 48 itself, which provides a real-time image; and a tracking system shows the position of the Visualization Device in the patient's body from the outside in real-time. All this real-time data is overlaid on the pre-constructed model, which provides the surgeon with information that allows him or her to dynamically changed the perspective.

In one embodiment, robotic surgical system 10 computer analysis of pre-operative MRI images using AI to identify the patient's abnormality. This information can be used to confirm the position of a robot. This would eliminate wrong level surgery. This is augmented with a method that quantifies the confirmation level of the robot's position, acting as a "confirmation meter." This may include using many sources, such as multiple images at different levels, using pre-operative images, inter-operative images, computer-assisted navigation, and other means, to calculate the accuracy of the robot's position. The higher the position accuracy, the higher the confirmation meter score, In one embodiment, robotic surgical system 10 Visualization Devices constantly interact with the anterior-posterior (AP) view, allowing the surgeon to be constantly looking at Visualization Device 58. This system is expanded to cover the entirety of the procedure by using the same functionality that allows Visualization Device 58 to function as a guide wire to locate Visualization Device 58 inside of the patient as an additional reference point for the surgical navigation program. The configuration of Visualization Device 58 can be selected based on the instrument to be delivered over it, In one embodiment, robotic surgical system 10 used AI in which a surgeon identifies the different types of tissues (nerve, ligament, bone, etc.) and how to use different end effectors 48 for each type of tissue. Rules can be added to ensure that specific end effectors 48 can only be used on specific types of tissue (i.e. a drill is only used on bone, or a nerve is only touched with a probe or not allowed to be touched at all). This is applicable to all steps in the process but documented here as multiple tissue types are involved in this specific step.

In one embodiment, robotic surgical system 10 normalizes lighting for probing or imaging system for AI image recognition. Once robotic surgical system 10 identifies specific types of tissue, a normalized lighting process allows robotic surgical system 10 to see the same or similar colors to easily identify previously learned tissues.

In one embodiment, robotic surgical system 10 uses information such as color, texture, and force to what equipment is being utilized in a robotic surgery, robotic surgical system 10 can understand when enough bone has been worked through to recognize that the surgical robot 20 should stop using the drill. This is like the concept described in the disclosure, but rather than relying solely on image, robotic surgical system incorporates contact sensors, tissue type sensors (e.g., impedance sensors, optical sensors, etc.), pressure sensors, force sensors, to improve the accuracy of the tissue identification system, robotic surgical system 10 can analyze signals from the sensors to determine, for example, the force required to continue through the tissue, tissue type, texture the tissue, or the like, robotic surgical system 10 can perform procedures based, at least in part, on identifying the tissue type and its location.

As a non-limiting example, as a drill or knife is robotically controlled, the drill or knife provides sensitive force transducers. These force transducers produce a real time X,Y,Z force set of data. The data is collected in many successful operations. $The real-time images not only have all the previous metatags discussed, but also have the real time X,Y,Z force data, robotic surgical system can be trained to show the delta force change going from one tissue type to another. As above, the change in force in X,Y,Z can be used to compare to real-time operations. If the tissues are identified correctly and within range, and the forces and changes of force are within range, the images are annotated with virtual information showing that tissues and forces and changes in force are in order. If, however, the forces or changes of force appear out of normal range, alarms would sound, and automated robotic stops would be done to investigate the out of norm situation. With this robotic surgical system, the surgeon can create a "sensitivity" of force change at various parts of the operations, so robotic surgical system may alarm when it approaches a nerve as the force and change of force alarm is set at a more sensitive level than another part of the operation, As a non-limiting example, robotic surgical system 10 uses biomarkers to communicate with surgical robot 20 where it is during surgery. In one embodiment, robotic surgical system can recognize what type of tissue the surgical robot 20 is touching and then be able to mark the tissue accordingly. Using this robotic surgical system, a surgical robot 20 will be able to recognize what type of tissues it is near and use that information to determine where it is in the patient.

In one embodiment, robotic surgical system 10 uses AR or VR to display 20 where a surgical instrument 18 is being inserted into the patient. The precise display of where the device should be located can be seen by the surgeon during an operation, so the device is accurately placed. The surgical device placement recommendations can be in response to information from AI examination of surgical procedure data, patient data, and postoperative outcomes, to identify correlations between surgical device placement and adverse events, or device placement and positive post-operative outcomes.

In one embodiment, robotic surgical system 10 includes retractor tube that is a part of a surgical robot that vibrates microscopically at a high speed. This would create a wavefront that would allow the tube to insert into the patient's body with greater ease. This concept would be augmented using the AI in conjunction with the image recognition system to identify tissue types and adjust the vibration frequency/amplitude based upon correlations identified by the AI between vibration frequencies/amplitudes and positive outcomes/adverse events.

As non-limiting examples, robotic surgical system 10 provides: changing a temperature of the retractor tube (i.e. heating it up or cooling it down) instead of vibration; a hand-held ball-tip probe with sensors located in the robotic arm 54/surgical instrument 18 to determine the position of the probes location ### for creating a SD map of a patient selected site; image recognition to show a "point of view" and can use AI pictures compared to a historical database of similar surgeries/operations; captures data from a camera 46 in which the data is uploaded into a historical database to refine and improve robotic surgical system 10 for future surgeries; collects data from pressure sensors on a surgical instrument 18 and data from touch sensors, along with AI to learn; and add to databases; mapping surgical paths for procedures that minimize damage through AI mapping; and the like.

Robotic surgical system 10 can include one or more joints, links, grippers 550, motors, and effector 48 interfaces, or the like. The configuration and functionality of robotic surgical system 10 can be selected based on the procedures to be performed.

In one embodiment, effectors 48 are installed in the robotic system The end effectors 48 can include one or more of: robotic grippers 550; cutting instruments (e.g., cutters, scalpels, or the like), drills; cannulas; reamers; rongeurs; scissors; clamps or the like.

As a non-limiting example, surgeries, processes, and the like can be implemented as computer-readable instructions stored on a computer-readable medium Each of the surgical instruments 18 are manipulated by a slaved robotic manipulator and remotely controlled by control signals received from a master control console. As a non-limiting example, surgeon performs surgical procedure on patient P by manipulating input devices at a surgeon console 12. A computer 151 can be used to direct movement of surgical instruments 18, effecting movement of surgical instruments 18 using patient consol 16. Arms 54 can be supported by linkages, with a central arm supporting an endoscopic camera 46.

In one embodiment, arms 54 include a positioning portion and a driven portion. The positioning portion of the patient consol 16 remain in a fixed configuration during surgery while manipulating tissue. The driven portion of patient consol 16 is actively articulated under the direction of surgeon O generating control signals at the surgeon's consol 12 during surgery. The actively driven portion of the arms 54 can be referred to as an actuating portion. The positioning portion of the arms 54 that are in a fixed configuration during surgery can be referred to as positioning linkage and/or set-up joint.

As a non-limiting example, a variety of different surgical instruments 18 and equipment can be used, including but not limited to electrosurgical, laser, and the like, Surgical instruments 18 can be used to supply vacuum, gasses, liquids, energy (e.g., electrical, laser, ultrasound), mechanical torques, mechanical push/pull forces, data signals, control signals, etc. to support functions of other types of surgical instruments 18 (e.g., ultrasound, lasers, staplers). As a non-limiting example, a surgical instrument 18 may combine the function of laser cutting and ultrasound together that is supported by a remote controlled laser generator and a remote controlled ultrasound generator, both of which can be remotely controlled from surgeon console 12.

In one embodiment, robotic surgical system 10 uses AR or VR to display 20 where a surgical instrument 18 is being inserted into the patient. The precise display of where the device should be located can be seen by the surgeon during an operation, so the device is accurately placed. The surgical device placement recommendations can be in response to information from AI examination of surgical procedure data, patient data, and postoperative outcomes, to identify correlations between surgical device placement and adverse events, or device placement and positive post-operative outcomes.

In one embodiment, robotic surgical system 10 uses one or more AI algorithms of AI system 42. As recited above, as non-limiting examples, AI system 42 can use a variety of different algorithms including but not limited to: supervised learning; classification and regression; decision tree; random forest; support vector machines, Naïve Bayes, linear regression; logistic regression; enhanced imaging; image recognition; treatment planning; risk assessment; robot-assisted navigation; path planning; collision avoidance; autonomous robotics; steady hand assistance; intraoperative decision support; real-time feedback; alert and warning, postoperative monitoring and analysis; prediction; patient outcomes; continuous learning and improvement; data analysis; and the like.

The large amount of data obtained pre-existing data, prior surgeries, current patient anatomy and information, can analyzed by AI algorithms to improve a patient's surgical results, post-operative recovery, pre-operative conditions, pre-operation analysis, and the like, can lead to more opportunities for proactive, modernized, and personalized patient surgeries, recoveries, pre-operation status, and the like. The combination of this information in combination with AI algorithms allows comprehensive information for surgeries.

Machine learning (ML) techniques can combine medical datasets from millions of patients, such as diagnostic profiles, imaging records, and wearable information, to analyze the internal structure of the ocean of medical big data, identify patterns of disease conditions, and overcome the general limitations on access to local datasets. Furthermore, the next-generation healthcare system supported by big data shifts from a centralized hospital-based mode to a parallel mode of monitoring at home, screening and detection at point-of-care testing (POCT), and monitoring during hospitalization, meanwhile, achieves doctor-patient interaction and data transferring via the cloud to ease robotic surgery system 10 resources and facilitate personalized surgery.

Figure 25A:
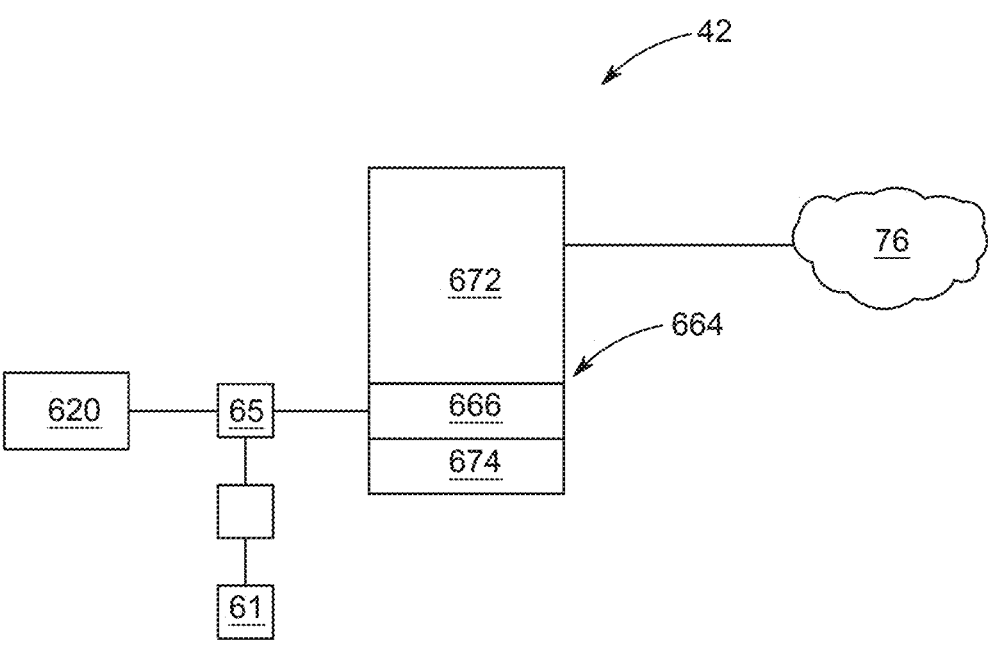
FIGS. 25A and 25B illustrate one embodiment of an AI system used with the present invention.
Figure 25B:
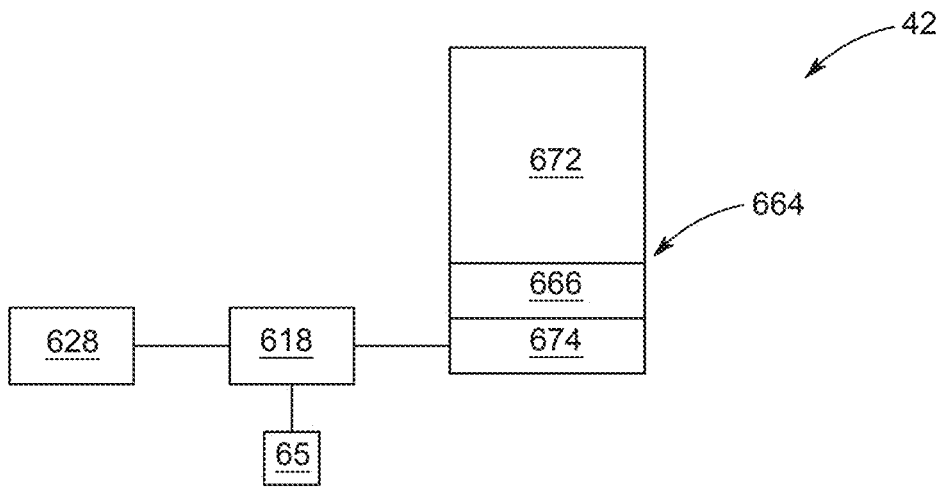
Figure 25C:
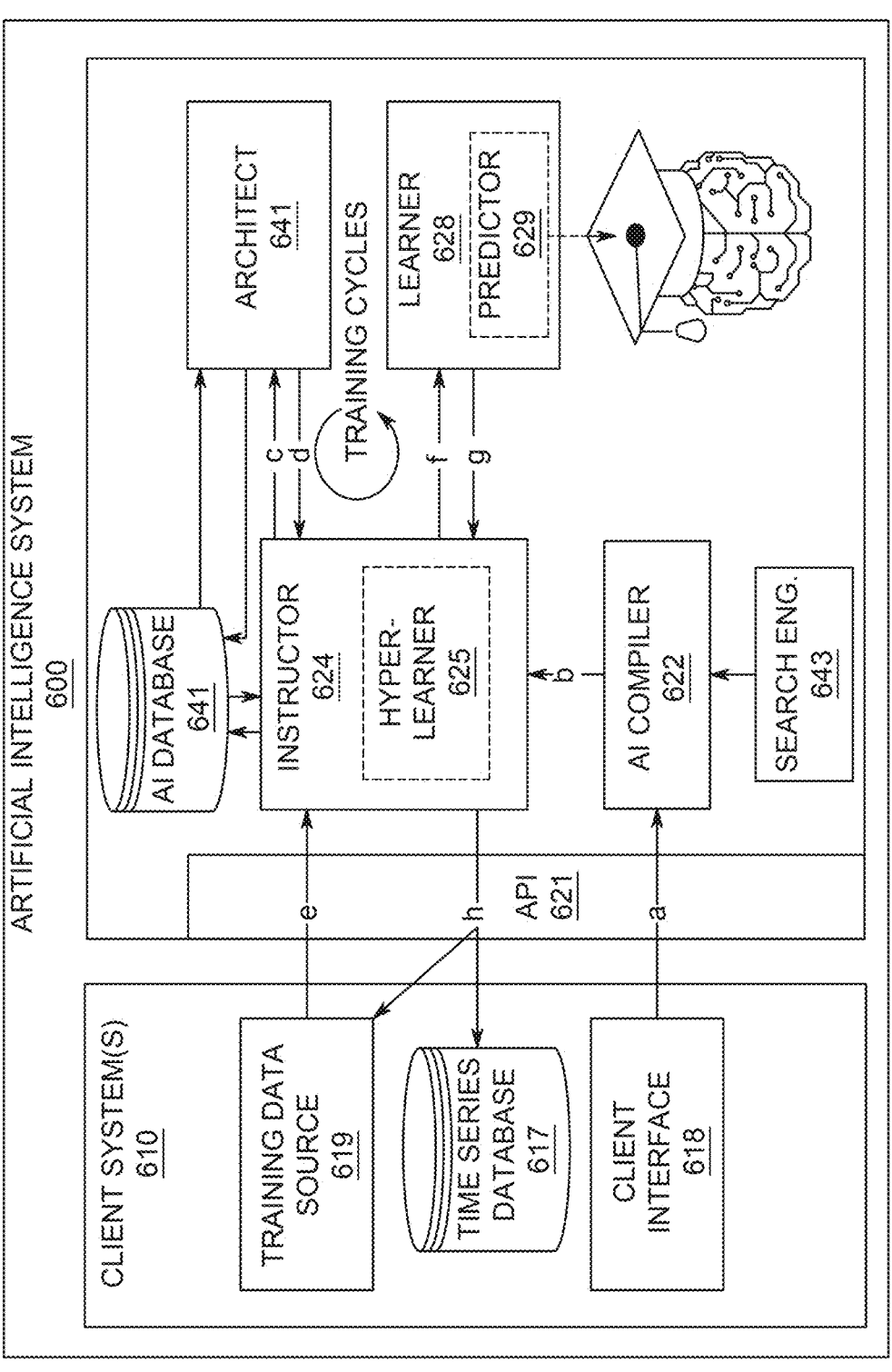
FIG. 25C illustrates a schematic diagram of one embodiment of ab AI engine having multiple independent modules on one or more computing platforms of the present invention.
Figure 25D:
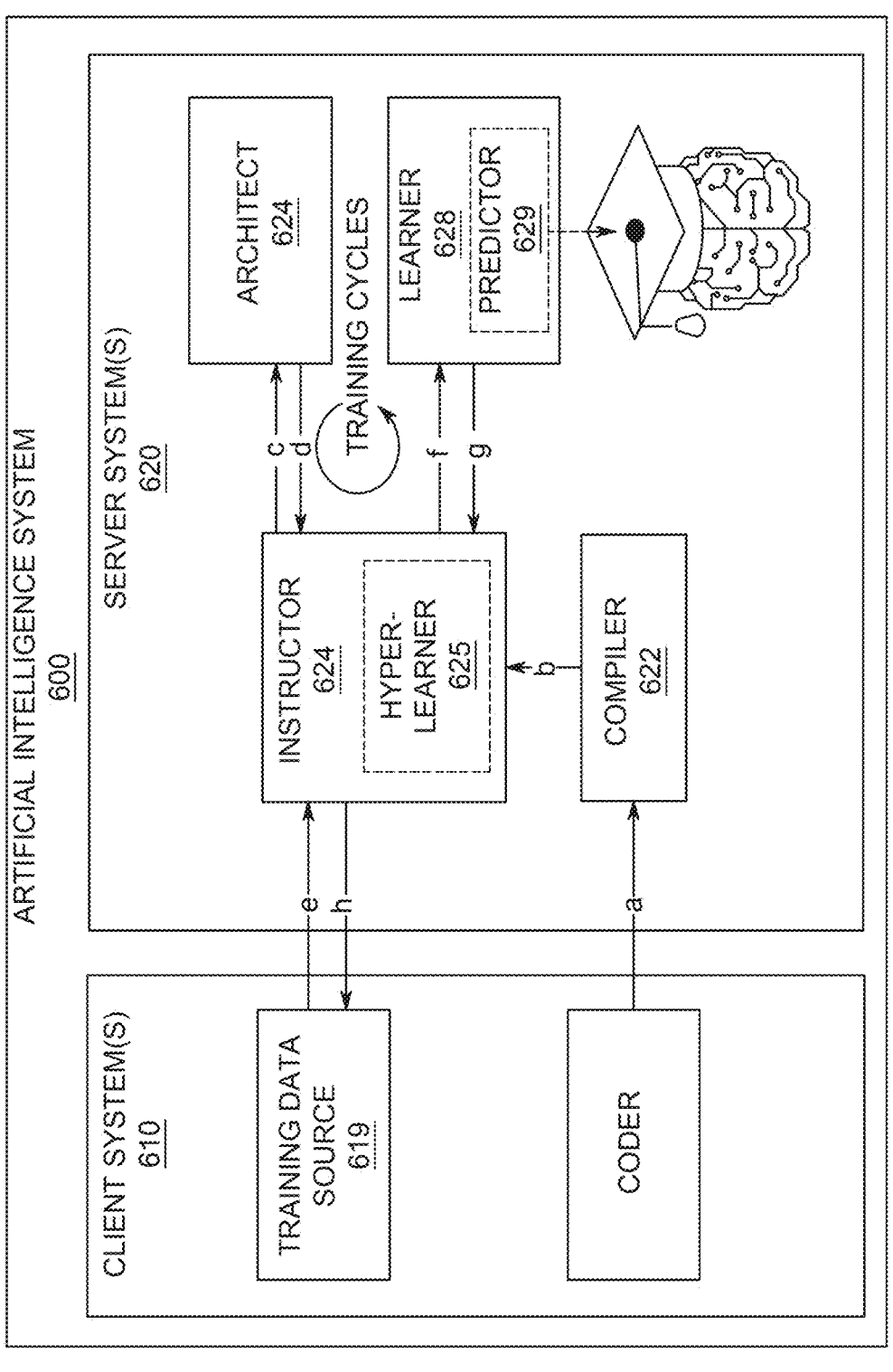
FIG. 25D illustrates a block diagram of an AI engine using one or more modules to create concept nodes in the graph of nodes in one embodiment of the present invention.
Figure 25E:
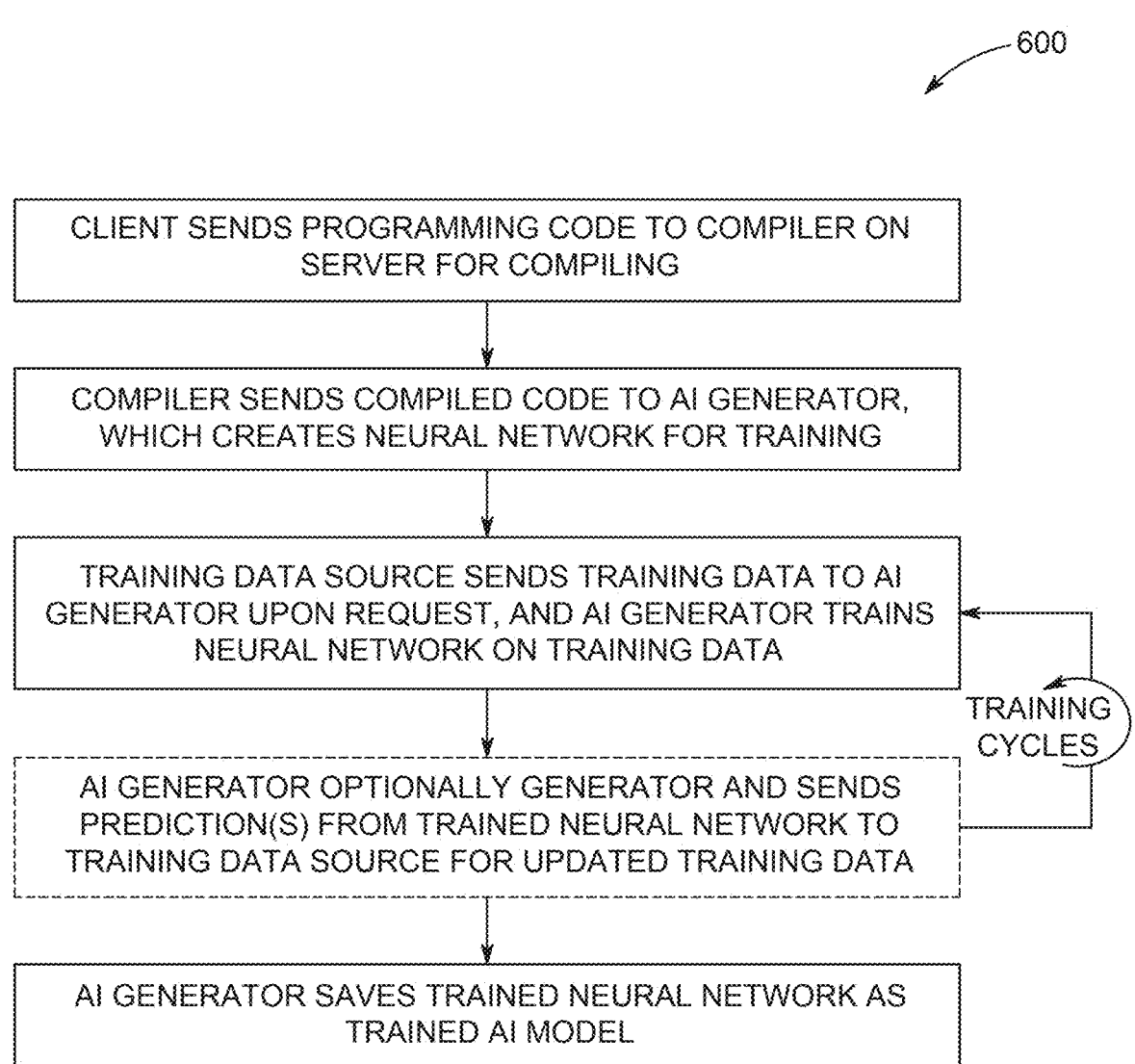
FIG. 25E illustrates one embodiment for a method associated with an AI system of FIGS. 25A through 25E of the present invention.

Referring to FIGS. 25A, 25B, and 25C, in one embodiment, a surgeon and/or assistant can seek from robotic surgery system 10 artificial intelligence from the server and/or an artificial intelligence engine (AI) engine 65. In one embodiment, the artificial intelligence engine 65 makes one or more of the following:

Image and Video Analysis

In one embodiment, enhanced imaging AI algorithms improve the quality and interpretation of medical imaging, providing surgeons with more detailed and accurate information during procedures.

As a non-limiting example, image recognition AI algorithms are used in real-time identification of anatomical structures, tumors, and critical tissues, assisting surgeons, and the like, in making more informed decisions.

Surgical Planning

In one embodiment, treatment planning AI algorithms analyze patient data, medical records, and imaging to assist in creating personalized surgical plans, considering individual variations and optimizing the robotic surgical approach. This is important with abnormal anatomy, Having an integrated overlay of imaging, within the view of the surgeon. This improves surgical accuracy in surgical oncology (particularly with partial nephrectomy or in untangling a tumor from surrounding nerves or blood vessels).

As a non-limiting example, risk assessment AI algorithms are used to predict potential complications, and assess the risks associated with specific procedures. This allows surgeons to make more informed decisions about the best course of action

Robot-Assisted Navigation

In one embodiment, path planning AI algorithms are used to plan optimal paths for robotic instruments, minimizing invasiveness and reducing the risk of damaging surrounding tissues.

As a non-limiting example, collision avoidance AI algorithms are used for the development of systems that can detect and prevent collisions between robotic instruments and anatomical structures in real-time.

Autonomous Robotics

In one embodiment steady hand assistance AI algorithms provide stability and precision to robotic instruments, compensating for hand tremors and improving the accuracy of movements.

Intraoperative Decision Support

In one embodiment, real-time feedback AI algorithms analyze real-time data from the surgery. This provides surgeons with instant feedback and suggestions to enhance decision-making during the procedure. As a non-limiting example, alert and warning AI algorithms issue alerts if deviations from a planned procedure, or potential issues, are detected. This allows for quick corrective actions.

Postoperative Monitoring and Analysis

In one embodiment, outcome prediction AI algorithms analyze postoperative data to predict patient outcomes and identify factors that contribute to successful surgeries or complications.

Continuous Learning and Improvement

As a non-limiting example, data analysis AI algorithms analyze large datasets of surgical procedures to identify patterns, trends, and best practices, contributing to ongoing improvements in surgical techniques and outcomes.

As a non-limiting example, adaptive systems AI helps develop robotic surgical systems 10 that continuously learn and adapt based on the experiences and feedback from various surgical procedures. This increases efficiency and reproducibility per surgeon.

In one embodiment, artificial intelligence engine 65 contains identifications and profiles of surgeons, assistants or third parties who have posted recommendations/ratings, as well as profiles for patients, surgeons, assistant and third parties, as well as usage feedback for videos and streamed media.

In one embodiment, AI engine 65 receives information from current and part surgeons, current and post assistants. A surgeon seeking to use the artificial intelligence engine 65 is presented (at some time) with a set of questions, or the surgical robotic system 10 obtains data inputs defining the characteristics of the surgeon, assistant or third party. In this case, the surgeon, assistant or third party characteristics generally define the context which is used to interpret or modify the basic goal of the surgeon, assistant or third party can define or modify the context at the time of use. Various considerations are used in a cluster analysis, in which recommendations relevant to the contexts may be presented, with a ranking according to the distance function from the "cluster definition." As discussed above, once the clustering is determined, advertisements may be selected as appropriate for the cluster, to provide a subsidy for operation of the system, and also to provide relevant information for the surgeon, assistant or third party about available products.

Clustering algorithms partition data into a certain number of clusters (groups, subsets, or categories), Important considerations include feature selection or extraction (choosing distinguishing or important features, and only such features); Clustering algorithm design or selection (accuracy and precision with respect to the intended use of the classification result; feasibility and computational cost; and the like); and to the extent different from the clustering criterion, optimization algorithm design or selection.

Finding nearest neighbors can require computing the pairwise distance between all points. However, clusters and their cluster prototypes might be found more efficiently. Assuming that the clustering distance metric reasonably includes close points, and excludes far points, then the neighbor analysis may be limited to members of nearby clusters, thus reducing the complexity of the computation, There are many situations in which a point could reasonably be placed in more than one cluster, and these situations are better addressed by non-exclusive clustering. In the most general sense, an overlapping or non-exclusive clustering is used to reflect the fact that an object can simultaneously belong to more than one group (class). A non-exclusive clustering is also often used when, for example, an object is "between" two or more clusters and could reasonably be assigned to any of these clusters. In a fuzzy clustering, every object belongs to every cluster with a membership weight. In other words, clusters are treated as fuzzy sets. Similarly, probabilistic clustering techniques compute the probability with which each point belongs to each cluster.

In many cases, a fuzzy or probabilistic clustering is converted to an exclusive clustering by assigning each object to the cluster in which its membership weight or probability is highest. Thus, the inter-cluster and intra-cluster distance function is symmetric. However, it is also possible to apply a different function to uniquely assign objects to a particular cluster.

A well-separated cluster is a set of objects in which each object is closer (or more similar) to every other object in the cluster than to any object not in the cluster, Sometimes a threshold is used to specify that all the objects in a cluster must be sufficiently close (or similar) to one another. The distance between any two points in different groups is larger than the distance between any two points within a group. Well-separated clusters do not need to be spherical, but can have any shape.

If the data is represented as a graph, where the nodes are objects and the links represent connections among objects, then a cluster can be defined as a connected component; i.e., a group of objects that are significantly connected to one another, but that have less connected to objects outside the group. This implies that each object in a contiguity-based cluster is closer to some other object in the cluster than to any point in a different cluster.

A density-based cluster is a dense region of objects that is surrounded by a region of low density. A density-based definition of a cluster is often employed when the clusters are irregular or intertwined, and when noise and outliers are present. DBSCAN is a density-based clustering algorithm that produces a partitional clustering, in which the number of clusters is automatically determined by the algorithm. Points in low-density regions are classified as noise and omitted; thus, DBSCAN does not produce a complete clustering.

A prototype-based cluster is a set of objects in which each object is closer (more similar) to the prototype that defines the cluster than to the prototype of any other cluster. For data with continuous attributes, the prototype of a cluster is often a centroid, i.e., the average (mean) of all the points in the cluster. When a centroid is not meaningful, such as when the data has categorical attributes, the prototype is often a medoid, i.e., the most representative point of a cluster. For many types of data, the prototype can be regarded as the most central point. These clusters tend to be globular. K-means is a prototype-based, partitional clustering technique that attempts to find a surgeon, assistant or third party-specified number of clusters (K), which are represented by their centroids, Prototype-based clustering techniques create a one-level partitioning of the data objects, There are a number of such techniques, but two of the most prominent are K-means and K-medoid. K-means defines a prototype in terms of a centroid, which is usually the mean of a group of points, and is typically applied to objects in a continuous n-dimensional space. K-medoid defines a prototype in terms of a medoid, which is the most representative point for a group of points, and can be applied to a wide range of data since it requires only a proximity measure for a pair of objects. While a centroid almost never corresponds to an actual data point, a medoid, by its definition, must be an actual data point.

In the k-means clustering technique K initial centroids are selected, the number of clusters desired. Bach point in the data set is then assigned to the closest centroid, and each collection of points assigned to a centroid is a cluster. The centroid of each cluster is then updated based on the points assigned to the cluster. We iteratively assign points and update until convergence (no point changes clusters), or equivalently, until the centroids remain the same. For some combinations of proximity functions and types of centroids, K-means always converges to a solution; i.e., K-means reaches a state in which no points are shifting from one cluster to another, and hence, the centroids do not change. Because convergence tends to b asymptotic, the end condition may be set as a maximum change between iterations. Because of the possibility that the optimization results in a local minimum instead of a global minimum, errors may be maintained unless and until corrected. Therefore, a human assignment or reassignment of data points into classes, either as a constraint on the optimization, or as an initial condition, is possible.

To assign a point to the closest centroid, a proximity measure is required. Euclidean (L2) distance is often used for data points in Euclidean space, while cosine similarity may be more appropriate for documents. However, there may be several types of proximity measures that are appropriate for a given type of data. For example, Manhattan (L1) distance can be used for Euclidean data, while the Jaccard measure is often employed for documents. Usually, the similarity measures used for K-means are relatively simple since the algorithm repeatedly calculates the similarity of each point to each centroid, and thus complex distance functions incur computational complexity. The clustering may be computed as a statistical function, e.g., mean square error of the distance of each data point according to the distance function from the centroid. Note that the K-means may only find a local minimum, since the algorithm does not test each point for each possible centroid, and the starting presumptions may influence the outcome. The typical distance functions for documents include the Manhattan (L1) distance, Bregman divergence, Mahalanobis distance, squared Euclidean distance and cosine similarity, An optimal clustering can be obtained as long as two initial centroids fall anywhere in a pair of clusters, since the centroids will redistribute themselves, one to each cluster. As the number of clusters increases, it is increasingly likely that at least one pair of clusters will have only one initial centroid, and because the pairs of clusters are further apart than clusters within a pair, the K-means algorithm will not redistribute the centroids between pairs of clusters, leading to a suboptimal local minimum. One effective approach is to take a sample of points and cluster them using a hierarchical clustering technique. K clusters are extracted from the hierarchical clustering, and the centroids of those clusters are used as the initial centroids. This approach often works well, but is practical only if the sample is relatively small, e.g., a few hundred to a few thousand (hierarchical clustering is expensive), and K is relatively small compared to the sample size. Other selection schemes are also available.

In the one embodiment, space requirements for K-means are modest because only the data points and centroids are stored. Specifically, the storage required is O((m+K)n), where m is the number of points and n is the number of attributes. The time requirements for K-means are also modest-basically linear in the number of data points. In particular, the time required is O(I×K×m×n), where I is the number of iterations required for convergence. As mentioned, I is often small and can usually be safely bounded, as most changes typically occur in the first few iterations. Therefore, K-means is linear in m, the number of points, and is efficient as well as simple provided that K, the number of clusters, is significantly less than m.

In the one embodiment, outliers can unduly influence the clusters, especially when a squared error criterion is used. However, in some clustering applications, the outliers should not be eliminated or discounted, as their appropriate inclusion may lead to important insights. In some cases, such as financial analysis, apparent outliers, e.g., unusually profitable investments, can be the most interesting points.

Hierarchical clustering techniques are a second important category of clustering methods. There are two basic approaches for generating a hierarchical clustering; Agglomerative and divisive. Agglomerative clustering merges close clusters in an initially high dimensionality space, while divisive splits large clusters. Agglomerative clustering relies upon a cluster distance, as opposed to an object distance. For example, the distance between centroids or medoids of the clusters, the closest points in two clusters, the further points in two clusters, or some average distance metric, Ward's method measures the proximity between two clusters in terms of the increase in the sum of the squares of the errors that results from merging the two clusters, Agglomerative Hierarchical Clustering refers to clustering techniques that produce a hierarchical clustering by starting with each point as a singleton cluster and then repeatedly merging the two closest clusters until a single, all-encompassing cluster remains. Agglomerative hierarchical clustering cannot be viewed as globally optimizing an objective function. Instead, agglomerative hierarchical clustering techniques use various criteria to decide locally, at each step, which clusters should be merged (or split for divisive approaches). This approach yields clustering algorithms that avoid the difficulty of attempting to solve a hard combinatorial optimization problem. Furthermore, such approaches do not have problems with local minima or difficulties in choosing initial points. Of course, the time complexity of O(m2 log m) and the space complexity of O(m2) are prohibitive in many cases. Agglomerative hierarchical clustering algorithms tend to make good local decisions about combining two clusters since they can use information about the pair-wise similarity of all points. However, once a decision is made to merge two clusters, it cannot be undone at a later time. This approach prevents a local optimization criterion from becoming a global optimization criterion.

In supervised classification, the evaluation of the resulting classification model is an integral part of the process of developing a classification model. Being able to distinguish whether there is non-random structure in the data is an important aspect of cluster validation.

In one embodiment, a k-means algorithm is used as follows:

The K Means Clustering algorithm finds observations in a dataset that are like each other and places them in a set. The process starts by randomly assigning each data point to an initial group and calculating the centroid for each one. A centroid is the center of the group. Note that some forms of the procedure allow you to specify the initial sets.

Then the algorithm continues as follows: it evaluates each observation, assigning it to the closest cluster. The definition of "closest" is that the Euclidean distance between a data point and a group's centroid is shorter than the distances to the other centroids.

When a cluster gains or loses a data point, the K means clustering algorithm recalculates its centroid. The algorithm repeats until it can no longer assign data points to a closer set.

When the K means clustering algorithm finishes, all groups have the minimum within-cluster variance, which keeps them as small as possible. Sets with minimum variance and size have data points that are as similar as possible. There is variability amongst the characteristics in each cluster, but the algorithm minimizes it.

In the one embodiment, the observations within a set should share characteristics. In some cases, the analysts might need to specify different numbers of groups to determine which value of K produces the most useful results.

In one embodiment, an artificial intelligence engine 65 is used to predict what will happen; or prescriptive, meaning using data to make suggestions about what action to take. As a nonlimiting example, AI provides predictive information about a patient's health.

As a non-limiting example, AI engine 65 is used for systems with a deep learning networks with many layers. The layered network can process extensive amounts of data and determine the "weight" of each link in the network for example, in an image recognition system, some layers of the neural network might detect individual features of a face, like eyes, nose, or mouth, while another layer would be able to tell whether those features appear in a way that indicates a face.

In the one embodiment, there are many different AI engines 65 that can be trained to generate suitable output values for a range of input values; the neuro-fuzzy logic engine 65 is merely one embodiment.

In the one embodiment, measurement data, the information feeds, and the output parameters may be used to train an AI engine 65 to control the one or more devices in response to the measurement data and information feeds In one embodiment, AI engines 65 can be trained to recognize temporal patterns.

In one embodiment, measurement data, the information feeds, and the output parameters may be used to train an AI engine 65 to control the one or more devices in response to the measurement data and information feeds.

In one embodiment, illustrated in FIGS. 25A through 25E a computing system 664 includes a logic subsystem 666 and a storage subsystem 668. Computing system 664 may further include an input subsystem 670, an output subsystem 672, a communication subsystem 674, and/or other components not shown in FIGS. 25A through 25E In the one embodiment, logic subsystem 666 may include one or more physical logic devices configured to execute programmed instructions 667 of surgical computing device 151. For example, the logic subsystem 666 may be configured to execute programmed instructions 67 of surgical computing device 151 that are part of one or more applications, services, programs, routines, libraries, objects, components, data structures, or other logical constructs. Such programmed instructions 67 of surgical computing device 151 may be implemented to perform a task, implement a data type, transform the state of one or more components, achieve a technical effect, or otherwise arrive at a desired result.

In the one embodiment, logic subsystem 666 includes one or more processors 62 (as an example of physical logic devices) configured to execute software programmed instructions 67 of surgical computing device 151. Additionally, or alternatively, the logic subsystem 666 may include one or more hardware and/or firmware logic machines (as an example of physical logic devices) configured to execute hardware or firmware programmed instructions 67 of surgical computing device 151. Processors 62 of the logic subsystem may be single-core or multi-core, and the programmed instructions 67 of surgical computing device 151 executed thereon may be configured for sequential, parallel, and/or distributed processing. Individual components of the logic subsystem may be distributed among two or more separate devices, which may be remotely located and/or configured for coordinated processing. Aspects of the logic subsystem may be virtualized and executed by remotely accessible, networked computing devices configured in a cloud-computing configuration.

In the one embodiment, storage subsystem 668 includes one or more physical, non-transitory memory devices configured to hold programmed instructions 67 of surgical computing device 151 executable by the logic subsystem in non-transitory form, to implement the methods and processes described herein. When such methods and processes are implemented, the state of storage subsystem 68 may be transformed. e.g., to hold different data. Storage subsystem 68 may include removable and/or built-in devices. Storage subsystem 668 may include optical memory devices, semiconductor memory devices, and/or magnetic memory devices, among other suitable forms. Storage subsystem 668 may include volatile, nonvolatile, dynamic, static, read/write, read-only, random-access, sequential-access, location-addressable, file-addressable, and/or content-addressable devices. Aspects of logic subsystem 666 and storage subsystem 68 may be integrated together into one or more hardware-logic components. While storage subsystem 668 includes one or more physical devices, aspects of the programmed instructions 67 of surgical computing device 151 described herein alternatively may be propagated by a communication medium (e.g., an electromagnetic signal, an optical signal, etc.) that is not necessarily held by a physical device for a finite duration.

In one embodiment, an AI generator 623 generates the trained neural network 606 and can include one or more AI-generator modules selected from at least an instructor module 624, an architect module 626, and a learner module 628. The instructor module 624, the architect module 626, and the learner module 628 can respectively be referred to herein as the Instructor, the Architect, and the Learner. The instructor module 624 can optionally include hyperlearner module 625, which can be referred to herein as the hyperlearner, and which can be configured to select one or more hyperparameters for any one or more of a neural network configuration, a learning algorithm, a learning optimizer, and the like. Before selecting the one or more hyperparameters, the hyperlearner module 625 can access a database of solution statistics gathered from one or more repositories of previous problems and previously built AI models therefor and take a fingerprint of a sample of available data by using random predictions. The hyperlearner module 625 can optionally be contained in a different AI-generator module such as the architect module 626 or the learner module 628, or the hyperlearner module 625 can be an AI-generator module itself. The learner module 628 can optionally include a predictor module 629, which can be referred to herein as the Predictor, and which can provide one or more predictions for a trained neural network such as the trained neural network 106 hosted in a prediction mode. The predictor module 629 can optionally be contained in a different AI-generator module such as the instructor module 624 or the architect module 326, or the predictor module 629 can be an AI-generator module itself. The AI generator 623 including the foregoing one or more AI-generator modules can be configured to generate the trained neural network from compiled code via one or more training cycles in the AI generator 623.

In the one embodiment, an AI database, such as AI database 741, hosted on cloud platform 76 is configured to cooperate with AI engine 65. In an embodiment, the AI database stores and indexes trained AI objects and its class of AI objects have searchable criteria. The AI database cooperates with AI search engine 65 to utilize search criteria supplied from a surgeon, assistant or third party, from one or more of: scripted software code; and data put into defined fields of a surgeon, assistant or third party interface 61 can search engine 65 utilizes the search criteria in order for AI search engine 65 to retrieve one or more AI data objects that have already been trained as query results. The AI database is coupled to AI engine 65 to allow any of reuse, reconfigure ability, and recomposition of the one or more trained AI data objects from the AI database into a new trained AI model. These and other features of the design provided herein can be better understood with reference to the drawings, description, and claims, all of which form the disclosure of this patent application.

In one embodiment, a surgeon or assistant can search the database, that can be a medical device database based on one or more of the surgical procedure to be performed, the anatomical characteristics, and the surgical instrument kinematics using the above-described metadata to identify structural relationships for the video and information of interest. Additionally, in one aspect, the surgical planning tool includes a computer-based morphology matching and analysis algorithm. In one aspect, the morphology matching algorithm is selected through videos stored on an electronic medical records database to identify correlations between visual characteristics in the video records and associated metadata identifications made by medical personnel. The surgical planning tool can apply these correlations to newly encountered anatomical structures to help medical personnel performing the procedure determine patient anatomy, preferred surgical approaches, disease states, potential complications, and the like.

In one embodiment, a surgeon or assistant can search the database, that uses a morphology matching algorithm and look for recorded motion map image information and optionally kinematic information to identify correlations between anatomical features (such as geometry) and instrument motion. This morphology can be useful, for example, to identify various anatomical features associated with various instrument motions. This modality can also be useful, for example, to identify various anatomical features that are not associated with various instrument motions. For example, this morphological information can be used as a basis for generating surgical guidance to present to the surgeon during surgery. For example, this morphological information can be used as a basis for arresting or imparting certain surgical instrument motion to the surgical procedure during the surgical procedure.

In one embodiment, a morphology matching algorithm is coupled to the database, and can access recorded motion map image information to identify correlations between anatomical features (such as geometry) and reactive forces imparted by tissue structures in response to touches by the surgical instrument. This modality can be useful, for example, to identify correlations between visualized anatomical tissue structures and tactile feedback imparted by the tissue structures in response to palpation by a robotically-assisted instrument. In some embodiments, the correlated motion map image morphology and tactile feedback information is associated with an expert surgeon diagnostic assessment used in surgeon training.

In one embodiment, a surgeon or assistant can search the database with relevant information of one or more of the surgical procedure to be performed In one embodiment, the database can include past procedures information of third parties and/or the patient, including electronic medical records, imaging data, and the like.

In one embodiment, a surgeon or assistant can search the database and includes relevant information of a surgical procedure to be performed The surgeon can define the tissue as the desired type, and the database can include image recognition information that can be updated and the robot 20 proceeds.

In one embodiment, a surgeon or assistant can search the database and utilize AI to operate one or more surgical robot systems 10, an AI guidance system, an image recognition system, an image recognition database, and/or a database of past procedures, electronic medical records, and/or imaging data. The image recognition system may identify the tissue type present in the patient. If it is the desired or targeted tissue type, the AI guidance system may remove that tissue using an end effector on the surgical robot. The surgeon can define the tissue type if the image recognition system identified the tissue as anything other than the desired tissue type to perform a procedure. The system can identify anatomical features, abnormalities, tissue margins, tissue characteristics, tissue types, tissue interfaces, or combinations thereof based on, for example, preset criteria, physician input, etc. For example, the image recognition system can evaluate images to identify landmarks and generate a surgical plan based, at least in part, on those landmarks. The landmarks can be identified by the system, physician, or both. In some procedures, the landmarks can be identifiable anatomical features (e.g., spinous processes, bony protrusions, facet joints, nerves, spinal cord, intervertebral disc, vertebral endplates, etc.) along the patient's spine to generate a surgical plan.

Robotic surgical system 10 and methods can use images obtained prior to and/or during surgery to guide a robotic surgical apparatus, end effector, surgical tool, or the like. Robotic surgical system 10 can access a database to that has information covering the entirety of a surgical procedure.

Robotic surgical system 10, and methods, can monitor a patient's brain activity during surgery to determine a level of consciousness, patient response during a procedure, or the like. For example, using of a wireless EEG system during surgery can provide a basis for determining the amount of medication to give a patient. The EEG can track the amount of discomfort the patient is experiencing, and more medication (i.e., anesthesia) can be administered if the amount of discomfort exceeds a threshold. The system can include an AI unit that receive monitored brain activity data (e.g., brain activity patterns, brain activity spikes, and the like.) and identify correlations with anesthesia based adverse events. Pain, discomfort, and other patient parameters can be monitored and evaluated to determine whether to modify the treatment plan, administer anesthesia, etc. The AI/machine learning can be used to analyze brain activity, patient feedback, or other patient parameters to, for example, improve safety, comfort, or the like.

Robotic surgical system 10 and methods can access the database for measurement of various parameters in a database, associated with an end effector before, during, and/or after a surgical action or procedure. The monitored parameters can include rpms, angle, direction, sound, or the like. The monitored parameters can be combined with location data, tissue type data, and/or metadata to train an AI system 42 for guiding a robotic surgical tool to automatically perform a surgical action, procedure, or an entire surgery.

Robotic surgical system 10 and methods can access the database and be implemented in a computing system for at least partially controlling a robotic surgical apparatus to perform surgical actions by obtaining a first image of a region of interest associated with a subject. A type of tissue shown in the first image can be identified based, at least in part, on a neural network model trained on an image training set. In response to determining that the identified type of tissue belongs to a set of targeted types, causing the robotic surgical apparatus to perform a first surgical action with respect to the region of interest in accordance with a surgical plan. A second image of the region of interest can be obtained after completion of the first surgical action. Additionally surgical steps can be performed.

In one embodiment, robotic surgical system 10 can access a computer-readable storage medium storing content that, when executed by one or more processors 62, causes the one or more processors 62 to perform actions including obtaining first image of a region of interest associated with a surgery subject, and identifying a type of tissue shown in the first image based, at least in part, on a neural network model. In response to determining that the identified type of tissue belongs to a set of targeted types, robotic surgical apparatus performs a first surgical action with respect to the region of interest in accordance with a surgical plan. A second image of the region of interest is obtained after completion of the first surgical action. The actions can include displaying types of tissue comprises displaying one or more boundary indicators for indicating at least one of targeted tissue to be removed, protected tissue, delivery instrument placement, or an end effector working space within the subject.

In general, AI database stores and indexes trained AI objects and its class of AI objects have searchable criteria. AI database cooperates with search engine 65 to utilize search criteria supplied from a surgeon, assistant or third party to retrieve one or more AI data objects that have already been trained as query results. The AI database is coupled to AI engine 65 to allow any of reuse, reconfigure ability, and recomposition of the one or more trained AI data objects from the AI database into a new trained AI model.

In one embodiment, AI engine 65 (600) includes multiple independent modules on one or more computing platforms, where the architect module is configured to create one or more concept nodes by wrapping each external entity of code into a software container with an interface configured to exchange information in a protocol of a software language used by that external entity of code in accordance with an embodiment.

As shown, the AI system 42 (600) includes one or more client systems 610 and one or more server systems 620, wherein each server system or any two or more servers' systems of the one or more server systems 620 can be referred to herein as an AI engine 65. The one or more client systems 610 can be client systems and include a coder 612 or coding means for generating programming code such as programming code in a pedagogical programming language (e.g., Inkling™). The one or more client systems 610 can further include a training data source 614. As a non-limiting example, the training data source 614 can alternatively be included in the one or more server systems 620, or the training data source 614 can be include in both the one or more client systems 610 and the one or more server systems 620. The one or more server systems 620 can be server systems and include a compiler for the programming code and an AI generator 623 for generating the trained neural network via one or more training cycles in the AI generator 623.

One or more client systems 610 and the one or more server systems 620, it should be understood that the one or more client systems 610 and the one or more server systems 620 need not be deployed exactly as shown or with local and remote systems tele communicatively coupled over substantially large geographic distances. The one or more client systems 610, the one or more server systems 620, or one or more components thereof can be deployed at a single geographic location such as in a building or room of the building. Moreover, the one or more client systems 610 and the one or more server systems 620 can be deployed in a single system such as a powerful, single-enclosure machine. As used herein, the foregoing refers to so-called on-premises installations, which is another operating environment for building AI, training AI, deploying AI, or a combination thereof.

In an embodiment, other independent processes cooperate together and contain functionality from the instructor module, the learner module, etc. For example, a scholar process is coded to handle both the training for a given concept (lesson management) and training a lesson. The scholar process trains a given concept (e.g. does the job of instructor and learner in an alternative architecture). When the AI engine 65 trains the same concept or multiple different concepts in parallel then the AI engine 65 will have multiple scholars running in parallel. A director module manages the training of a concept graph. A conductor process merely manages resource allocation required for training an AI model. The director module determines how the resources are used to train the graph of nodes in parallel. Each concept is trained by a scholar process and in the case of multiple concepts being trained in parallel multiple scholar processes are run simultaneously. This is all managed by the director module.

Figure 26A:
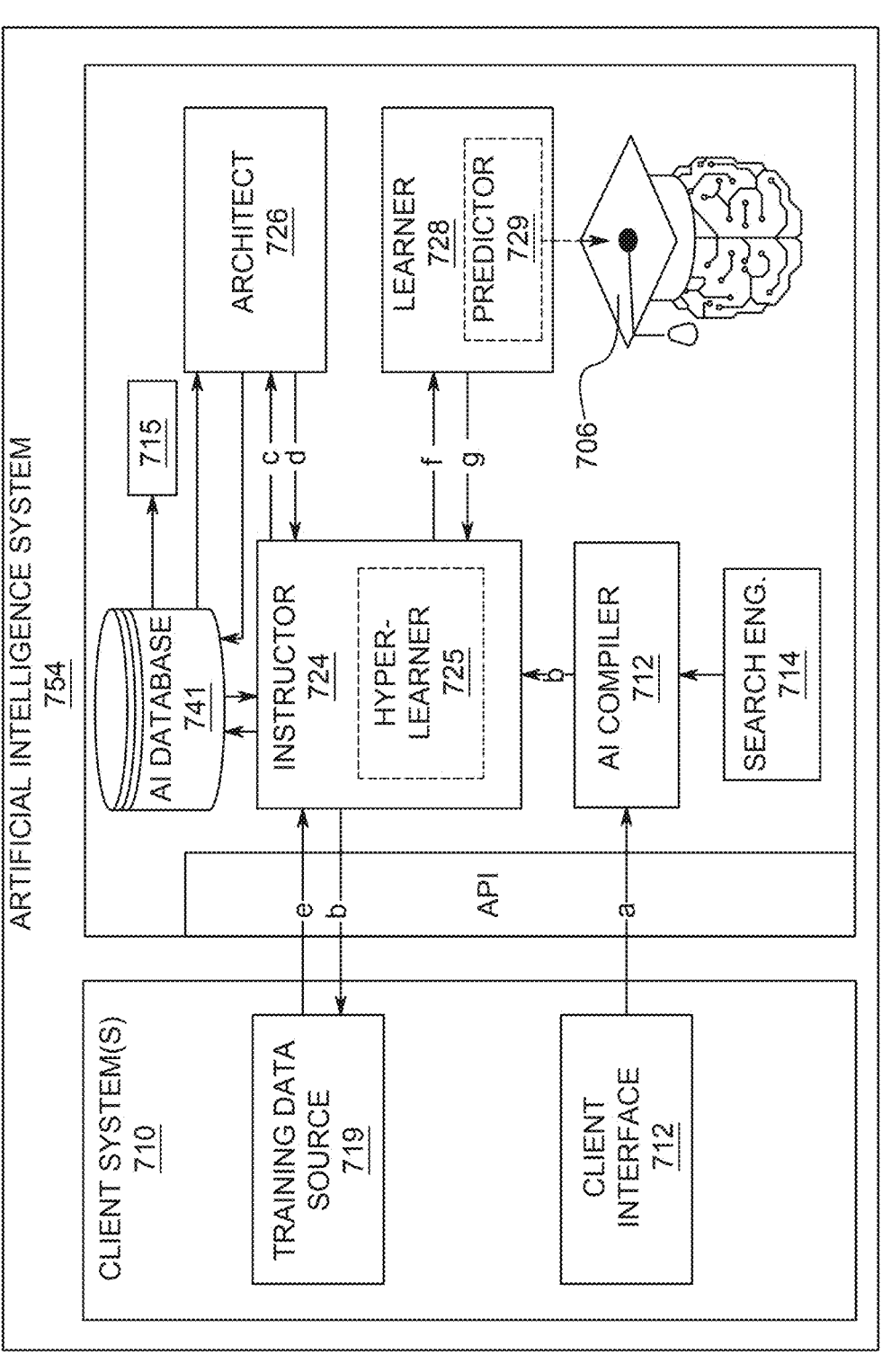
FIG. 26A illustrates one embodiment of an artificial intelligence system of the present invention.
Figure 26B:
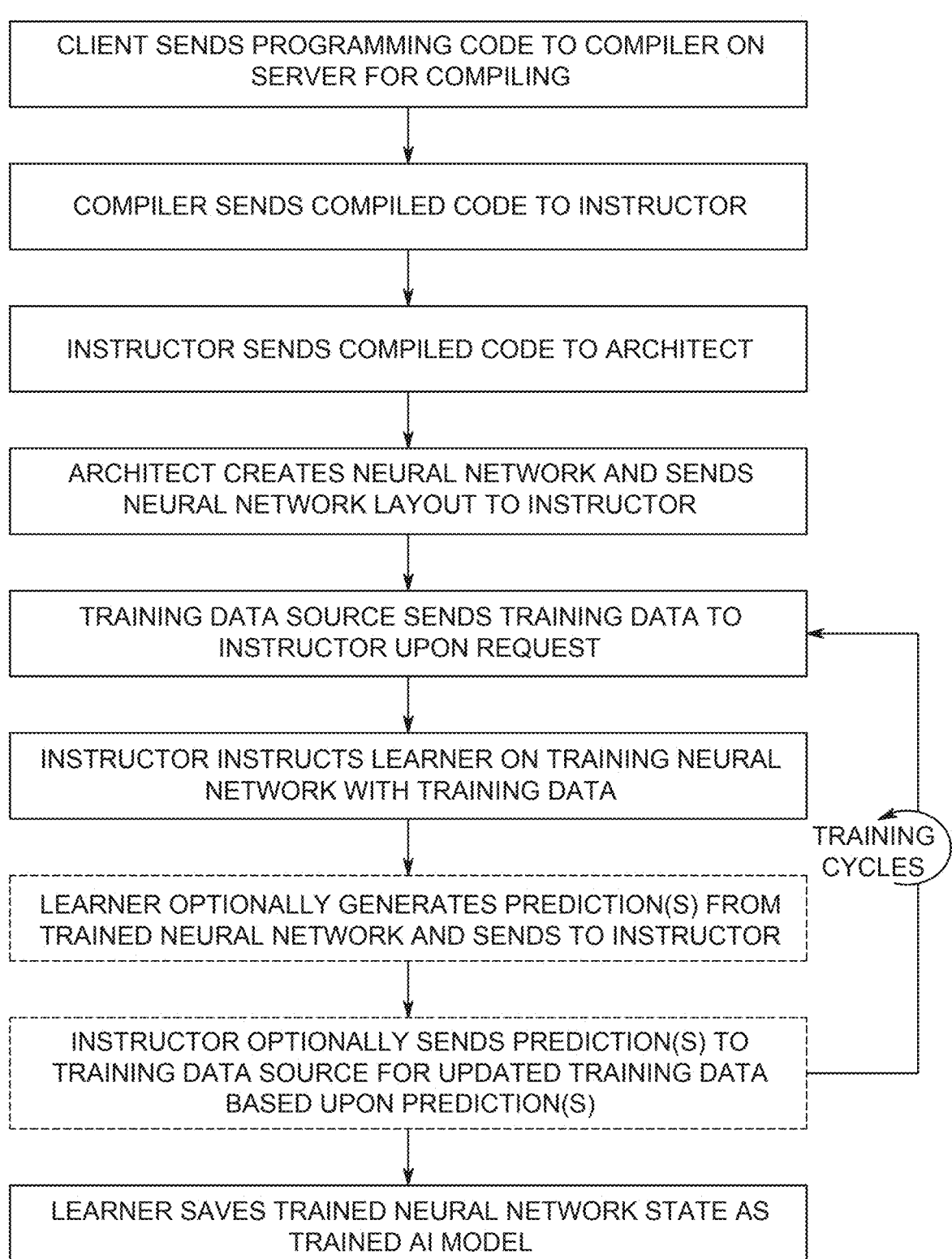
FIG. 26B is a block diagram illustrates an embodiment of a method using the FIG. 26A AI system of the present invention.

As illustrated in FIGS. 26A and 26B in response to received data, the AI database 741 ^% stores and indexes trained AI objects and the class of AI objects have searchable criteria.

The AI database 741 of searchable AI objects indexes parameters and characteristics known about the AI objects that allows searching of surgeon, assistant or third party supplied criteria from either or both of: scripted code and defined fields in a surgeon, assistant or third party interface.

In the one embodiment, AI engine 65 utilizes this search criteria supplied from the current or past surgeons and current and past surgeons, current and past algorithms, newly or partially created algorithms. This is achieved through scripted software code, data put into defined fields of a surgeon, assistant or third party interface, and the like, in order for AI engine 65 to find and retrieve relevant AI data objects that have already been trained as query results. In 0 . . . itself, because the untrained model has not yet been trained. In the one embodiment, engine is 65 use of the surgeon, assistant or third party supplied search criteria from the surgeon, assistant or third party interfaces to find relevant trained AI objects stored in the AI data will be described in more detail later.

AI database can index AI objects corresponding to the main concept and the set of sub concepts making up a given trained AI model so that reuse, recomposition, and reconfiguration of all or part of a trained AI model is possible.

AI database 741 can be also coupled to AI engine 65 to allow any of reuse, reconfigure ability, and recomposition of the one or more trained AI data objects into a new trained AI model. As a non-limiting example, AI engine 65 can generates AI models, such as a first AI model. The AI database 741 may be part of and cooperate with various other modules of AI engine 65. In one embodiment, AI engine 65 has a set of surgeon, assistant or third party interfaces 112 to import from either or both 1) scripted software code written in a pedagogical software programming language, such as Inkling, and/or 2) from the surgeon, assistant or third party interface 712 with defined fields that map surgeon, assistant or third party supply criteria to searchable criteria of the AI objects indexed in AI database 741

AI database 741 can be part of cloud-based AI service. AI database 741 can be hosted on cloud platform with the search engine 715 (65).

As a non-limiting example, AI database 741 cooperates with AI engine 65. AI engine 65 can further include an architect module 126, an instructor module 124, and a learner module 128. In the one embodiment, architect module 126 creates and optimizes learning topologies of an AI object, such as the topology of a graph of processing nodes, for the AI objects. The instructor module 724 carries out a training plan codified in a pedagogical software programming language. The learner module 728 carries out an actual execution of the underlying AI learning algorithms during a training session. The architect module 726, when reconfiguring or recomposing the AI objects, composes one or more trained AI data objects into a new AI model and then the instructor module 724 and learner module 728 cooperate with one or more data sources to train the new AI model.

Surgeon, assistant or third party interface, to the AI database 741 and search engine 715, can be configured to present a population of known trained AI objects. In the one embodiment, search engine 715 cooperates with the AI database 741 is configured to search the population of known trained AI objects to return a set of one or more already trained AI objects similar to a problem trying to be solved by the surgeon, assistant or third party supplying the search criteria.

The database management system tracking and indexing trained AI objects corresponding to concepts is configured to make it easy to search past experiments, view results, share with others, and start new variants of a new trained AI model.

In the one embodiment, AI database 741 may be an object orientated database, a relational database, or other similar database, that stores a collection of AI objects (i.e., the trained main concept and sub concepts forming each trained AI model). The AI database 741 can be composed of a set of one or more databases in which each database has a different profile and indexing, where the set of databases are configured to operate in a parallel to then send back accurate, fast, and efficient returns of trained AI objects that satisfy the search query.

In the one embodiment, AI engine 65 generates a trained AI model 706 and can include one or more AI-generator modules selected from at least an instructor module 724, an architect module 726, and a learner module 728 as shown. The instructor module 724 can optionally include a hyperlearner module 725, and which can be configured to select one or more hyperparameters for any one or more of a neural network configuration, a learning algorithm, a learning optimizer, and the like. The hyperlearner module 725 can optionally be contained in a different AI-generator module such as the architect module 726 or the learner module 728, or the hyperlearner module 725 can be an AI-generator module itself. The learner module 732 can optionally include a predictor module 729, which can provide one or more predictions for a trained AI model. The predictor module 729 can optionally be contained in a different AI-generator module such as the instructor module 724 or the architect module 726, or the predictor module 729 can be an AI-generator module itself. AI engine 65 can generate the trained AI model 706, such as trained AI model 706, from compiled scripted software code written in a pedagogical software programming language via one or more training cycles with AI engine 65.

One or more surgeons, assistants and the like 710 can make a submission to create a trained AI model. Once a Mental Model and Curricula have been coded in the pedagogical software programming language, then the code can be compiled and sent to the three main modules, the learner module 728, the instructor module 724, and the architect module 726 of AI engine 65 for training. One or more surgeon, assistant or third party interfaces 712, such a web interface, a graphical surgeon, assistant or third party interface, and/or command line interface, will handle assembling the scripted code written in the pedagogical software programming language, as well as other ancillary steps like registering the line segments with AI engine 65, together with a single command. However, with each module of the AI compiler module 722, the web enabled interface to AI engine 65, the learner module 728 be used in a standalone manner, so if the author prefers to manually invoke the AI compiler module, manually perform the API call to upload the compiled pedagogical software programming language to the modules of AI engine 65, and the like As a non-limiting example, one or more clients 710 can send scripted code from a coder 712 or another surgeon, assistant or third party interface to AI compiler 722. AI compiler 722 compiles the scripted software code written in a pedagogical software programming language. AI compiler 722 can send the compiled scripted code, similar to an assembly code, to the instructor module 724, which, in turn, can send the code to the architect module 726. In one embodiment, AI compiler 222 can send the compiled scripted code in parallel to all of the modules needing to perform an action on the compiled scripted code. The architect module 726 can propose a vast array of machine learning algorithms, such as various neural network layouts, as well as optimize the topology of a network of intelligent processing nodes making up an AI object. The architect module 726 can map between concepts and layers of the network of nodes and send one or more instantiated AI objects to the learner module 728. Once the architect module 726 creates the topological graph of concept nodes, hierarchy of sub concepts feeding parameters into that main concept (if a hierarchy exists in this layout), and learning algorithm for each of the main concept and sub concepts, then training by the learner module 728 and instructor module 724, which can be couped to a hyper learner 725, can begin.

The instructor module 724 can request training data from the training data source 219. Training can be initiated with an explicit start command in the pedagogical software programming language from the surgeon, assistant or third party to begin training. In order for training to proceed, the surgeon, assistant or third party needs to have already submitted compiled pedagogical software programming language code and registered all of their external data sources such as simulators (if any are to be used) via the surgeon, assistant or third party interfaces with the learner and instructor modules 724, 726 of AI engine 65.

The training data source 719 can send the training data to the instructor module 724 upon the request. The instructor module 724 can subsequently instruct the learner module 728 on training the AI object with pedagogical software programming language based curricula for training the concepts into the AI objects. Training an AI model 706 can take place in one or more training cycles to yield a trained state of the AI model 706. The instructor module 724 can decide what pedagogical software programming language based concepts and streams should be actively trained in a mental model. The instructor module 724 can know what are the terminating conditions for training the concepts based on surgeon, assistant or third party criteria and/or known best practices. The learner module 728 or the predictor 729 can elicit a prediction from the trained AI model 706 and send the prediction to the instructor module 724. The instructor module 724, in turn, can send the prediction to the training data source 719 for updated training data based upon the prediction and, optionally, instruct the learner module 328 in additional training cycles. When the one or more training cycles are complete, the learner module 728 can save the trained state of the network of processing nodes in the trained AI model 706. (Note a more detailed discussion of different embodiments of the components making up AI engine 65 occurs later.)

The AI database 741 may consist of a storage layer which is configured to know how to efficiently store database objects, in this case AI objects, an indexing mechanism to speed retrieval of the stored AI objects, engine 715 to translate a query request into a retrieval strategy to retrieve AI objects that satisfy a query, and a query language which describes to the AI database 741 what AI objects are desired to be retrieved.

As a non-limiting example, search engine 715 is configured to parse scripted software code written in a pedagogical software programming language and then map that to one or more searchable criteria as well as 2) import the data put into defined fields of the surgeon, assistant or third party interface to use as searchable criteria to find relevant trained AI objects indexed in the AI database 741. In an embodiment, the search engine 715 is configured to also be able to do a natural language search of a submitted description from a surgeon, assistant or third party to determine what a similar trained object would be by referencing the: indexed criteria and/or signatures and/or example models in the database.

In one embodiment, AI database 741 is indexed with keywords and problems solved about each stored AI object In one embodiment, search engine 715 in query results will return relevant AI objects. The relevant AI objects can be evaluated and return based on a number of different weighting factors including number of resources consumed to train that concept learned by the AI object In one embodiment, search engine 715 information from the current surgeon, prior surgeons who have performed similar surgeries, assistants, prior assistants, can provide information for relevant trained AI objects. In an embodiment, search engine 743 refers to: the signatures of the stored AI objects as well as; any indexed parameters for the AI objects indexed by the AI database 741.

In an embodiment, the AI database 741 and search engine 715 build an index of algorithms and parameters that have been tried in past.

Figure 27:
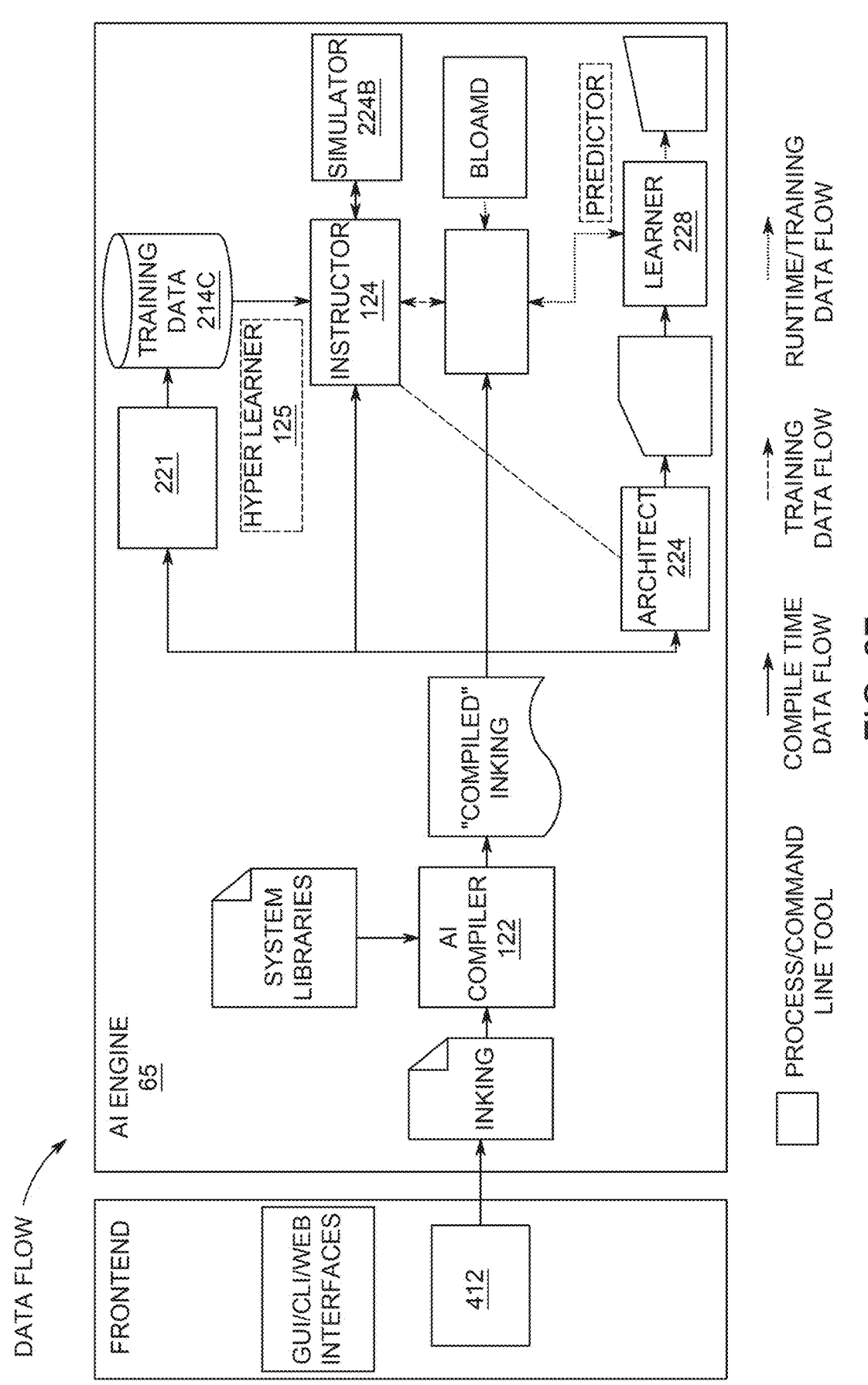
FIG. 27 provides a block diagram of an AI engine using an interface infrastructure to allow uploading of user code and data from their local development environment into the AI engine learning framework, via the user files specified in a file, such as a project file, associated with the container in accordance with an embodiment.
Figure 28:
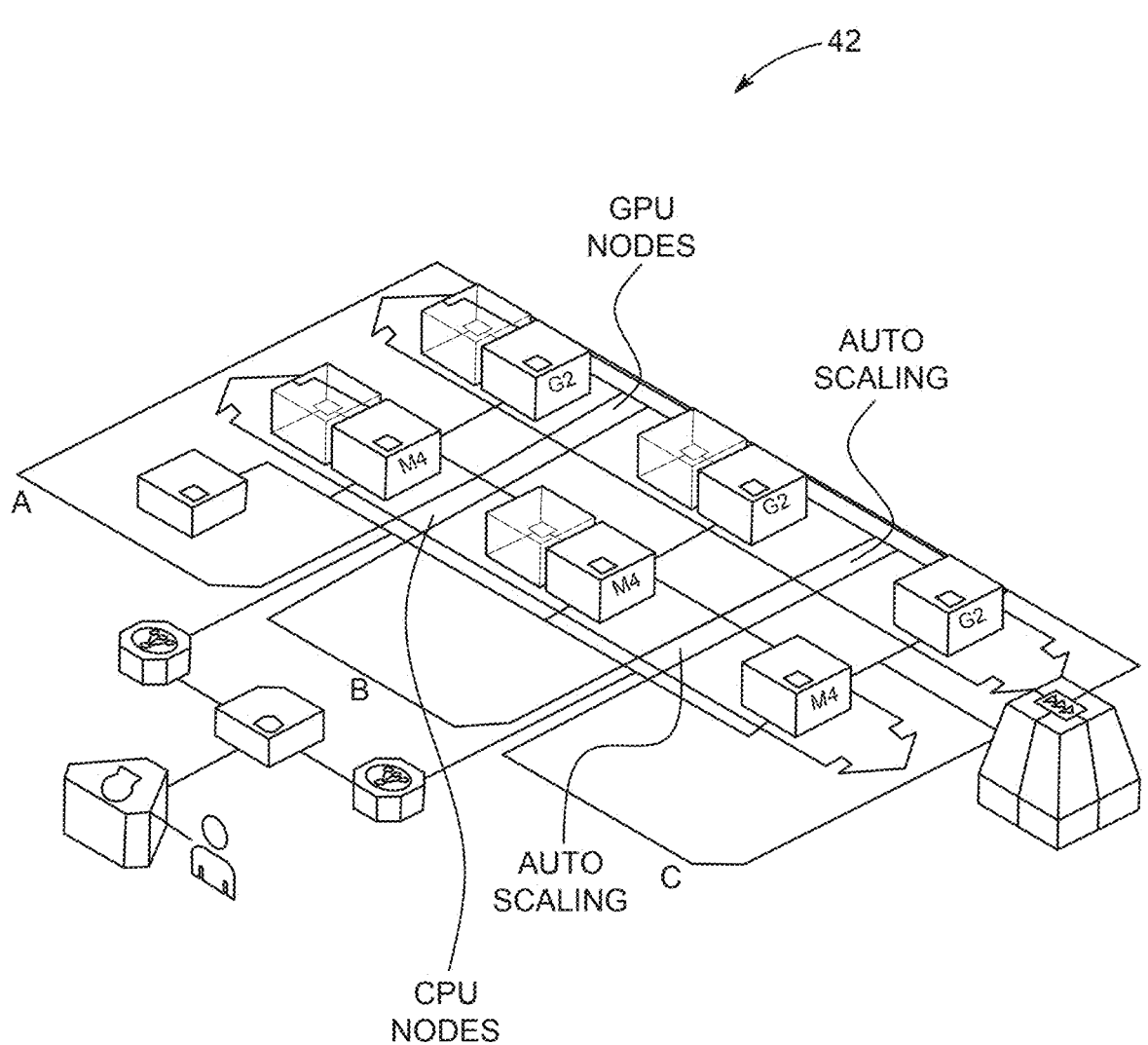
FIG. 28 provides a block diagram illustrating an AI system and its cloud-based computing platforms infrastructure in accordance with an embodiment.

FIG. 27 shows the architect module configured to propose a neural network layout such as the neural network layout and the learner module configured to save a trained state of a neural network such as the trained neural network.

Figure 29:
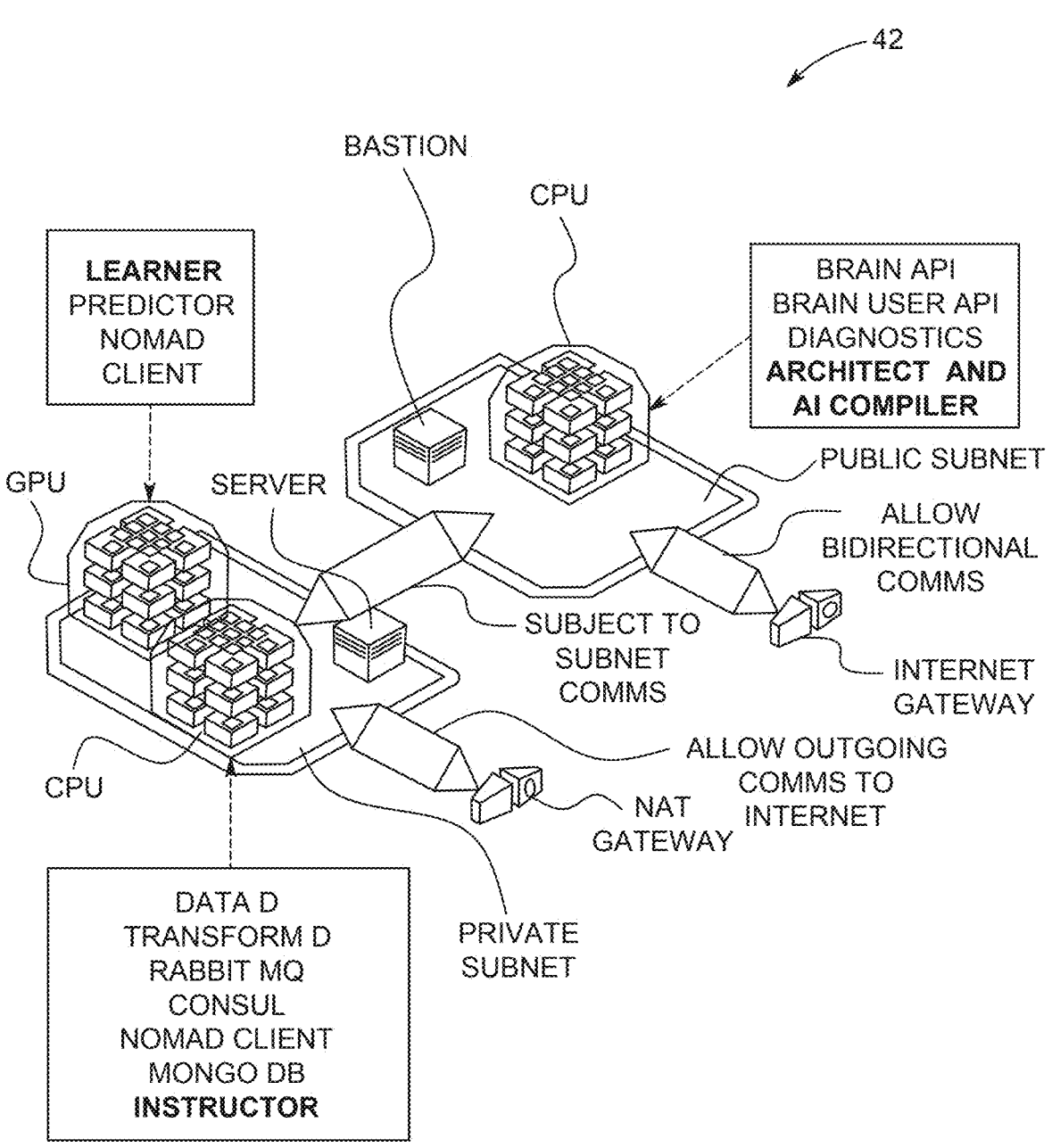
FIG. 29 provides a block diagram illustrating an AI system and its on-premises based computing platforms infrastructure in accordance with an embodiment.
Figure 30:
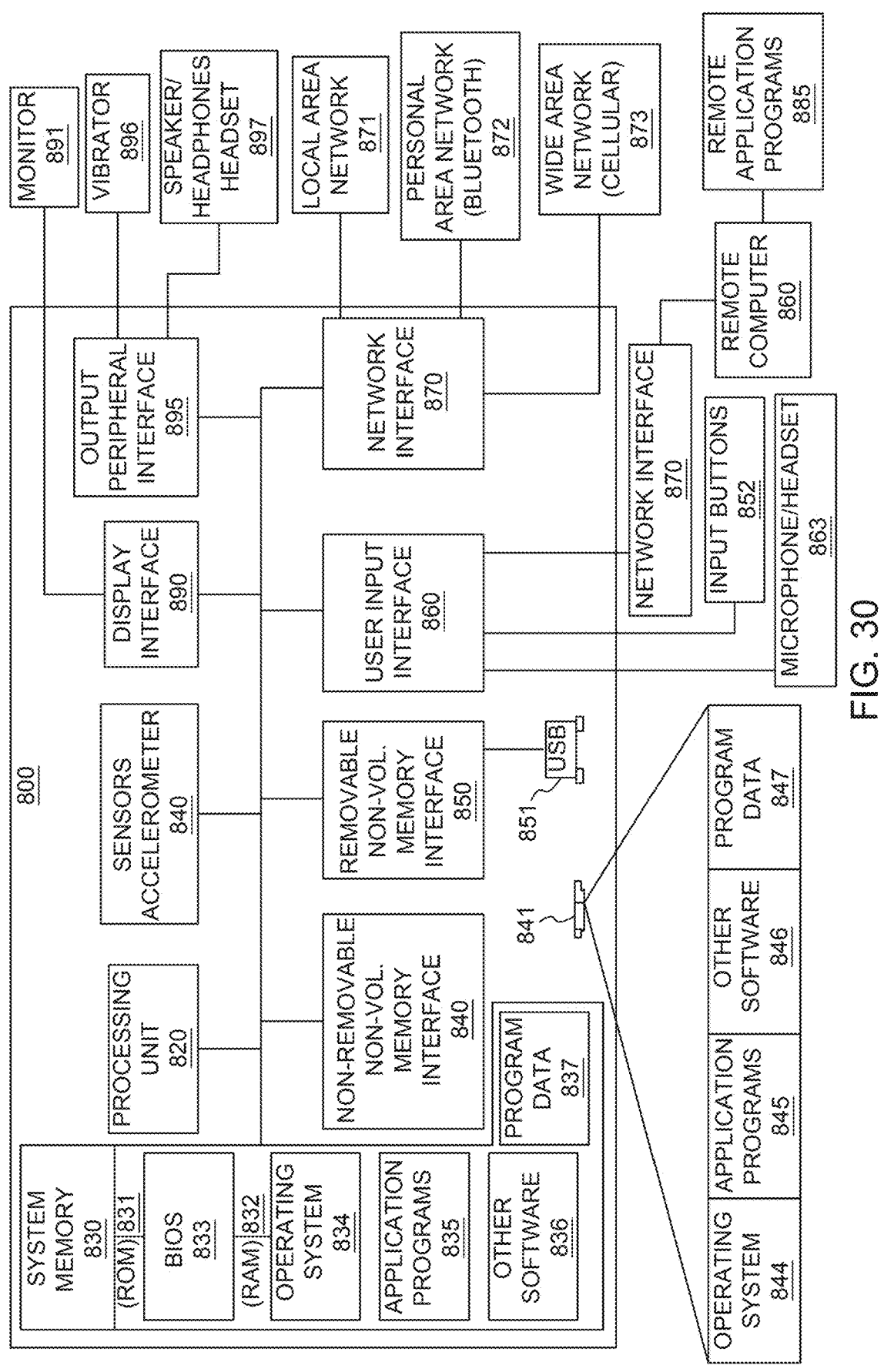
FIG. 30 provides one or more computing systems in accordance with an embodiment.

As illustrated in FIG. 29, a user, such as prior and current surgeons, prior and current assistants, third parties, and the like (users), can interface with the AI system 42 through an online interface. AI system 42 can enable a user to make API and web requests through a domain name system. API load balancer can be configured to distribute the API requests among multiple BRAIN service containers running in a Docker network or containerization platform configured to wrap one or more pieces of software in a complete filesystem containing everything for execution including code, runtime, system tools, system libraries, etc. The web load balancer can be configured to distribute the web requests among multiple web service containers running in the Docker network. The Docker network or Docker BRAIN network can include central processing unit ("CPU") nodes and graphics processing unit ("GPU") nodes, the nodes of which Docker network can be auto scaled as needed. The CPU nodes can be utilized for most BRAIN-service containers running on the Docker network, and the GPU nodes can be utilized for the more computationally intensive components such as TensorFlow and the learner module.

FIG. 29 provides a block diagram illustrating AI system 42 and its on-premises computing platforms infrastructure in accordance with an embodiment of the present.

Computing system 800 that can be, wholly or partially, part of one or more of the server or client computing devices in accordance with an embodiment. Computing system 800 can include, but are not limited to, a processing unit 820 having one or more processing cores, a system memory 830, and a system bus 821 that couples various system components including the system memory 830 to the processing unit 820. The system bus 821 may be any of several types of bus structures selected from a memory bus or memory controller, a peripheral bus, and a local bus using any of a variety of bus architectures.

Computing system 800 typically includes a variety of computing machine-readable media. Computing machine-readable media can be any available media that can be accessed by computing system 800 and includes both volatile and nonvolatile media, and removable and non-removable media. By way of example, and not limitation, computing machine-readable media use includes storage of information, such as computer-readable instructions, data structures, other executable software or other data. Computer-storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other tangible medium which can be used to store the desired information and which can be accessed by the computing device 800. Transitory media such as wireless channels are not included in the machine-readable media. Communication media typically embody computer readable instructions, data structures, other executable software, or other transport mechanism and includes any information delivery media. As an example, some client computing systems on the network 820 of FIG. 7 might not have optical or magnetic storage.

The system memory 830 includes computer storage media in the form of volatile and/or nonvolatile memory such as read only memory (ROM) 831 and random access memory (RAM) 832. A basic input/output system 833 (BIOS) containing the basic routines that help to transfer information between elements within the computing system 800, such as during start-up, is typically stored in ROM 831. RAM 832 typically contains data and/or software that are immediately accessible to and/or presently being operated on by the processing unit 820.

The computing system 800 can also include other removable/non-removable volatile/nonvolatile computer storage media. Other removable/non-removable, volatile/nonvolatile computer storage media that can be used in the example operating environment include, but are not limited to, USB drives and devices, flash memory cards, solid state RAM, solid state ROM, and the like. The solid-state memory 841 is typically connected to the system bus 821 through a non-removable memory interface such as interface 840, and USB drive 851 is typically connected to the system bus 821 by a removable memory interface, such as interface 850.

Figure 31:
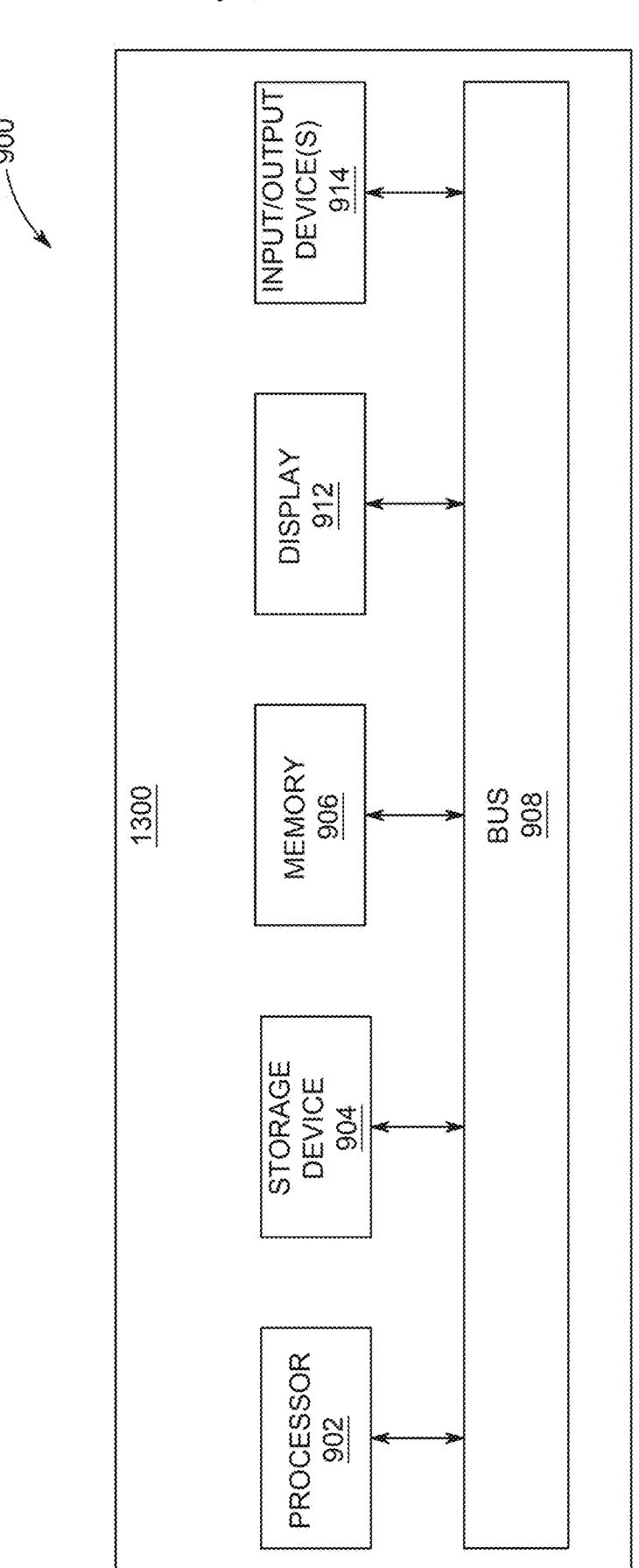
FIG. 31 illustrates one embodiment of block diagram that illustrates components of a computing device of the present invention.

FIG. 31 illustrates one embodiment of block diagram that illustrates components of a computing device 900. The computing device 900 can implement aspects of the present disclosure, and, in particular, aspects of the patient management and 111, including but not limited to a frontend server, a patient data service, the patient care management service, and/or the patient monitoring service. The computing device 900 can communicate with other computing devices.

The computing device 900 can include a hardware processor 902, a data storage device 904, a memory device 906, a bus 908, a display 912, and one or more input/output devices 914. A processor 902 can also be implemented as a combination of computing devices, e.g., a combination of a digital signal processor and a microprocessor, a plurality of microprocessors, one or more microprocessors in conjunction with a digital signal processor, or any other such configuration. The processor 902 can be configured, among other things, to process data, execute programmed instructions 67 of surgical computing device 151 to perform one or more functions, such as process one or more physiological signals to obtain one or measurements, as described herein. The data storage device 904 can include a magnetic disk, optical disk, or flash drive, etc., and is provided and coupled to the bus 908 for storing information and programmed instructions 67 of surgical computing device 151. The memory 906 can include one or more memory devices that store data, including without limitation, random access memory (RAM) and read-only memory (ROM). The computing device 900 may be coupled via the bus 908 to a display 912, such as an LCD display or touch screen, for displaying information to a user, such as a clinician. The computing device 900 may be coupled via the bus 908 to one or more input/output devices 914. The input device 914 can include, but is not limited to, a keyboard, mouse, digital pen, microphone, touch screen, gesture recognition system, voice recognition system, imaging device (which may capture eye, hand, head, or body tracking data and/or placement), gamepad, accelerometer, or gyroscope.

In one embodiment, a control device is coupled to the robotic surgical arms 54. The control device can be configured or programmed to control the robotic surgical arms 54, In one embodiment AI system 42 has a plurality of machine learning algorithms. The robotic surgical arms 54 are at least partially controlled by the AI system 42 and the control device which processes intraoperative data including images captured by cameras and sensor inputs. The machine learning algorithms analyze the intraoperative data in real time, compare it with stored images and procedural information in image recognition and procedure databases. The one or more machine algorithms enable at least a partial identification of anatomical structures. In response to detection of the anatomical structures, the AI system 42 at least partially adjusts movement of the robotic surgical arms 54 to avoid the anatomical structures while performing the robotic surgery procedure. This allows for precise targeting at the surgical site while minimizing damage to surrounding tissue and the anatomical structures near the surgical site. AI system 42 provides a surgeon with improved dexterity when the surgeon uses the robotic surgical arms 54 at the surgical site. The improved dexterity results, at least partially by real time data analysis of the intraoperative data by the one or more machine learning algorithms, precise and adaptive manipulation of the robotic surgical arms 54 at the robotic surgical site, executing a planned surgical step of the robotic surgery procedure using the one or more machine learning algorithms.

Real-time AI image enhancement allows for enhanced identification of anatomical structures, and robotic surgical arms. System 10 provides an online preprocessing framework capable of denoising, deblurring, and color-correcting real-time camera imaging to enhance intraoperative visualization for tumor, blood vessel and nerve identification. System 10 can use augmented reality integrated through AI for overlaying important information such as vitals and hemodynamic state of a patient in real time to the surgeon.

The improved dexterity of the robotic surgical arms 54 can provide seamless integration of real-time data processing, advanced machine learning, and adaptive instrument control. This allows robotic system to perform highly intricate surgical tasks while responding dynamically to intraoperative changes, significantly enhancing surgical precision, safety, and efficiency. In one embodiment, the use of computer vision and machine learning (particularly deep learning) is used to analyze operative video data and recognise the anatomical structures.

The anatomical structures can include one or more of: tumors, blood vessels and nerves. The anatomical structures can include one or more of: skin, subcutaneous tissue, adipose tissue, fascia, muscle, tendons, ligaments, bones, joints, cartilage, hollow or solid organs, vascular structures (arteries, veins, capillaries, lymphatic vessels and nodes), peripheral nerves, spinal cord and nerve roots, autonomic nerves, peritoneum, pleura, and pericardium. These anatomical structures are avoided during the robotic surgical procedure, allowing a more targeted to the robotic surgical site, Identification of these structures intra-operatively can be facilitated by anatomical landmarks. However, these landmarks can be variable. Once these anatomical structures are identified, AI system 42 calculates optimal instrument movements, adjusting parameters such as trajectory, force, and angle to ensure precise targeting while avoiding damage to surrounding tissues.

In one embodiment, system continuously monitors the interaction between the robotic instruments and the surgical site. If irregularities are detected, such as unexpected tissue resistance, anatomical variations, or anomalies in the planned path, AI system 42 prompts immediate recalibration of the robotic arms 54' movements. For instance, if the robotic arms 54 encounter an area with higher tissue density than anticipated, the system calculates the necessary adjustments, such as reducing applied force or changing the angle of approach. These calculations and adjustments occur in real time, allowing the robotic arms 54 to maintain accuracy and avoid unintended damage.

Additionally, the system leverages predictive modeling and historical data can be used to refine movement predictions. Using patterns learned from prior procedures (either surgeon specific or from a database of prior surgeries), the AI system 42 can anticipate challenges such as tissue shifts caused by patient movement or physiological processes such as breathing. By synchronizing robotic movements with these variables, the system ensures smooth and consistent instrument operation. The machine learning algorithms also assign confidence scores to each planned movement based on the analysis of intraoperative data. This can prompt and guide the surgeon to the optimal path.

The robotic arms 54' enhanced dexterity also includes the ability to make ultra-fine movements, such as micro-suturing or precise dissections, by utilizing feedback from sensors, camera and the like. These sensors and cameras produce images, detect pressure, vibration, and other tactile information, which the AI system 42 processes to further refine instrument control. For example, during tumor resection, the system can detect and adjust for subtle differences in tissue texture, ensuring the tumor is removed with minimal impact on surrounding healthy tissue.

At least a portion of the sensor data may contain noisy data, including errors, outliers, and inconsistencies. System 10 provides functionality for identifying, cleaning, and transforming such noisy data to optimize its use in machine learning algorithms. The system includes a preprocessing module, which may be integrated into the system or implemented as a separate component and employs advanced techniques such as rule-based filters, machine learning algorithms, or heuristic methods to detect and address anomalies or inconsistencies. For example, it can identify missing values, duplicate records, or formatting errors and either correct these issues based on predefined rules or remove the problematic records entirely. Additionally, the module can leverage external data sources or context-aware algorithms to validate and enrich the data, enhancing its quality and relevance. The preprocessing functionality is highly adaptable, allowing customization to suit specific dataset requirements or applications. It supports both real-time and batch processing workflows, enabling efficient handling of large-scale data while ensuring data integrity, reliability, and usability for downstream analytics, modeling, or other processes. Further, the system can detect incomplete, incorrect, or inaccurate data and then replace, modify, or delete the affected records. Data cleansing can be performed interactively using data wrangling tools or through batch processing, often implemented via scripts or a data quality firewall, to maintain consistent and reliable datasets.

As a non-limiting example, system 10 provides for data cleaning, also referred to as data scrubbing or data cleansing, that is the process of preparing data for analysis by identifying and correcting errors, inconsistencies, and inaccuracies. This can be achieved in the AI module/engine and/or in a separate preprocessing module.

In one embodiment, system 10 provides for sensor data preprocessing that transforms raw, unstructured, or noisy data into a clean, structured format suitable for analysis. As stated previously, raw sensor data may contain missing values, outliers, inconsistencies, or redundant information, all of which can adversely impact the performance of machine learning algorithms. In one embodiment, system 10 provides systematic data preprocessing.

In one embodiment, system 10 gathers relevant data for sensor data, the sensor data is cleaned and optionally splitting it into training and testing sets. The training set is used to train, while the testing set evaluates its performance As a non-limiting example, system 10 can preprocess sensor data and to eliminate or reduce noise. This can include but is not limited to the following types of sensor data noise: Feature Noise that refers to superfluous or irrelevant features present in the dataset that might cause confusion and impede the process of learning; Systematic Noise: Recurring biases or mistakes in measuring or data collection procedures that cause data to be biased or incorrect; Random Noise: unpredictable fluctuations in data brought on by variables such as measurement errors or ambient circumstances; Background noise: information in the sensor data that is unnecessary or irrelevant and could distract the model from the learning job, and the like.

As a non-limiting example, noise can include measuring errors, anomalies, or discrepancies in the sensor data. Handling noise is important because it might result in AI machine learning algorithm that are unreliable and forecasts that are not correct.

As a non-limiting example, system 10 preprocesses at least of sensor data by a preprocessing module that can be include with or separate from AI module. It can include methods to improve the quality of the sensor data and lessen noise from errors or inconsistencies, such as data cleaning, normalization, and outlier elimination. Sensor data can be preprocessed with the use of Fourier Transform which can be a mathematical technique used to transform signals from the time or spatial domain to the frequency domain. In the context of noise removal, it can help identify and filter out noise by representing the signal as a combination of different frequencies. Relevant frequencies can be retained while noise frequencies can be filtered out.

In one embodiment, constructive learning involves training a machine learning model to distinguish between clean and noisy data instances. This can require labeled data where the noise level is known. The model learns to classify instances as either clean or noisy, allowing for the removal of noisy data points from the dataset.

Autoencoders can be utilized, with autoencoders being neural network architectures that can include an encoder and a decoder. The encoder compresses the input data into a lower-dimensional representation, while the decoder reconstructs the original data from this representation. Autoencoders can be trained to reconstruct clean signals while effectively filtering out noise during the reconstruction process.

As a non-limiting example, principal component analysis (PCA) can be used by system 10 to reduce and/or eliminate noisy data. PCA is a dimensionality reduction technique that identifies the principal components of a dataset, which are orthogonal vectors that capture the maximum variance in the data. By projecting the data onto a reduced set of principal components, PCA can help reduce noise by focusing on the most informative dimensions of the data while discarding noise-related dimensions.

As a non-limiting example, noisy data cross-validation and ensemble models can be used to eliminate or reduce noisy data. Cross-validation is a resampling technique used to assess how well a predictive model generalizes to an independent dataset. It involves partitioning the dataset into complementary subsets, performing training on one subset (training set) and validation on the other (validation set). This process is repeated multiple times with different partitions of the data. Common cross-validation methods include k-fold cross-validation and leave-one-out cross-validation. By training on different subsets of data, cross-validation helps in reducing the impact of noise in the data. It also aids in avoiding overfitting by providing a more accurate estimate of the model's performance. Ensemble learning involves combining multiple individual models to improve predictive performance compared to any single model alone. Ensemble models work by aggregating the predictions of multiple base models, such as decision trees, neural networks, or other machine learning algorithms. Popular ensemble techniques include bagging (bootstrap aggregating), boosting, and stacking. By combining models trained on different subsets of the data or using different algorithms, ensemble models can mitigate the impact of noise in the data. Ensemble methods are particularly effective when individual models may be sensitive to noise or may overfit the data. They help in improving robustness and generalization performance by reducing the variance of the predictions.

As a non-limiting example, system 10 provides for the removable and/or adding the following: missing values that are missing entries that arise due to incomplete data collection or errors during data entry. Inconsistencies; differences in data formats, units, or encoding that can create confusion and errors during processing; outliers which can be extreme or anomalous values that skew results, leading to incorrect insights or predictions; redundancy that can include non-relevant duplicate records which inflate dataset size and misrepresent actual trends; irrelevance with features that are unrelated to target variable can introduce noise and hinder model performance.

Patient health information is collected in real-time data and can be used to improve disease monitoring and management. Additionally, it is used for early disease detection and prevention. The Health Information Technology for Economic and Clinical Health Act (HITECH Act), enacted as part of the American Recovery and Reinvestment Act of 2009, (ARRA) contains provisions that strengthen the privacy and security protections for certain health information established under HIPAA. From blockchain-based solutions to artificial intelligence-powered threat detection systems, system 10 can include resources to mitigate the risks associated with cyber threats and protect the integrity of medical devices including but not limited to surgical robot system 10.

As a non-limiting example, system 10 provides logic resource cybersecurity in response to one or more of regulations and frameworks in the health care industry selected from one or more of: NIST, HIPAA, CIS, COBIT, ISO/IEC 27001, and HITRUST.

In one embodiment, system 10 cyber security resources are included that minimize hacking of patient data in compliance with HIPAA.

In one embodiment cryptography algorithms function by: encrypting data into ciphertext, making it unreadable to unauthorized users; ensuring secure communication by encrypting data during transit; allowing decryption with the correct key to reveal the true contents of a message, and the like. In one embodiment, machine learning algorithms and AI help identify and prevent cyberthreats by: using supervised learning models with labeled data to train a system and; identifying patterns in unlabeled data through unsupervised learning, detecting advanced or emerging cyberthreats.

Each of following references is expressly incorporated herein by reference in its entirety:

Abraham, Ittai, et al. "Low-distortion inference of latent similarities from a multiplex social network." SIAM Journal on Computing 44.3 (2015): 617-668.

58

Aldenderfer, M. S., and R. K. Blashfield. Cluster Analysis, Sage Publications, Los Angeles, 1985.

Anderberg, M. R. (1973). Cluster Analysis for Applications. Academic Press, New York.

Anderson, E. (1957). A semi-graphical method for analysis of complex problems. Proc. Nat. Acad. Sci. USA 43923-927.

Anderson, T. W. (1958). An Introduction to Multivariate Statistical Analysis. Wiley, New York.

Anderson, T, W., and Babadur, R. R. (1962), classification into two multivariate normal distributions with different covariance matrices. Ann. Math. Statist. 33 420-431.

Andrews, D. F. (1972). Plots of high-dimensional data. Biometrics 28 125-136.

Ankerst, M., M. M. Breunig, H.-P. Kriegel, and J. Sander. OPTICS: Ordering Points To Identify Clustering Structure. In Proc. of 1999 ACM-SIGMOD Intl, Conf. on Management of Data, pages 49-60, Philadelphia, Pa., June 1999. ACM Press.

Arabie, P. (1977), clustering representations of group overlap. J. Math. Soc. 5 112-128.

Arabie, P. and Carroll, J. D. (1980). MAPCLUS: A mamatical programming approach to fitting to ADCLUS model. Psychometrika 45211-235.

Arabie, P., L. Hubert, and G. D. Soete. An overview of combinatorial data analysis. In P.

Arabie, L. Hubert, and G. D. Soete, editors, Clustering and Classification, pages 188-217. World Scientific, Singapore, January 1996.

Art, D., Gnanadesikan, R., and Kettenring, J. R. (1982). Data-based metrics for cluster analysis. Utilitas Mamatica 31A 75-99.

Asimov, D. (1985), grand tour. SLAM J. Sci. Statist. Comput. 6 128-143.

Auffarth, Benjamin, Yasumasa Muto, and Yasuharu Kunii. "An artificial system for visual perception in autonomous Robots." Proceedings of IEEE International Conference on Intelligent Engineering Systems. 2005.

Babu, B. Hari, N. Subash Chandra, and T. Venu Gopal. "Clustering Algorithms For High Dimensional Data—A Survey Of Issues And Existing Approaches."

Baker, F. B. (1974). Stability of two hierarchical grouping techniques, Case I: Sensitivity to data errors. J. Amer, Statist. Assoc. 69440-445.

Ball, G., and D. Hall. A Clustering Technique for Summarizing Multivariate Data. Behavior Science, 12:153-155, March 1967.

Banerjee, A., S. Merugu, I. S. Dhillon, and J. Ghosh. Clustering with Bregman Divergences. In Proc. of 2004 SIAM Intl. Conf. on Data Mining, pages 234-245, Lake Buena Vista, Fla., April 2004.

Baraglia, R., Dazzi, P., Mordacchini, M., & Ricci, L. (2013). A peer-to-peer recommender system for self-emerging user communities based on gossip overlays. Journal of Computer and System Sciences, 79 (2), 291-308.

Baragliaa, R., Dazzia, P., Mordacchinib, M., & Riccic, L. A Peer-to-Peer Recommender System for self-emerging user communities based on Gossip Overlays. (2012)

Beck, Carolyn, et al. "Dynamic Coverage and Clustering: A Maximum Entropy Approach." Distributed Decision Making and Control. Springer London, 2012. 215-243.

Becker, P. (1968). Recognitions of Patterns. Polyteknisk, Copenhagen.

Bell, P. A. and Korey, J. L. (1975). QUICLSTR: A FORTRAN program for hierarchical cluster analysis with a large number of subjects. Behavioral Research Methods and Instrumentation 7575.

Berg, Mikko. "Human abilities to perceive, understand, and manage multi-dimensional information with visualizations." (2012).

Birkin, P. Survey Of Clustering Data Mining Techniques. Technical report, Accrue Software, San Jose, Calif., 2002.

Bhat, Sajid Yousuf, and Muhammad Abolish. "A density-based approach for mining overlapping communities from social network interactions." Proceedings of 2nd International Conference on Web Intelligence, Mining and Semantics. ACM, 2012.

Binder, D. A. (1978). Comment on 'Estimating mixtures of normal distributions and switching regressions. j Amer. Statist. Assoc. 73746-747.

Blashfield, R. K., Aldenderfer, M. S. and Morey, L. C. (1982), cluster analysis literature on validation. In Classifying Social Data. (H. Hudson, ed.) 167-176. Jossey-Bass, San Francisco.

Bock, H. H. (1985). On significance tests in cluster analysis. J. Classification 277-108.

Boley, D. Principal Direction Divisive Partitioning, Data Mining and Knowledge Discovery, 2(4):325-344, 1998.

Bosley, Daniel, and Vivian Borst. "A General Unsupervised Clustering Tool for Unstructured Data." matrix 100:2.

Boratto, Ludovico. "Group artificial intelligence with automatic detection and classification of groups." (2012)

Bradley, P. S. and U. M. Fayyad. Refining Initial Points for K-Means Clustering. In Proc. of 15th Int. Conf. on Machine Learning, pages 91-99, Madison, Wis., July 1998. Morgan Kaufmann Publishers Inc.

Breiman, L. Meisel, W. S., and Purcell, E. (1977). Variable kernel estimates of multivariate densities and ie calibration. Technometrics 19 135-144.

Brineman, L., Friedman, J. H., Olshen, R. A., and Stone, C. J. (1984). Classification and Regression Trees, Wadsworth, Belmont, Calif.

Broadbent, S. R. and Hammersley, J. M. (1957). Percolation Processes, I: Crystals and Mazes. Proc. Cambridge Philos. Soc. 53629-641.

Bu, Yingyi, et al. "HaLoop approach to large-scale iterative data analysis." VLDB Journal-International Journal on Very Large Data Bases 21.2 (2012): 169-190.

Buja, A., Hurify, C. and Mcdonald, J. A. (1986). A data viewer for multivariate data. Computer Science and Statistics: Proceedings of 18th Symposium on Interface 171-174.

Cacoullos, T. (1966). Estimation of a multivariate density. Ann. Math. Statist. 18 179-189.

Cal, Rui, et al. "Scalable music artificial intelligence by search." Proceedings of 15th international conference on Multimedia. ACM, 2007.

Carrizosa, Emilio, and Dolores Romero Morales. "Supervised classification and mamatical optimization." Computers & Operations Research 40.1 (2013): 150-165.

Chang, Chin-Chun, and Hsin-Yi Chen. "Semi-supervised clustering with discriminative random fields." Pattern Recognition 45.12 (2012): 4402-4413, Chen, H., Gnanadesikan, R., and Kettenring, J. R. (1974). Statistical methods for grouping corporations. Sankhya B 36 1-28.

Chen, Yen Hung. "k Partition-Distance Problem." Journal of Computational Biology 19.4 (2012): 404-417.

Cheng, Hong, et al. "Clustering large attributed information networks: an efficient incremental computing approach." Data Mining and Knowledge Discovery 25.3 (2012): 450-477, Chernoff, H. (1972), selection of effective attributes for deciding between hyposes using linear discriminant functions. In Frontiers of Pattern Recognition. (S. Watanabe, ed.) 55-60. Academic Press, New York.

Chernoff, H. (1973a). Some measures for discriminating between normal multivariate distributions with unequal covariance matrices. In Multivariate Analysis III. (P. R. Krishnaiah, ed.) 337-344. Academic Press, New York.

Chernoff, H. (1973b), use of faces to represent points in k-dimensional space graphically. J Amer. Statist. Assoc. 68 361-368.

Cherubini, Umberto, and Agnese Sironi, Bond Trading, Market Anomalies and Neural Networks: An Application with Kohonen Nets. No. 012. Society for Computational Economics.

Christou, Ioannis T., George Gekas, and Anna Kyrikou. "A classifier ensemble approach to TV-viewer profile adaptation problem." International Journal of Machine Learning and Cybernetics 3.4 (2012): 313-326.

Clunies-Ross, C. W. and Riffenburgh, R. H. (1960). Geometry and linear discrimination. Biometrika 47185-189.

Cormack, R. M. (1971). A review of classification (with discussion). J Roy. Statist. Soc. A 134321-367.

Cover, T. M. (1968). Estimation by nearest neighbor rule. IEEE Transactions Information ory IT-14 50-55.

Cover, T. M. and Hart, P. B. (1967). Nearest neighbor pattern classification. IEEE Transactions, Information IT-13 21-27.

Dallal, G. E. (1975) A user's guide to J. A. Hartigan's clustering algorithms. (unpublished manuscript) Yale University.

Day, N. E. (1969), Estimating components of a mixture of normal distributions. Biometrika 56463-474.

Day, N. E., and Kerridge, D. F., (1967). A general maximum likelihood discriminant. Biometrics 23313-323. 94 de Master, Trabajo Fin. "Novelty and Diversity Enhancement and Evaluation in Recommender Systems." (2012), Defays, D. (1977). An efficient algorithm for a complete link method. Computer Journal 20364-366, Derrac, Joaquín, Isaac Triguero, Salvador García, and Francisco Herrera. "Integrating instance selection, instance weighting, and feature weighting for nearest neighbor classifiers by coevolutionary algorithms."

It is to be understood that present disclosure is not to be limited to specific examples illustrated and that modifications and or examples are intended to be included within scope of appended claims. Moreover, although foregoing description and associated drawings describe examples of present disclosure in context of certain illustrative combinations of elements and/or functions, it should be appreciated that different combinations of elements and/or functions may be provided by alternative implementations without departing from scope of appended claims. Accordingly, parenetical reference numerals in appended claims are presented for illustrative purposes only and are not intended to limit scope of claimed subject matter to specific examples provided in present disclosure.

The invention claimed is:

1. A robotic surgical system, comprising:
a surgeon console including a display and a planning module configured to allow a surgeon to create a surgical plan for a robotic surgical procedure;
a patient console operatively coupled to the surgeon console and including one or more robotic surgical arms and a plurality of robotic surgical instruments carried by the one or more robotic surgical arms;
a robotic surgical control system operatively coupled to the surgeon console and the patient console, the robotic surgical control system including a surgical computing device, the surgical computing device comprising at least one computer processor, a memory storing surgical instructions, and a non-transitory computer-readable storage medium storing computer-executable instructions including the surgical instructions, the surgical computing device being configured to access an image recognition database and a procedure database;

a sensor array operatively coupled to at least one of the patient console and the robotic surgical control system and configured to acquire intraoperative data comprising imaging data from a surgical site of a patient; and an artificial intelligence (AI) system including an AI architecture implemented by the at least one computer processor and executing a plurality of machine learning algorithms, the AI system having access to the non-transitory computer-readable storage medium, being operatively coupled to the sensor array, the robotic surgical control system, and the patient console, and being configured to: receive the intraoperative data from the sensor array; clean imaging data included in the intraoperative data and transform the imaging data into a format suitable for analysis; and analyze the intraoperative data, including the imaging data, using the plurality of machine learning algorithms and at least one of the image recognition database and the procedure database to identify anatomical structures of the patient at the surgical site and generate control signals, the anatomical structures including one or more critical anatomical structures selected from the one or more of: subcutaneous tissue, adipose tissue, fascia, muscle, tendons, ligaments, bones, joints, cartilage, hollow organs, solid organs, vascular structures, peripheral nerves, spinal cord, nerve roots, autonomic nerves, peritoneum, pleura, pericardium, and tumors, in response to the control signals, the robotic surgical control system causes the one or more robotic surgical arms to move during the robotic surgical procedure so as to avoid at least one of the critical anatomical structures while performing the surgical plan; and wherein execution of the computer-executable instructions further causes the robotic surgical system to perform one or more of: monitoring the robotic surgical procedure; executing a planned surgical step of the robotic surgical procedure using the plurality of machine learning algorithms; and determining that the robotic surgical procedure has been completed.

2. The system of claim 1, wherein the AI system is configured to detect a deviation between the surgical plan and the intraoperative data and, in response to detecting the deviation, generates a recommendation to modify the surgical plan and presents the recommendation on the display of the surgeon console.

3. The system of claim 1, wherein identification of the patient anatomical structures intraoperatively is facilitated by patient anatomical landmarks.

4. The system of claim 1, wherein once the patient anatomical structures are identified, the AI system calculates movements of the one or more robotic surgical arms and the plurality of surgical instruments.

5. The system of claim 1, wherein the AI system calculates movements of the one or more robotic surgical arms and the plurality of robotic surgical instruments and adjusts one or more parameters, including force and angle to ensure effective targeting.

6. The system of claim 1, wherein the robotic surgical system continuously monitors the interaction between the one or more robotic surgical arms and the plurality of robotic surgical instruments and the surgical site.

7. The system of claim 1, wherein the system uses predictive modeling and historical data for the one or more robotic arms and the plurality of robotic surgical instruments to update movement predictions.

8. The system of claim 1, wherein patterns learned from prior surgical procedures are used during the robotic surgical procedure.

9. The system of claim 1, wherein the plurality of machine learning algorithms assigns confidence scores to each planned movement based on the analysis of intraoperative data.

10. The system of claim 1, wherein the plurality of machine learning algorithms assigns confidence scores to each planned movement based on the analysis of intraoperative data and use the confidence scores to guide the surgeon to a selected movement path of the one or more robotic surgical arms and the plurality of robotic surgical instruments.

11. The system of claim 1, wherein the improved dexterity of one or more robotic surgical arms and the plurality of robotic surgical instruments also includes the ability to make one or more of: ultra-fine movements, and effective dissections, at least in part by utilizing feedback.

12. The system of claim 1, wherein during tumor resection the robotic surgical system can detect and adjust for differences in tissue texture and adjusts at least one movement parameter of the one or more robotic surgical arms in response to the detected differences.

13. The system of claim 1, wherein at least a portion of the intraoperative data includes noisy data, errors, outliers, and inconsistencies.

14. The system of claim 13, wherein the system provides functionality for identifying, cleaning, and transforming the noisy data for use in the plurality of machine learning algorithms.

* * * * *